US012733931B2

(12) United States Patent
Leimbach et al.

(10) Patent No.: US 12,733,931 B2
(45) **Date of Patent: *Sep. 15, 2026**

(54) FEEDBACK ALGORITHMS FOR MANUAL BAILOUT SYSTEMS FOR SURGICAL INSTRUMENTS

(71) Applicant: CILAG GMBH INTERNATIONAL, Zug (CH)

(72) Inventors: Richard L. Leimbach, Cincinnati, OH (US); Shane R. Adams, Lebanon, OH (US); Mark D. Overmyer, Cincinnati, OH (US); Brett E. Swensgard, West Chester, OH (US); Thomas W. Lytle, IV, Liberty Township, OH (US); Frederick E. Shelton, IV, Hillsboro, OH (US); Kevin L. Houser, Springboro, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/027,989

(22) Filed: Jan. 17, 2025

(65) Prior Publication Data

US 2025/0160831 A1 May 22, 2025

Related U.S. Application Data

(63) Continuation of application No. 16/587,803, filed on Sep. 30, 2019, now Pat. No. 12,285,166, which is a (Continued)

(51) Int. Cl.
*A61B 17/00* (2006.01)
*A61B 17/072* (2006.01)
(Continued)

(52) U.S. Cl.
CPC .................. *A61B 17/07207* (2013.01); *A61B 17/320016* (2013.01); *A61B 90/98* (2016.02);
(Continued)

(58) Field of Classification Search
CPC ...... A61B 17/07207; A61B 17/320016; A61B 90/98; A61B 17/068; A61B 17/0686;
(Continued)

(56) References Cited

U.S. PATENT DOCUMENTS

| | | | |
|---|---|---|---|
| 1,912,783 | A | 6/1933 | Meyer |
| 2,256,295 | A | 9/1941 | Schmid |

(Continued)

FOREIGN PATENT DOCUMENTS

| | | | |
|---|---|---|---|
| AU | 2006262282 | A1 | 1/2007 |
| AU | 2012203035 | A1 | 6/2012 |

(Continued)

OTHER PUBLICATIONS

Makerbot, 10 Advantages of 3D Printing, 2020 (retrieved via the wayback machine), Makerbot.com (Year: 2020).

(Continued)

*Primary Examiner* — Robert F Long
(74) *Attorney, Agent, or Firm* — Troutman Pepper Locke LLP

(57) ABSTRACT

A surgical system includes a firing rod configured to be translated to deploy surgical staples during a firing stroke and a microcontroller configured to adjust firing rod velocity by pausing movement of the firing rod for a predefined period of time when the microcontroller detects a current draw by a motor driving the firing rod that exceeds a predefined threshold value. After the pause, the firing stroke can be resumed and if the current draw increase is less than the threshold value, the microcontroller can proceed cause (Continued)

the motor to drive the firing rod through the firing stroke without adjusting the velocity of the firing element.

23 Claims, 64 Drawing Sheets

Related U.S. Application Data continuation of application No. 16/041,145, filed on Jul. 20, 2018, now abandoned, which is a continuation of application No. 14/226,093, filed on Mar. 26, 2014, now Pat. No. 10,028,761.

(51) Int. Cl.

| | |
|---|---|
| ***A61B 17/32*** | (2006.01) |
| ***A61B 90/98*** | (2016.01) |
| ***A61L 2/07*** | (2006.01) |
| ***A61L 2/081*** | (2026.01) |
| ***A61L 2/082*** | (2026.01) |
| ***A61L 2/087*** | (2026.01) |
| ***A61L 2/16*** | (2006.01) |
| ***A61L 2/206*** | (2026.01) |
| ***A61L 2/26*** | (2006.01) |
| ***B25F 3/00*** | (2006.01) |
| ***B25F 5/00*** | (2006.01) |
| ***H01M 10/42*** | (2006.01) |
| ***H01R 35/02*** | (2006.01) |
| ***H01R 39/08*** | (2006.01) |
| ***H01R 39/10*** | (2006.01) |
| ***H02J 4/25*** | (2026.01) |
| *A61B 17/068* | (2006.01) |
| *A61B 17/29* | (2006.01) |
| *A61B 18/14* | (2006.01) |
| *A61B 34/00* | (2016.01) |
| *A61B 90/00* | (2016.01) |
| *A61B 90/90* | (2016.01) |
| *A61L 103/15* | (2026.01) |
| *H01M 10/48* | (2006.01) |
| *H01M 50/213* | (2021.01) |
| *H01R 39/64* | (2006.01) |
| *H02J 7/02* | (2016.01) |
| *H02J 7/82* | (2026.01) |
| *H02J 7/90* | (2026.01) |

(52) U.S. Cl.

CPC ................. *A61L 2/07* (2013.01); *A61L 2/081* (2013.01); *A61L 2/082* (2013.01); *A61L 2/087* (2013.01); *A61L 2/16* (2013.01); *A61L 2/206* (2013.01); *A61L 2/26* (2013.01); *B25F 3/00* (2013.01); *B25F 5/00* (2013.01); *H01M 10/425* (2013.01); *H01R 35/025* (2013.01); *H01R 39/08* (2013.01); *H01R 39/10* (2013.01); *H02J 4/25* (2026.01); *A61B 2017/00017* (2013.01); *A61B 2017/00039* (2013.01); *A61B 2017/00115* (2013.01); *A61B 2017/00119* (2013.01); *A61B 2017/00123* (2013.01); *A61B 2017/00137* (2013.01); *A61B 2017/00199* (2013.01); *A61B 2017/00212* (2013.01); *A61B 2017/00221* (2013.01); *A61B 2017/00225* (2013.01); *A61B 2017/00367* (2013.01); *A61B 2017/00398* (2013.01); *A61B 2017/00407* (2013.01); *A61B 2017/0046* (2013.01); *A61B 2017/00464* (2013.01); *A61B 2017/00477* (2013.01); *A61B 2017/00725* (2013.01); *A61B 2017/00734* (2013.01); *A61B 17/068* (2013.01); *A61B 17/0686* (2013.01); *A61B 2017/07271* (2013.01); *A61B 2017/07278* (2013.01); *A61B 2017/07285* (2013.01); *A61B 2017/2927* (2013.01); *A61B 2017/2929* (2013.01); *A61B 18/1445* (2013.01); *A61B 34/76* (2016.02); *A61B 2090/065* (2016.02); *A61B 2090/0803* (2016.02); *A61B 2090/0807* (2016.02); *A61B 2090/0808* (2016.02); *A61B 2090/081* (2016.02); *A61B 2090/0811* (2016.02); *A61B 2090/0813* (2016.02); *A61B 2090/0814* (2016.02); *A61B 90/90* (2016.02); *A61L 2103/15* (2026.01); *A61L 2202/14* (2013.01); *H01M 2010/4278* (2013.01); *H01M 10/48* (2013.01); *H01M 50/213* (2021.01); *H01M 2220/30* (2013.01); *H01R 39/64* (2013.01); *H01R 2201/12* (2013.01); *H02J 7/02* (2013.01); *H02J 7/82* (2026.01); *H02J 7/90* (2026.01); *H02J 7/971* (2026.01); *H02J 7/975* (2026.01)

(58) Field of Classification Search

CPC ..... A61B 18/1445; A61B 34/76; A61B 90/90; A61B 2017/00017; A61B 2017/00039; A61B 2017/00115; A61B 2017/00119; A61B 2017/00123; A61B 2017/00137; A61B 2017/00199; A61B 2017/00212; A61B 2017/00221; A61B 2017/00225; A61B 2017/00367; A61B 2017/00398; A61B 2017/00407; A61B 2017/0046; A61B 2017/00464; A61B 2017/00477; A61B 2017/00725; A61B 2017/00734; A61B 2017/07271; A61B 2017/07278; A61B 2017/07285; A61B 2017/2927; A61B 2017/2929; A61B 2090/065; A61B 2090/0803; A61B 2090/0807; A61B 2090/0808; A61B 2090/081; A61B 2090/0811; A61B 2090/0813; A61B 2090/0814; A61B 90/06; A61B 2017/00084; A61B 2034/302; A61L 2/07; A61L 2/081; A61L 2/082; A61L 2/087; A61L 2/16; A61L 2/206; A61L 2/26; A61L 2202/14; A61L 2202/24; B25F 3/00; B25F 5/00; H01M 10/425; H01M 10/48; H01M 50/213; H01M 2010/4278; H01M 2220/30; H01M 10/443; H01R 35/025; H01R 39/08; H01R 39/10; H01R 39/64; H01R 2201/12; H02J 5/00; H02J 7/0048; H02J 7/007; H02J 7/007188; H02J 7/007192; H02J 7/02; H02J 2310/23; Y02E 60/10

USPC ......... 227/175.1–182.1, 8, 19; 606/139, 142, 606/143, 205–208

See application file for complete search history.

(56) References Cited

U.S. PATENT DOCUMENTS

| | | | |
|---|---|---|---|
| 3,899,829 | A | 8/1975 | Storm et al. |
| 4,169,476 | A | 10/1979 | Hiltebrandt |
| 4,250,817 | A | 2/1981 | Michel |
| 4,316,512 | A | 2/1982 | Kibblewhite et al. |
| 4,726,247 | A | 2/1988 | Hormann |
| 4,819,495 | A | 4/1989 | Hormann |
| 4,949,927 | A | 8/1990 | Madocks et al. |
| 5,019,077 | A | 5/1991 | De Bastiani et al. |
| 5,154,242 | A | 10/1992 | Soshin et al. |
| 5,156,151 | A | 10/1992 | Imran |
| 5,163,842 | A | 11/1992 | Nonmura |

(56) References Cited

U.S. PATENT DOCUMENTS 5,188,126 A 2/1993 Fabian et al.
5,236,629 A 8/1993 Mahabadi et al.
5,251,801 A 10/1993 Ruckdeschel et al.
5,300,087 A 4/1994 Knoepfler
5,318,589 A 6/1994 Lichtman
5,354,215 A 10/1994 Viracola
5,368,599 A 11/1994 Hirsch et al.
5,440,215 A 8/1995 Gilmore
5,454,824 A 10/1995 Fontayne et al.
5,478,308 A 12/1995 Cartmell et al.
5,535,937 A 7/1996 Boiarski et al.
5,558,671 A 9/1996 Yates
5,562,694 A 10/1996 Sauer et al.
5,607,303 A 3/1997 Nakamura
5,611,813 A 3/1997 Lichtman
5,630,799 A 5/1997 Beiser et al.
5,700,265 A 12/1997 Romano
5,704,792 A 1/1998 Sobhani
5,746,770 A 5/1998 Zeitels et al.
5,798,752 A 8/1998 Buxton et al.
5,810,240 A 9/1998 Robertson
5,893,863 A 4/1999 Yoon
5,922,001 A 7/1999 Yoon
5,922,003 A 7/1999 Anctil et al.
5,954,259 A 9/1999 Viola et al.
6,023,275 A 2/2000 Horvitz et al.
6,454,656 B2 9/2002 Brissette et al.
6,463,824 B1 10/2002 Prell et al.
6,569,173 B1 5/2003 Blatter et al.
6,616,446 B1 9/2003 Schmid
6,626,901 B1 9/2003 Treat et al.
6,757,969 B1 7/2004 Chan et al.
6,860,169 B2 3/2005 Shinozaki
6,927,315 B1 8/2005 Heinecke et al.
6,981,941 B2 * 1/2006 Whitman ............... A61B 34/71
606/1
7,075,412 B1 7/2006 Reynolds et al.
7,101,363 B2 9/2006 Nishizawa et al.
7,112,201 B2 9/2006 Truckai et al.
7,156,848 B2 1/2007 Dycus et al.
7,169,146 B2 1/2007 Truckai et al.
7,252,641 B2 8/2007 Thompson et al.
7,311,709 B2 12/2007 Truckai et al.
7,354,440 B2 4/2008 Truckai et al.
7,430,849 B1 10/2008 Coutts et al.
D580,942 S 11/2008 Oshiro et al.
7,572,298 B2 8/2009 Roller et al.
7,644,016 B2 1/2010 Nycz et al.
7,644,484 B2 1/2010 Vereschagin
7,705,253 B2 4/2010 Krieger et al.
7,823,076 B2 10/2010 Borovsky et al.
7,877,869 B2 2/2011 Mehdizadeh et al.
7,879,367 B2 2/2011 Heublein et al.
7,918,377 B2 4/2011 Measamer et al.
7,952,464 B2 5/2011 Nikitin et al.
8,052,697 B2 11/2011 Phillips
8,348,948 B2 1/2013 Bahney
8,381,834 B2 2/2013 Barhitte et al.
8,409,234 B2 4/2013 Stahler et al.
8,531,153 B2 9/2013 Baarman et al.
8,840,004 B2 9/2014 Holsten et al.
8,855,822 B2 10/2014 Bartol et al.
8,871,829 B2 10/2014 Gerold et al.
8,937,408 B2 1/2015 Ganem et al.
8,960,519 B2 2/2015 Whitman et al.
9,028,529 B2 5/2015 Fox et al.
9,039,736 B2 5/2015 Scirica et al.
9,095,642 B2 8/2015 Harder et al.
9,154,189 B2 10/2015 Von Novak et al.
9,226,686 B2 1/2016 Blair
9,259,268 B2 2/2016 Behnke, II et al.
9,283,334 B2 3/2016 Mantell et al.
9,398,911 B2 7/2016 Auld
9,452,020 B2 9/2016 Griffiths et al.
9,477,649 B1 10/2016 Davidson et al.
9,515,366 B2 12/2016 Herbsommer et al.
9,522,005 B2 12/2016 Williams et al.
9,554,854 B2 1/2017 Yates et al.
9,561,082 B2 2/2017 Yen et al.
9,566,064 B2 2/2017 Williams et al.
9,572,552 B1 2/2017 Bodor et al.
9,651,032 B2 5/2017 Weaver et al.
9,662,130 B2 5/2017 Bartels et al.
9,700,381 B2 7/2017 Girbau
9,713,466 B2 7/2017 Kostrzewski
9,737,323 B2 8/2017 Thapliyal et al.
9,751,176 B2 9/2017 Mcroberts et al.
9,801,679 B2 10/2017 Trees et al.
9,901,358 B2 2/2018 Faller et al.
9,980,740 B2 5/2018 Krause et al.
10,004,552 B1 6/2018 Kleyman et al.
10,064,642 B2 9/2018 Marczyk et al.
10,146,423 B1 12/2018 Reed et al.
10,251,645 B2 4/2019 Kostrzewski
10,285,724 B2 5/2019 Faller et al.
10,285,750 B2 5/2019 Coulson et al.
10,314,579 B2 6/2019 Chowaniec et al.
10,368,866 B2 8/2019 Wang et al.
10,374,544 B2 8/2019 Yokoyama et al.
10,383,631 B2 8/2019 Collings et al.
10,433,842 B2 10/2019 Amariglio et al.
10,500,004 B2 12/2019 Hanuschik et al.
10,512,464 B2 12/2019 Park et al.
10,524,870 B2 1/2020 Saraliev et al.
10,561,412 B2 2/2020 Bookbinder et al.
10,589,410 B2 3/2020 Aho
D882,783 S 4/2020 Shelton, IV et al.
10,610,225 B2 4/2020 Reed et al.
10,617,438 B2 4/2020 O'Keefe et al.
10,675,080 B2 6/2020 Woloszko et al.
10,695,119 B2 6/2020 Smith
10,729,434 B2 8/2020 Harris et al.
10,729,435 B2 8/2020 Richard
10,736,702 B2 8/2020 Harris et al.
10,737,398 B2 8/2020 Remirez et al.
10,869,663 B2 12/2020 Shelton, IV et al.
10,959,726 B2 3/2021 Williams et al.
11,005,291 B2 5/2021 Calderoni
11,039,849 B2 6/2021 Bucciaglia et al.
11,045,196 B2 6/2021 Olson et al.
11,045,199 B2 6/2021 Mozdzierz et al.
11,116,594 B2 9/2021 Beardsley
11,141,159 B2 10/2021 Scheib et al.
11,166,773 B2 11/2021 Ragosta et al.
11,172,580 B2 11/2021 Gaertner, II
11,197,672 B2 12/2021 Dunki-Jacobs et al.
11,207,089 B2 12/2021 Kostrzewski et al.
11,304,697 B2 4/2022 Fanelli et al.
11,304,704 B2 4/2022 Thomas et al.
11,311,295 B2 4/2022 Wingardner et al.
D950,728 S 5/2022 Bakos et al.
D952,144 S 5/2022 Boudreaux
11,317,912 B2 5/2022 Jenkins et al.
11,317,978 B2 5/2022 Cameron et al.
11,350,928 B2 * 6/2022 Shelton, IV ............ H02J 7/007
11,376,082 B2 7/2022 Shelton, IV et al.
D964,564 S 9/2022 Boudreaux
11,439,391 B2 9/2022 Bruns et al.
D966,512 S 10/2022 Shelton, IV et al.
D967,421 S 10/2022 Shelton, IV et al.
D971,232 S 11/2022 Siebel et al.
11,484,309 B2 11/2022 Harris et al.
D974,560 S 1/2023 Shelton, IV et al.
D975,278 S 1/2023 Shelton, IV et al.
D975,850 S 1/2023 Shelton, IV et al.
D975,851 S 1/2023 Shelton, IV et al.
D976,401 S 1/2023 Shelton, IV et al.
11,553,911 B2 1/2023 Shelton, IV et al.
11,564,682 B2 1/2023 Timm et al.
11,628,006 B2 4/2023 Henderson et al.
12,076,004 B2 * 9/2024 Overmyer ............ A61B 17/068
2001/0030219 A1 10/2001 Green et al.
2001/0045442 A1 11/2001 Whitman
2002/0054158 A1 5/2002 Asami

(56) References Cited

U.S. PATENT DOCUMENTS

2002/0066764 A1 6/2002 Perry et al.
2002/0082612 A1 6/2002 Moll et al.
2002/0087148 A1 7/2002 Brock et al.
2002/0087179 A1 7/2002 Culp et al.
2002/0111621 A1 8/2002 Wallace et al.
2002/0117533 A1 8/2002 Milliman et al.
2002/0133236 A1 9/2002 Rousseau
2002/0153856 A1 10/2002 Gilmore
2002/0161277 A1 10/2002 Boone et al.
2003/0018323 A1 1/2003 Wallace et al.
2003/0028236 A1 2/2003 Gillick et al.
2003/0047582 A1 3/2003 Sonnenschein et al.
2003/0050628 A1 3/2003 Whitman et al.
2003/0105475 A1 6/2003 Sancoff et al.
2003/0135204 A1 7/2003 Lee et al.
2003/0144660 A1 7/2003 Mollenauer
2003/0181800 A1 9/2003 Bonutti
2003/0216619 A1 11/2003 Scirica et al.
2003/0235450 A1 12/2003 Okamoto et al.
2004/0045982 A1* 3/2004 Herman ............ B05C 17/00506 222/145.5
2004/0111081 A1 6/2004 Whitman et al.
2004/0216292 A1 11/2004 Patton
2004/0231870 A1 11/2004 Mccormick et al.
2005/0023325 A1 2/2005 Gresham et al.
2005/0044489 A1 2/2005 Yamagami et al.
2005/0046191 A1 3/2005 Cole et al.
2005/0079088 A1 4/2005 Wirth et al.
2005/0085838 A1 4/2005 Thompson et al.
2005/0090709 A1 4/2005 Okada et al.
2005/0125028 A1 6/2005 Looper et al.
2005/0127686 A1 6/2005 Akinfiev et al.
2005/0145672 A1 7/2005 Schwemberger et al.
2005/0263304 A1 12/2005 Sainomoto et al.
2005/0267464 A1 12/2005 Truckai et al.
2005/0267529 A1 12/2005 Crockett et al.
2006/0011698 A1 1/2006 Okada et al.
2006/0020272 A1 1/2006 Gildenberg
2006/0142656 A1 6/2006 Malackowski et al.
2006/0241691 A1 10/2006 Wilk
2006/0278680 A1 12/2006 Viola et al.
2006/0289600 A1 12/2006 Wales et al.
2007/0027459 A1 2/2007 Horvath et al.
2007/0043338 A1 2/2007 Moll et al.
2007/0055305 A1 3/2007 Schnyder et al.
2007/0162056 A1 7/2007 Gerbi et al.
2007/0175951 A1 8/2007 Shelton et al.
2007/0179476 A1 8/2007 Shelton et al.
2007/0194081 A1 8/2007 Hueil et al.
2007/0221701 A1 9/2007 Ortiz et al.
2007/0227470 A1 10/2007 Cole et al.
2007/0260242 A1 11/2007 Dycus et al.
2008/0000941 A1 1/2008 Sonnenschein et al.
2008/0007237 A1 1/2008 Nagashima et al.
2008/0046000 A1 2/2008 Lee et al.
2008/0094228 A1 4/2008 Welch et al.
2008/0126984 A1 5/2008 Fleishman et al.
2008/0216704 A1 9/2008 Eisenbeis et al.
2008/0255421 A1 10/2008 Hegeman et al.
2008/0255607 A1 10/2008 Zemlok
2008/0296347 A1 12/2008 Shelton, IV et al.
2008/0308607 A1 12/2008 Timm et al.
2008/0308807 A1 12/2008 Yamazaki et al.
2009/0007014 A1 1/2009 Coomer et al.
2009/0012556 A1* 1/2009 Boudreaux .......... A61B 17/068 600/587
2009/0030437 A1 1/2009 Houser et al.
2009/0057369 A1 3/2009 Smith et al.
2009/0090763 A1 4/2009 Zemlok et al.
2009/0114701 A1 5/2009 Zemlok et al.
2009/0120994 A1 5/2009 Murray et al.
2009/0138003 A1 5/2009 Deville et al.
2009/0143797 A1 6/2009 Smith et al.
2009/0204925 A1 8/2009 Bhat et al.
2009/0206143 A1 8/2009 Huitema et al.
2009/0264940 A1 10/2009 Beale et al.
2010/0002013 A1 1/2010 Kagaya
2010/0036441 A1 2/2010 Procter
2010/0076474 A1* 3/2010 Yates ................. A61B 17/3205 606/139
2010/0089970 A1 4/2010 Smith et al.
2010/0094312 A1 4/2010 Ruiz Morales et al.
2010/0106167 A1 4/2010 Boulnois et al.
2010/0125786 A1 5/2010 Ozawa et al.
2010/0168741 A1 7/2010 Sanai et al.
2010/0193569 A1 8/2010 Yates et al.
2010/0194541 A1 8/2010 Stevenson et al.
2010/0198159 A1 8/2010 Voss et al.
2010/0200260 A1 8/2010 Mikami et al.
2010/0206598 A1 8/2010 Elsmark et al.
2010/0237124 A1* 9/2010 Shima ....................... B25C 1/06 227/129
2010/0241115 A1 9/2010 Benamou et al.
2010/0264194 A1 10/2010 Huang et al.
2010/0267525 A1 10/2010 Tanner
2010/0325568 A1 12/2010 Pedersen et al.
2010/0327041 A1 12/2010 Milliman et al.
2010/0332031 A1 12/2010 Itkowitz et al.
2011/0017801 A1 1/2011 Zemlok et al.
2011/0022032 A1* 1/2011 Zemlok ............ A61B 17/07207 606/1
2011/0034910 A1 2/2011 Ross et al.
2011/0118754 A1 5/2011 Dachs, II et al.
2011/0139851 A1 6/2011 Mccuen
2011/0155785 A1 6/2011 Laurent et al.
2011/0198381 A1 8/2011 Mccardle et al.
2011/0203238 A1 8/2011 Witter et al.
2011/0204119 A1 8/2011 Mccuen
2011/0224543 A1 9/2011 Johnson et al.
2011/0278035 A1 11/2011 Chen
2011/0295299 A1 12/2011 Braithwaite et al.
2012/0010615 A1 1/2012 Cummings et al.
2012/0029550 A1 2/2012 Forsell
2012/0055972 A1 3/2012 Marczyk
2012/0080477 A1 4/2012 Leimbach et al.
2012/0080491 A1 4/2012 Shelton, IV et al.
2012/0101488 A1 4/2012 Aldridge et al.
2012/0116263 A1 5/2012 Houser et al.
2012/0116379 A1 5/2012 Yates et al.
2012/0132663 A1 5/2012 Kasvikis et al.
2012/0138658 A1 6/2012 Ullrich et al.
2012/0143175 A1 6/2012 Hermann et al.
2012/0199372 A1 8/2012 Nishikawa et al.
2012/0199632 A1 8/2012 Spivey et al.
2012/0203213 A1 8/2012 Kimball et al.
2012/0223121 A1* 9/2012 Viola ............... A61B 17/07207 227/175.1
2012/0233298 A1 9/2012 Verbandt et al.
2012/0241494 A1 9/2012 Marczyk
2012/0241503 A1 9/2012 Baxter, III et al.
2012/0256494 A1 10/2012 Kesler et al.
2012/0286019 A1 11/2012 Hueil et al.
2012/0303002 A1 11/2012 Chowaniec et al.
2012/0310254 A1 12/2012 Manzo et al.
2012/0312861 A1 12/2012 Gurumurthy et al.
2012/0330285 A1 12/2012 Hartoumbekis et al.
2013/0038263 A1* 2/2013 Faucher .................. B66C 15/00 318/434
2013/0069088 A1 3/2013 Speck et al.
2013/0153639 A1 6/2013 Hodgkinson et al.
2013/0168435 A1 7/2013 Huang et al.
2013/0175315 A1 7/2013 Milliman
2013/0214025 A1 8/2013 Zemlok et al.
2013/0221065 A1* 8/2013 Aronhalt ............ A61B 17/1155 227/176.1
2013/0261648 A1 10/2013 Laurent et al.
2013/0267950 A1 10/2013 Rosa et al.
2013/0289565 A1 10/2013 Hassler, Jr.
2014/0002322 A1 1/2014 Kanome et al.
2014/0005550 A1 1/2014 Lu et al.
2014/0012289 A1 1/2014 Snow et al.
2014/0060254 A1 3/2014 Macarthur
2014/0069240 A1 3/2014 Dauvin et al.
2014/0088614 A1 3/2014 Blumenkranz

(56) References Cited

U.S. PATENT DOCUMENTS

2014/0088639 A1 3/2014 Bartels et al.
2014/0110453 A1 4/2014 Wingardner et al.
2014/0131419 A1 5/2014 Bettuchi
2014/0148803 A1 5/2014 Taylor
2014/0158390 A1 6/2014 Mashiko et al.
2014/0166727 A1 6/2014 Swayze et al.
2014/0188101 A1 7/2014 Bales, Jr. et al.
2014/0200612 A1 7/2014 Weir et al.
2014/0246476 A1 9/2014 Hall et al.
2014/0263556 A1* 9/2014 Mozdzierz ......... A61B 17/1155 227/176.1
2014/0276776 A1 9/2014 Parihar et al.
2014/0276932 A1 9/2014 Williams et al.
2014/0277017 A1* 9/2014 Leimbach .............. A61B 17/32 227/175.3
2014/0287703 A1 9/2014 Herbsommer et al.
2014/0373003 A1 12/2014 Grez et al.
2015/0022012 A1 1/2015 Kim et al.
2015/0034697 A1 2/2015 Mastri et al.
2015/0053746 A1* 2/2015 Shelton, IV .......... G06F 3/0416 227/177.1
2015/0060516 A1 3/2015 Collings et al.
2015/0067582 A1 3/2015 Donnelly et al.
2015/0076206 A1 3/2015 Sapre
2015/0080883 A1 3/2015 Haverkost et al.
2015/0216605 A1 8/2015 Baldwin
2015/0230861 A1 8/2015 Woloszko et al.
2015/0231771 A1 8/2015 Sakai et al.
2015/0272582 A1 10/2015 Leimbach et al.
2015/0272606 A1 10/2015 Nobis
2015/0280384 A1 10/2015 Leimbach et al.
2015/0280424 A1* 10/2015 Leimbach .............. H02H 3/087 361/18
2015/0282825 A1 10/2015 Trees et al.
2015/0305729 A1 10/2015 Fitzsimmons et al.
2015/0305743 A1 10/2015 Casasanta et al.
2015/0352699 A1 12/2015 Sakai et al.
2016/0030076 A1 2/2016 Faller et al.
2016/0081678 A1 3/2016 Kappel et al.
2016/0089175 A1 3/2016 Hibner et al.
2016/0100839 A1* 4/2016 Marczyk .......... A61B 17/07207 227/176.1
2016/0118201 A1 4/2016 Nicholas et al.
2016/0132026 A1 5/2016 Wingardner et al.
2016/0174969 A1 6/2016 Kerr et al.
2016/0174983 A1 6/2016 Shelton, IV et al.
2016/0175021 A1 6/2016 Hassler, Jr.
2016/0192927 A1 7/2016 Kostrzewski
2016/0207185 A1* 7/2016 Garber .................... B25C 1/008
2016/0256184 A1 9/2016 Shelton, IV et al.
2016/0374669 A1 12/2016 Overmyer et al.
2017/0000549 A1 1/2017 Gilbert et al.
2017/0008156 A1 1/2017 Miyazaki et al.
2017/0020616 A1 1/2017 Vale et al.
2017/0055980 A1 3/2017 Vendely et al.
2017/0056008 A1 3/2017 Shelton, IV et al.
2017/0056016 A1 3/2017 Barton et al.
2017/0056018 A1 3/2017 Zeiner et al.
2017/0086932 A1 3/2017 Auld et al.
2017/0105727 A1 4/2017 Scheib et al.
2017/0105786 A1 4/2017 Scheib et al.
2017/0143336 A1 5/2017 Shah et al.
2017/0168187 A1 6/2017 Calderoni et al.
2017/0181803 A1 6/2017 Mayer-Ullmann et al.
2017/0189018 A1* 7/2017 Harris ................ G01R 31/3842
2017/0202605 A1 7/2017 Shelton, IV et al.
2017/0252060 A1 9/2017 Ellingson et al.
2017/0296183 A1* 10/2017 Shelton, IV ..... A61B 17/07207
2017/0303984 A1 10/2017 Malackowski
2018/0008265 A1 1/2018 Hatanaka et al.
2018/0042610 A1 2/2018 Sgroi, Jr.
2018/0042689 A1 2/2018 Mozdzierz et al.
2018/0049738 A1 2/2018 Meloul et al.
2018/0067004 A1 3/2018 Sgroi, Jr.
2018/0161034 A1 6/2018 Scheib et al.
2018/0231111 A1 8/2018 Mika et al.
2018/0231475 A1 8/2018 Brown et al.
2018/0235617 A1 8/2018 Shelton, IV et al.
2018/0235618 A1 8/2018 Kostrzewski
2018/0235626 A1 8/2018 Shelton, IV et al.
2018/0247711 A1 8/2018 Terry
2018/0250002 A1 9/2018 Eschbach
2018/0280073 A1 10/2018 Sanai et al.
2018/0317915 A1 11/2018 Mcdonald, II
2018/0325514 A1 11/2018 Harris et al.
2018/0360455 A1* 12/2018 Shelton, IV ........... A61B 34/30
2018/0375165 A1 12/2018 Shelton, IV et al.
2019/0000535 A1 1/2019 Messerly et al.
2019/0000536 A1 1/2019 Yates et al.
2019/0006047 A1 1/2019 Gorek et al.
2019/0017311 A1 1/2019 Mcgettrick et al.
2019/0125344 A1 5/2019 Dinardo et al.
2019/0133577 A1 5/2019 Weadock et al.
2019/0142423 A1 5/2019 Satti, III et al.
2019/0200986 A1 7/2019 Shelton, IV et al.
2019/0200987 A1 7/2019 Shelton, IV et al.
2019/0200988 A1 7/2019 Shelton, IV
2019/0200997 A1 7/2019 Shelton, IV et al.
2019/0200998 A1 7/2019 Shelton, IV et al.
2019/0201020 A1 7/2019 Shelton, IV et al.
2019/0201079 A1 7/2019 Shelton, IV et al.
2019/0201158 A1 7/2019 Shelton, IV et al.
2019/0239873 A1 8/2019 Laurent et al.
2019/0247048 A1 8/2019 Gasparovich et al.
2019/0261982 A1 8/2019 Holsten
2019/0262153 A1 8/2019 Tassoni et al.
2019/0298381 A1 10/2019 Kreidler et al.
2019/0314015 A1 10/2019 Shelton, IV et al.
2019/0388091 A1 12/2019 Eschbach et al.
2020/0008827 A1 1/2020 Dearden et al.
2020/0015817 A1 1/2020 Harris et al.
2020/0030020 A1 1/2020 Wang et al.
2020/0037939 A1 2/2020 Castagna et al.
2020/0046355 A1 2/2020 Harris et al.
2020/0046356 A1 2/2020 Baxter, III et al.
2020/0054320 A1 2/2020 Harris et al.
2020/0054329 A1 2/2020 Shelton, IV et al.
2020/0061385 A1 2/2020 Schwarz et al.
2020/0114505 A1 4/2020 Kikuchi
2020/0205810 A1 7/2020 Posey et al.
2020/0205823 A1 7/2020 Vendely et al.
2020/0289119 A1 9/2020 Viola et al.
2020/0315623 A1 10/2020 Eisinger et al.
2020/0323531 A1* 10/2020 Milliman ........... A61B 17/1155
2020/0345349 A1 11/2020 Kimball et al.
2020/0345356 A1 11/2020 Leimbach et al.
2020/0345363 A1 11/2020 Shelton, IV et al.
2020/0375674 A1 12/2020 Overmyer et al.
2020/0397430 A1 12/2020 Patel et al.
2020/0405304 A1 12/2020 Mozdzierz et al.
2020/0405403 A1 12/2020 Shelton, IV et al.
2020/0405404 A1 12/2020 Shelton, IV et al.
2021/0007742 A1* 1/2021 Rector ............... A61B 17/0644
2021/0045742 A1* 2/2021 Shelton, IV ........... A61B 90/06
2021/0128153 A1 5/2021 Sgroi
2021/0153866 A1 5/2021 Knapp et al.
2021/0177401 A1 6/2021 Abramek et al.
2021/0177411 A1 6/2021 Williams
2021/0204951 A1 7/2021 Sgroi et al.
2021/0212671 A1 7/2021 Ramadan et al.
2021/0275175 A1 9/2021 Vadali et al.
2021/0307744 A1 10/2021 Walcott et al.
2021/0338260 A1 11/2021 Le Rolland et al.
2021/0369273 A1* 12/2021 Yates .............. A61B 17/07207
2022/0000479 A1 1/2022 Shelton, IV et al.
2022/0015760 A1 1/2022 Beardsley et al.
2022/0049593 A1 2/2022 Groover et al.
2022/0054125 A1 2/2022 Ji et al.
2022/0079580 A1 3/2022 Vendely et al.
2022/0079586 A1 3/2022 Shelton, IV et al.
2022/0104816 A1 4/2022 Fernandes et al.
2022/0104820 A1 4/2022 Shelton, IV et al.
2022/0117602 A1 4/2022 Wise et al.

(56) References Cited

U.S. PATENT DOCUMENTS

| | | | |
|---|---|---|---|
| 2022/0133299 | A1 | 5/2022 | Baxter, III |
| 2022/0133300 | A1 | 5/2022 | Leimbach et al. |
| 2022/0133301 | A1 | 5/2022 | Leimbach |
| 2022/0133302 | A1 | 5/2022 | Zerkle et al. |
| 2022/0133303 | A1 | 5/2022 | Huang |
| 2022/0133304 | A1 | 5/2022 | Leimbach et al. |
| 2022/0133310 | A1 | 5/2022 | Ross |
| 2022/0133311 | A1 | 5/2022 | Huang |
| 2022/0133312 | A1 | 5/2022 | Huang |
| 2022/0133427 | A1 | 5/2022 | Baxter, III |
| 2022/0133428 | A1 | 5/2022 | Leimbach et al. |
| 2022/0142643 | A1 | 5/2022 | Shelton, IV et al. |
| 2022/0151611 | A1 | 5/2022 | Shelton, IV et al. |
| 2022/0151613 | A1 | 5/2022 | Vendely et al. |
| 2022/0151614 | A1 | 5/2022 | Vendely et al. |
| 2022/0151615 | A1 | 5/2022 | Shelton, IV et al. |
| 2022/0151616 | A1 | 5/2022 | Shelton, IV et al. |
| 2022/0160358 | A1 | 5/2022 | Vvixey |
| 2022/0167968 | A1 | 6/2022 | Worthington et al. |
| 2022/0167970 | A1 | 6/2022 | Aronhalt et al. |
| 2022/0167971 | A1 | 6/2022 | Shelton, IV et al. |
| 2022/0167972 | A1 | 6/2022 | Shelton, IV et al. |
| 2022/0167973 | A1 | 6/2022 | Shelton, IV et al. |
| 2022/0167974 | A1 | 6/2022 | Shelton, IV et al. |
| 2022/0167975 | A1 | 6/2022 | Shelton, IV et al. |
| 2022/0167977 | A1 | 6/2022 | Shelton, IV et al. |
| 2022/0167979 | A1 | 6/2022 | Yates et al. |
| 2022/0167980 | A1 | 6/2022 | Shelton, IV et al. |
| 2022/0167981 | A1 | 6/2022 | Shelton, IV et al. |
| 2022/0167982 | A1 | 6/2022 | Shelton, IV et al. |
| 2022/0167983 | A1 | 6/2022 | Shelton, IV et al. |
| 2022/0167984 | A1 | 6/2022 | Shelton, IV et al. |
| 2022/0167995 | A1 | 6/2022 | Parfett et al. |
| 2022/0168038 | A1 | 6/2022 | Shelton, IV et al. |
| 2022/0175370 | A1 | 6/2022 | Shelton, IV et al. |
| 2022/0175371 | A1 | 6/2022 | Hess et al. |
| 2022/0175372 | A1 | 6/2022 | Shelton, IV et al. |
| 2022/0175375 | A1 | 6/2022 | Harris et al. |
| 2022/0175378 | A1 | 6/2022 | Leimbach et al. |
| 2022/0175381 | A1 | 6/2022 | Scheib et al. |
| 2022/0183685 | A1 | 6/2022 | Shelton, IV et al. |
| 2022/0192667 | A1 | 6/2022 | Shelton, IV et al. |
| 2022/0211367 | A1 | 7/2022 | Schmid et al. |
| 2022/0218332 | A1 | 7/2022 | Shelton, IV et al. |
| 2022/0218333 | A1 | 7/2022 | Parihar et al. |
| 2022/0218334 | A1 | 7/2022 | Parihar et al. |
| 2022/0218336 | A1 | 7/2022 | Timm et al. |
| 2022/0218337 | A1 | 7/2022 | Timm et al. |
| 2022/0218338 | A1 | 7/2022 | Shelton, IV et al. |
| 2022/0218340 | A1 | 7/2022 | Harris et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218347 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218378 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225980 | A1 | 7/2022 | Shelton, IV et al. |
| 2022/0225982 | A1 | 7/2022 | Yates et al. |
| 2022/0225986 | A1 | 7/2022 | Shelton, IV et al. |
| 2022/0225992 | A1 | 7/2022 | Smith et al. |
| 2022/0225993 | A1 | 7/2022 | Huitema et al. |
| 2022/0225994 | A1 | 7/2022 | Setser et al. |
| 2022/0226012 | A1 | 7/2022 | Shelton, IV et al. |
| 2022/0226013 | A1 | 7/2022 | Hall et al. |
| 2022/0233184 | A1 | 7/2022 | Parihar et al. |
| 2022/0233185 | A1 | 7/2022 | Parihar et al. |
| 2022/0233186 | A1 | 7/2022 | Timm et al. |
| 2022/0233187 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0249095 | A1 | 8/2022 | Shelton, IV et al. |
| 2022/0265272 | A1 | 8/2022 | Li et al. |
| 2022/0273291 | A1 | 9/2022 | Shelton, IV et al. |
| 2022/0273292 | A1 | 9/2022 | Shelton, IV et al. |
| 2022/0273293 | A1 | 9/2022 | Shelton, IV et al. |
| 2022/0273294 | A1 | 9/2022 | Creamer et al. |
| 2022/0273299 | A1 | 9/2022 | Shelton, IV et al. |
| 2022/0273300 | A1 | 9/2022 | Shelton, IV et al. |
| 2022/0273301 | A1 | 9/2022 | Creamer et al. |
| 2022/0273302 | A1 | 9/2022 | Shelton, IV et al. |
| 2022/0273303 | A1 | 9/2022 | Creamer et al. |
| 2022/0273304 | A1 | 9/2022 | Shelton, IV et al. |
| 2022/0273305 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0278438 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296235 | A1 | 9/2022 | Morgan et al. |
| 2022/0296236 | A1 | 9/2022 | Bakos et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378420 | A1 | 12/2022 | Leimbach et al. |
| 2022/0378424 | A1 | 12/2022 | Huang et al. |
| 2022/0378425 | A1 * | 12/2022 | Huang ................. A61B 17/072 |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |

(56) References Cited

U.S. PATENT DOCUMENTS

| | | | | | |
|---|---|---|---|---|---|
| 2023/0051271 | A1 * | 2/2023 | Shelton, IV | ..... | A61B 17/07207 |
| 2023/0293170 | A1 * | 9/2023 | Shelton, IV | ......... | A61B 17/068 227/175.1 |

FOREIGN PATENT DOCUMENTS

| | | | | |
|---|---|---|---|---|
| AU | 2013235553 | A1 | 9/2014 | |
| CA | 2762156 | A1 | 4/2001 | |
| CA | 2576347 | A1 | 7/2007 | |
| CA | 2765623 | A1 | 8/2012 | |
| CN | 103764045 | A | 4/2014 | |
| CN | 104921730 | B | 9/2017 | |
| DE | 69722540 | T2 | 4/2004 | |
| EP | 0516544 | B1 | 3/1996 | |
| EP | 2153793 | A2 | 2/2010 | |
| EP | 2283780 | A2 | 2/2011 | |
| EP | 2529671 | A2 | 12/2012 | |
| EP | 2764834 | A2 * | 8/2014 | ....... A61B 17/07207 |
| EP | 3235445 | A1 | 10/2017 | |
| EP | 3476301 | A1 | 5/2019 | |
| EP | 3505095 | A1 | 7/2019 | |
| EP | 3791810 | A1 | 3/2021 | |
| JP | S6333137 | A | 2/1988 | |
| JP | H0489041 | A | 3/1992 | |
| JP | H0636757 | A | 2/1994 | |
| JP | H0950795 | A | 2/1997 | |
| JP | 1433631 | S | 2/2012 | |
| JP | 2020501797 | A | 1/2020 | |
| WO | 0036690 | A2 | 6/2000 | |
| WO | 2017138905 | A1 | 8/2017 | |
| WO | 2018011664 | A1 | 1/2018 | |
| WO | 2019130087 | A1 | 7/2019 | |
| WO | 2019130089 | A1 | 7/2019 | |
| WO | 2019208902 | A1 | 10/2019 | |
| WO | 2021189234 | A1 | 9/2021 | |

OTHER PUBLICATIONS

U.S. Appl. No. 62/798,651, filed Jan. 30, 2019.

U.S. Appl. No. 62/840,602, filed Apr. 30, 2019.

Arjo Loeve et al., Scopes Too Flexible . . . and Too Stiff, 2010, IEEE Pulse, Nov./Dec. 2010 (Year: 2010), 16 pages.

Molina, "Low Level Reader Protocol (LLRP)," Oct. 13, 2010, pp. 1-198.

* cited by examiner 1920
1922
1928
1926
1934
1610″
1932
1905
1940
1938
1902
1900
1904
1910
1908
1906
1912

1920
1922
1900
1905
1928
1926
1934
1932
1906
1940
1938
1908
1904
1910
1912

1610″

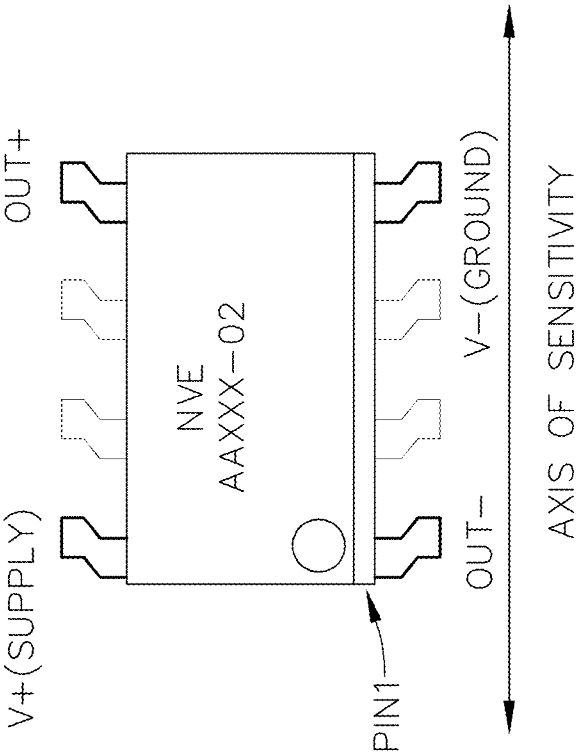
FIG. 68A
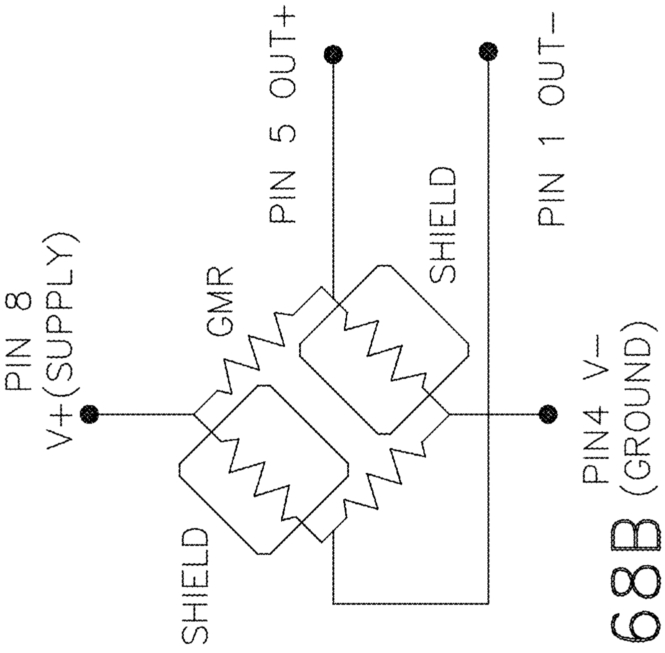
FIG. 68B
| PART NUMBER | SATURATION FIELD ($Oe^1$) | LINEAR RANGE (\|$Oe^1$\|) | | SENSITIVITY (mV/V−$Oe^1$) | | RESISTANCE (Ohms) | PACKAGE[2] | DIE SIZE[3] (μm) |
|---|---|---|---|---|---|---|---|---|
| | | Min | Max | Min | Max | | | |
| AAL002−02 | 15 | 1.5 | 10.5 | 3.0 | 4.2 | 5.5K±20% | SOIC8 | 436x3370 |
FIG. 68C

FEEDBACK ALGORITHMS FOR MANUAL BAILOUT SYSTEMS FOR SURGICAL INSTRUMENTS

CROSS-REFERENCE TO RELATED APPLICATIONS

This application is a continuation application claiming priority under 35 U.S.C. § 120 to U.S. patent application Ser. No. 16/587,803, entitled FEEDBACK ALGORITHMS FOR MANUAL BAILOUT SYSTEMS FOR SURGICAL INSTRUMENTS, filed Sep. 30, 2019, now U.S. Patent Application Publication No. 2020/0093506, which is a continuation application claiming priority under 35 U.S.C. § 120 to U.S. patent application Ser. No. 16/041,145, entitled FEEDBACK ALGORITHMS FOR MANUAL BAILOUT SYSTEMS FOR SURGICAL INSTRUMENTS, filed Jul. 20, 2018, now U.S. Patent Application Publication No. 2018/0333169, which is a continuation application claiming priority under 35 U.S.C. § 120 to U.S. patent application Ser. No. 14/226,093, entitled FEEDBACK ALGORITHMS FOR MANUAL BAILOUT SYSTEMS FOR SURGICAL INSTRUMENTS, filed Mar. 26, 2014, which issued on Jul. 24, 2018 as U.S. Pat. No. 10,028,761, the entire disclosures of which are hereby incorporated by reference herein.

BACKGROUND

The present invention relates to surgical instruments and, in various circumstances, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 33, which is divided into

FIG. 68A is a schematic depicting an integrated circuit according to various embodiments of the present disclosure;

FIG. 68B is a schematic depicting a magnetoresistive circuit according to various embodiments of the present disclosure; and FIG. 68C is a table listing various specifications of a magnetoresistive sensor according to various embodiments of the present disclosure.

DETAILED DESCRIPTION

Figure 1:
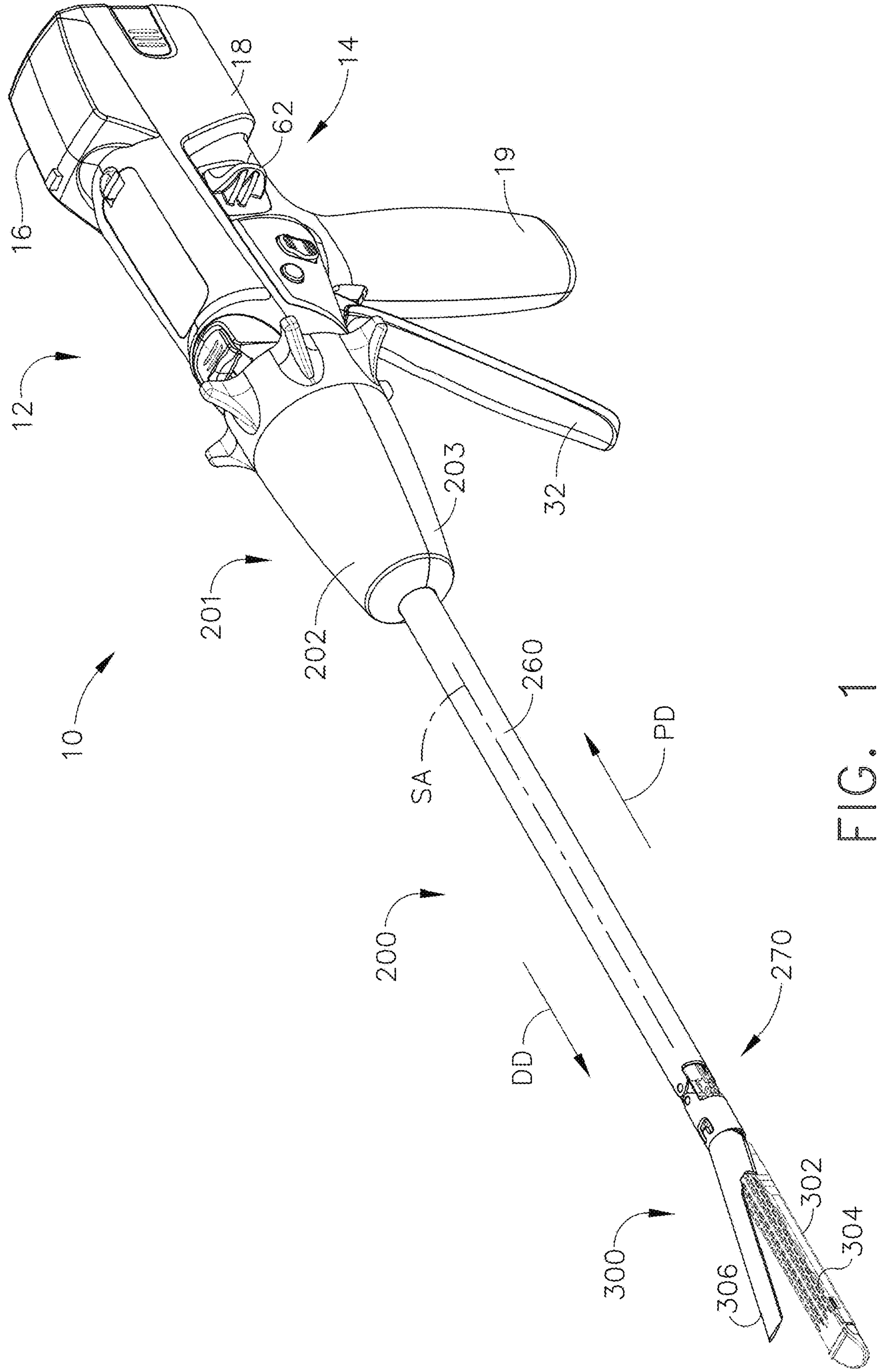
FIG. 1 is a perspective view of a surgical instrument that has an interchangeable shaft assembly operably coupled thereto.

Applicant of the present application owns the following patent applications that were filed on Mar. 1, 2013 and which are each herein incorporated by reference in their respective entireties:

- U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;
- U.S. patent application Ser. No. 13/782,323, entitled ROTARY POWERED ARTICULATION JOINTS FOR SURGICAL INSTRUMENTS, now U.S. Pat. No. 9,782,169;
- U.S. patent application Ser. No. 13/782,338, entitled THUMBWHEEL SWITCH ARRANGEMENTS FOR SURGICAL INSTRUMENTS, now U.S. Patent Application Publication No. 2014/0249557;
- U.S. patent application Ser. No. 13/782,499, entitled ELECTROMECHANICAL SURGICAL DEVICE WITH SIGNAL RELAY ARRANGEMENT, now U.S. Pat. No. 9,358,033;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986, are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent applications that were filed on Mar. 26, 2014 and are each herein incorporated by reference in their respective entireties:

U.S. patent application Ser. No. 14/226,142, entitled SURGICAL INSTRUMENT COMPRISING A SENSOR SYSTEM, now U.S. Pat. No. 9,913,642;

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated embodiment, the instrument 10 includes a housing 12 that comprises a handle 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

Figure 2:
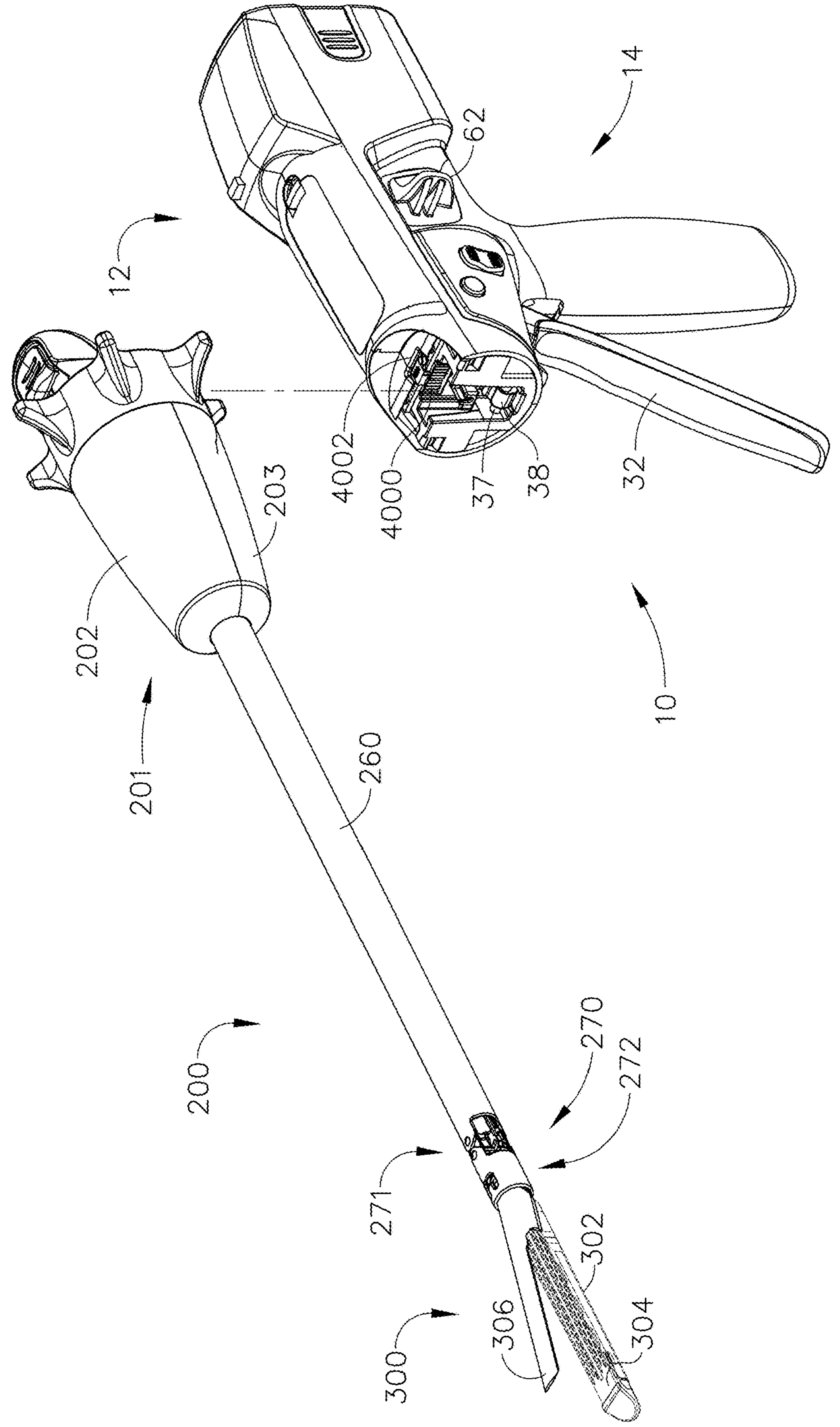
FIG. 2 is an exploded assembly view of the interchangeable shaft assembly and surgical instrument of FIG. 1.
Figure 3:
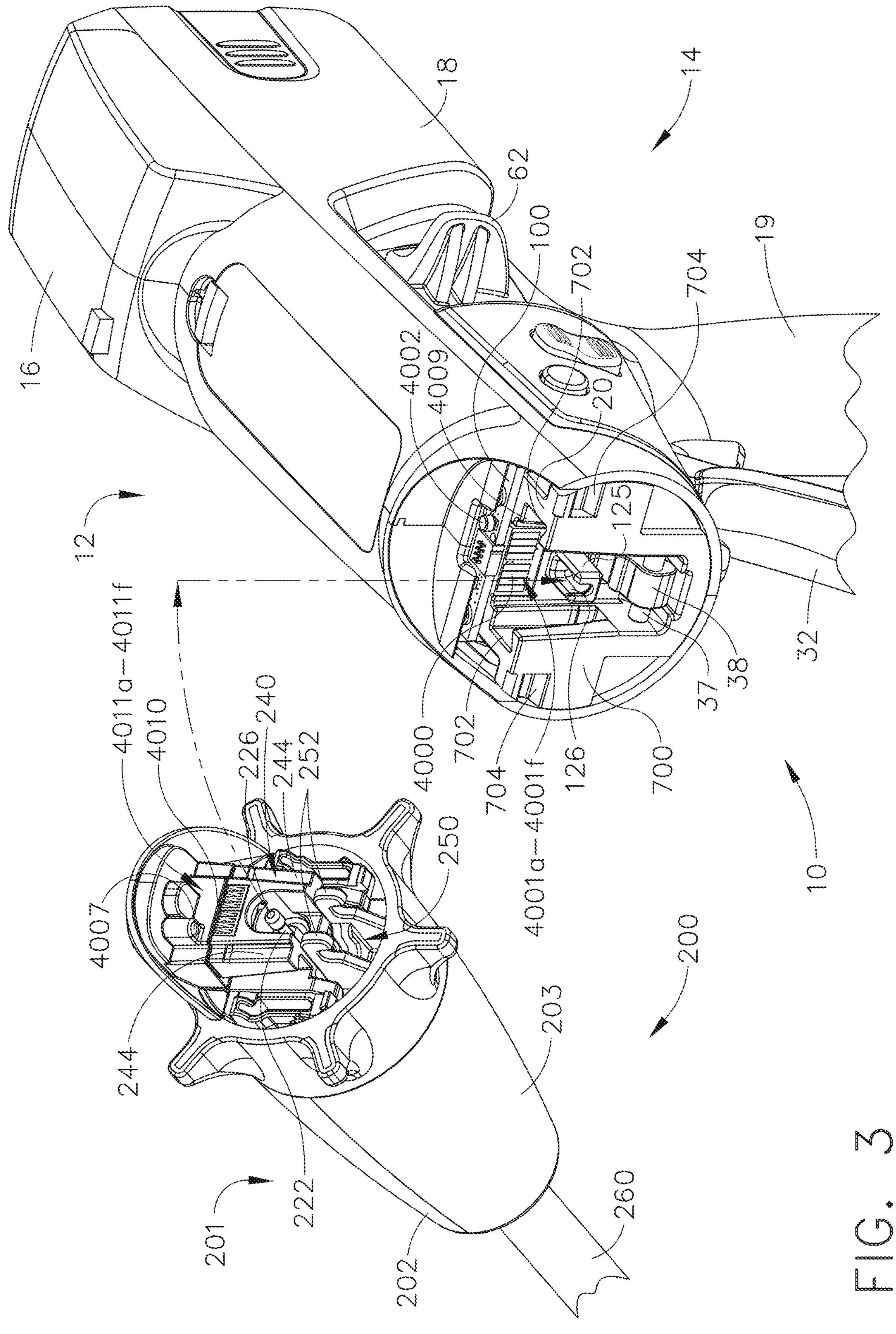
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
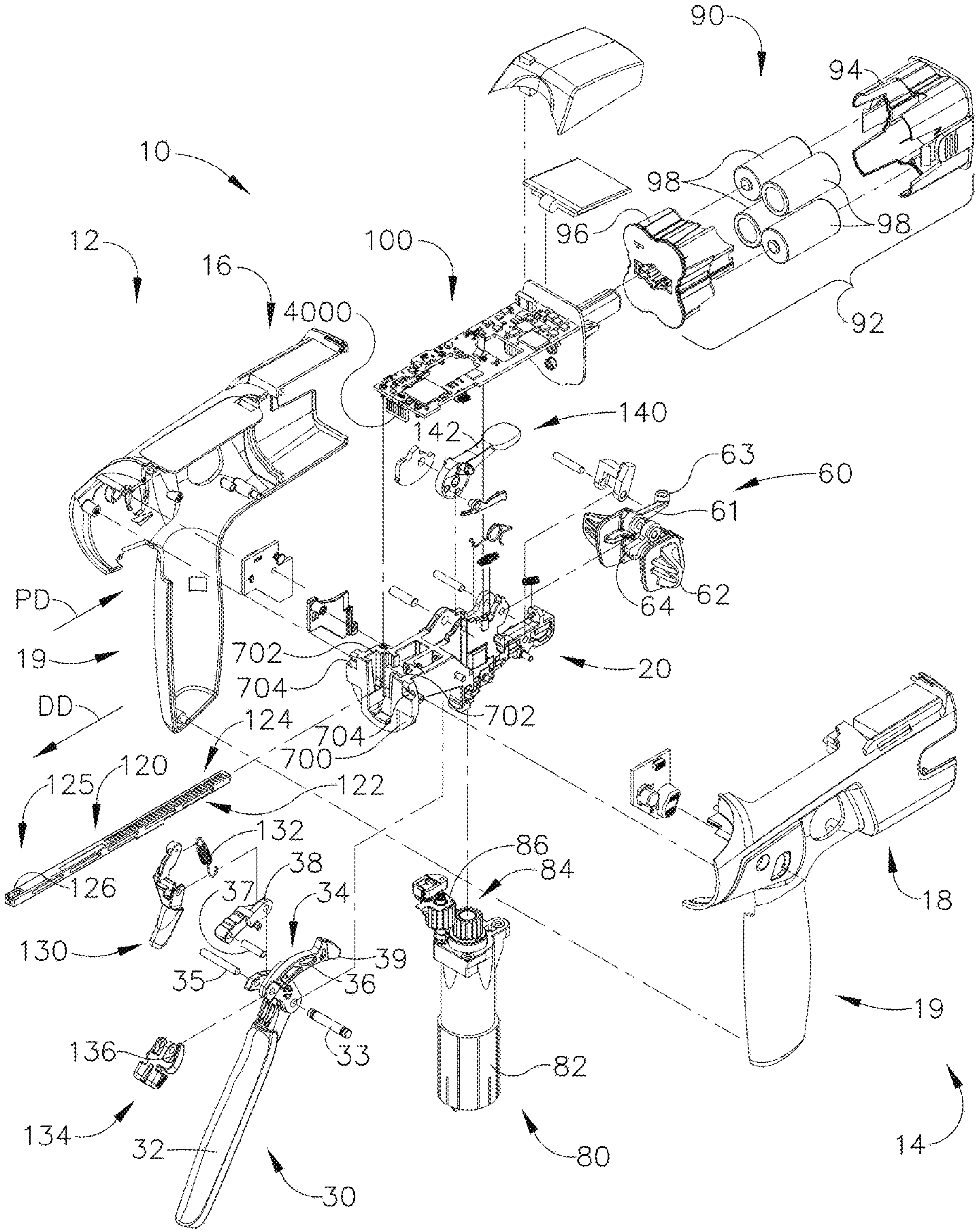
FIG. 4 is an exploded assembly view of a portion of the surgical instrument of FIGS. 1-3.
Figure 5:
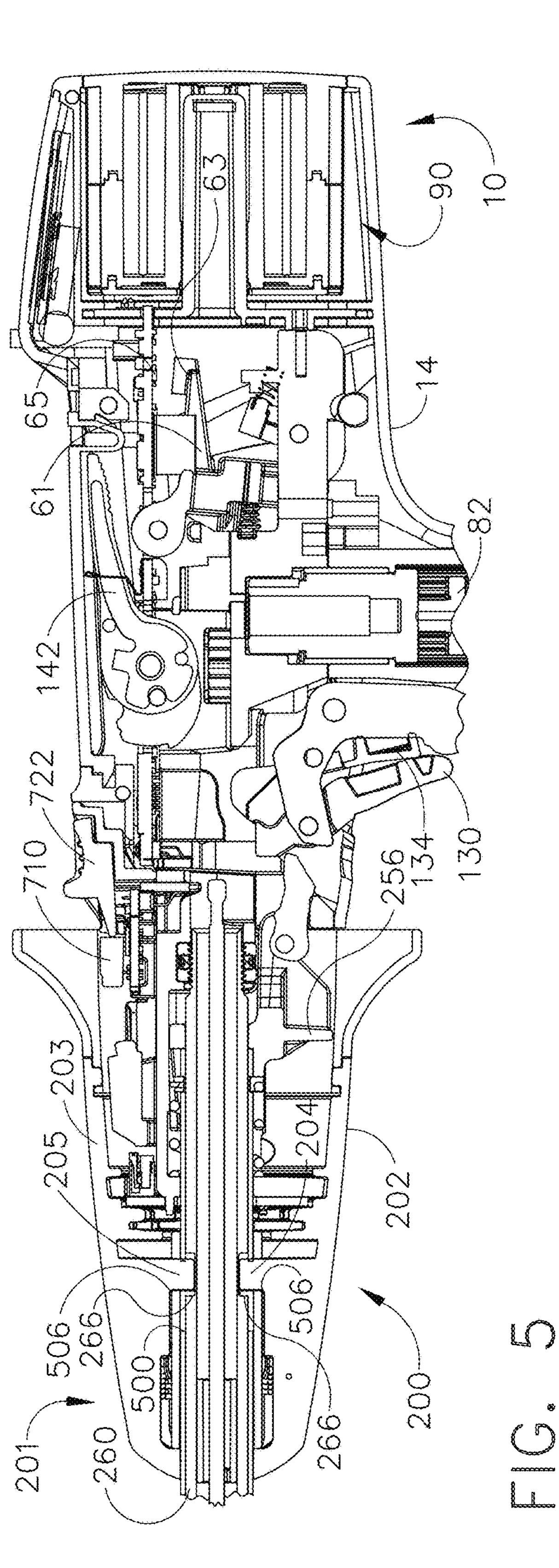
FIG. 5 is a cross-sectional side view of a portion of the surgical instrument of FIG. 4 with the firing trigger in a fully actuated position.
Figure 6:
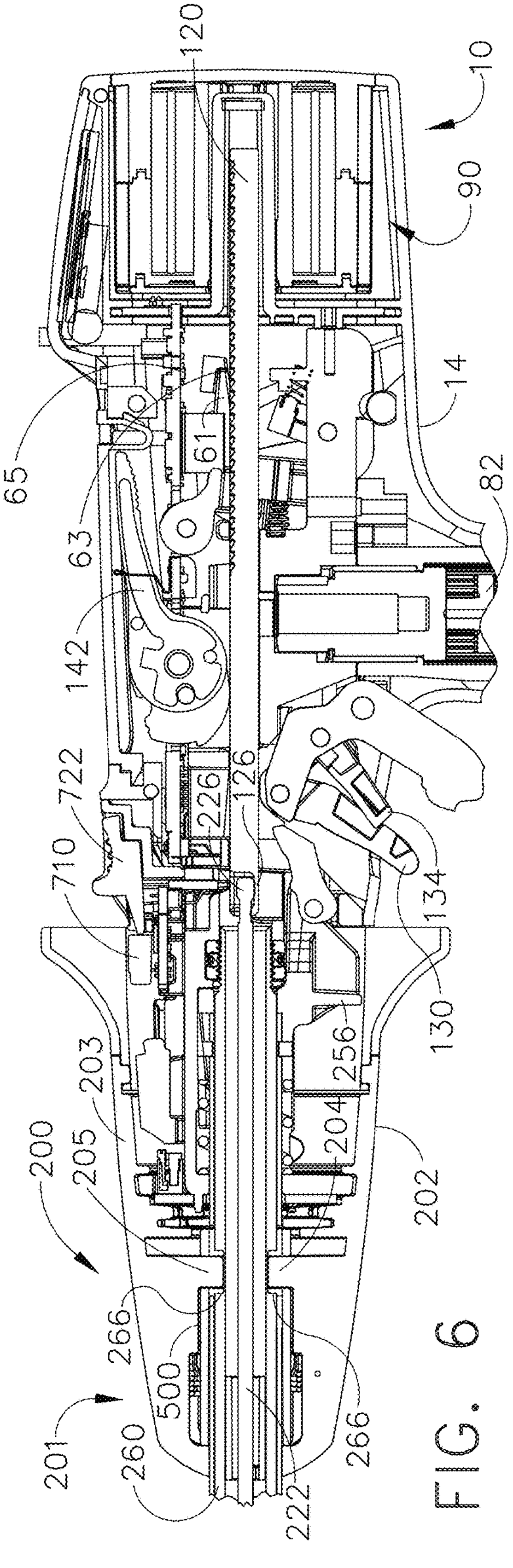
FIG. 6 is another cross-sectional view of a portion of the surgical instrument of FIG. 5 with the firing trigger in an unactuated position.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle 14. As can be seen in FIG. 4, the handle 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports a plurality of drive systems therein that are configured to generate and apply various control motions to corresponding portions of the interchangeable shaft assembly that is operably attached thereto.

Referring now to FIG. 4, the handle 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As can be seen in FIG. 4, the closure linkage assembly 34 may include a first closure link 36 and a second closure link 38 that are pivotally coupled to the closure trigger 32 by a pin 35. The second closure link 38 may also be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements may also be employed.

Figure 13:
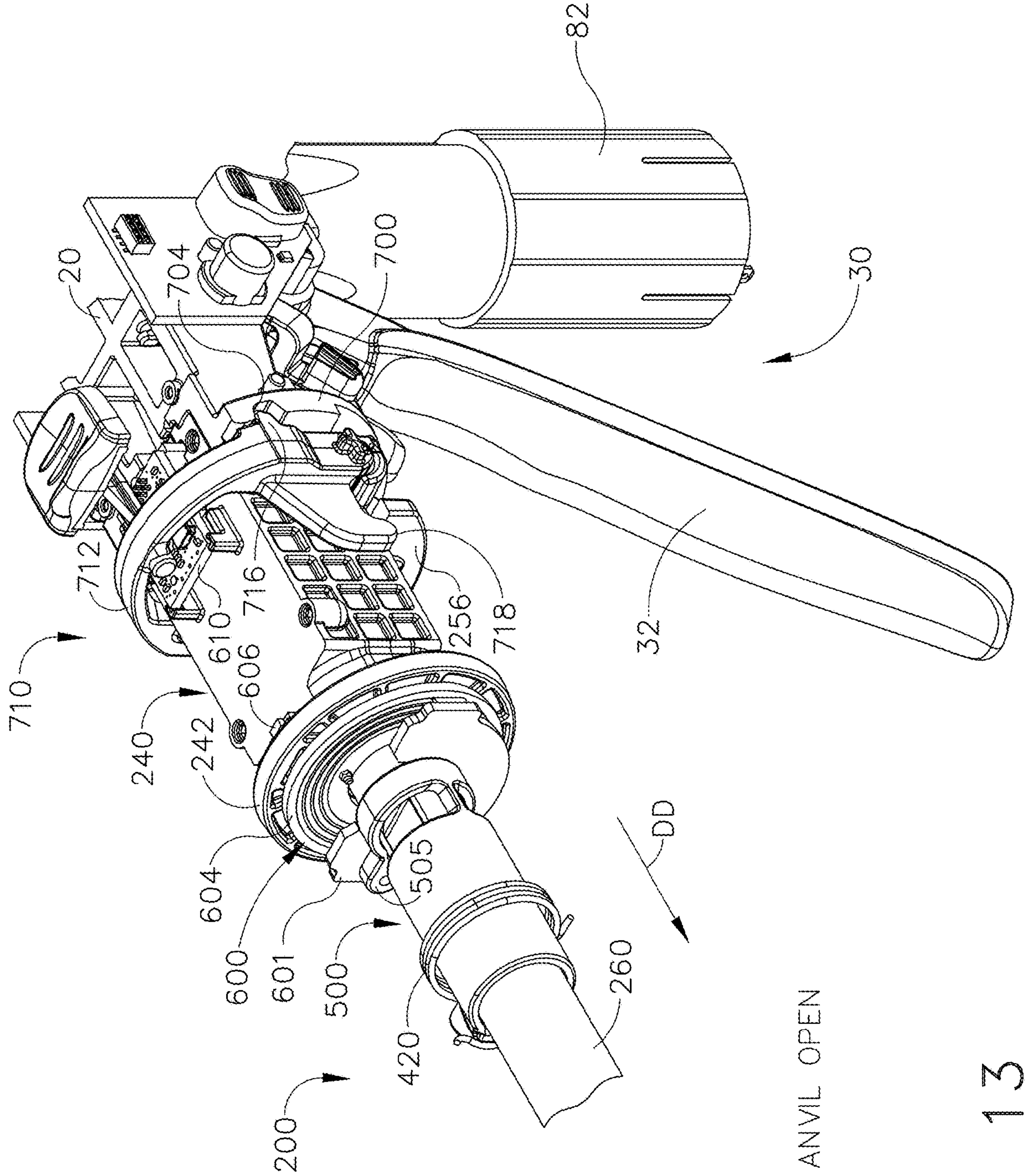
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
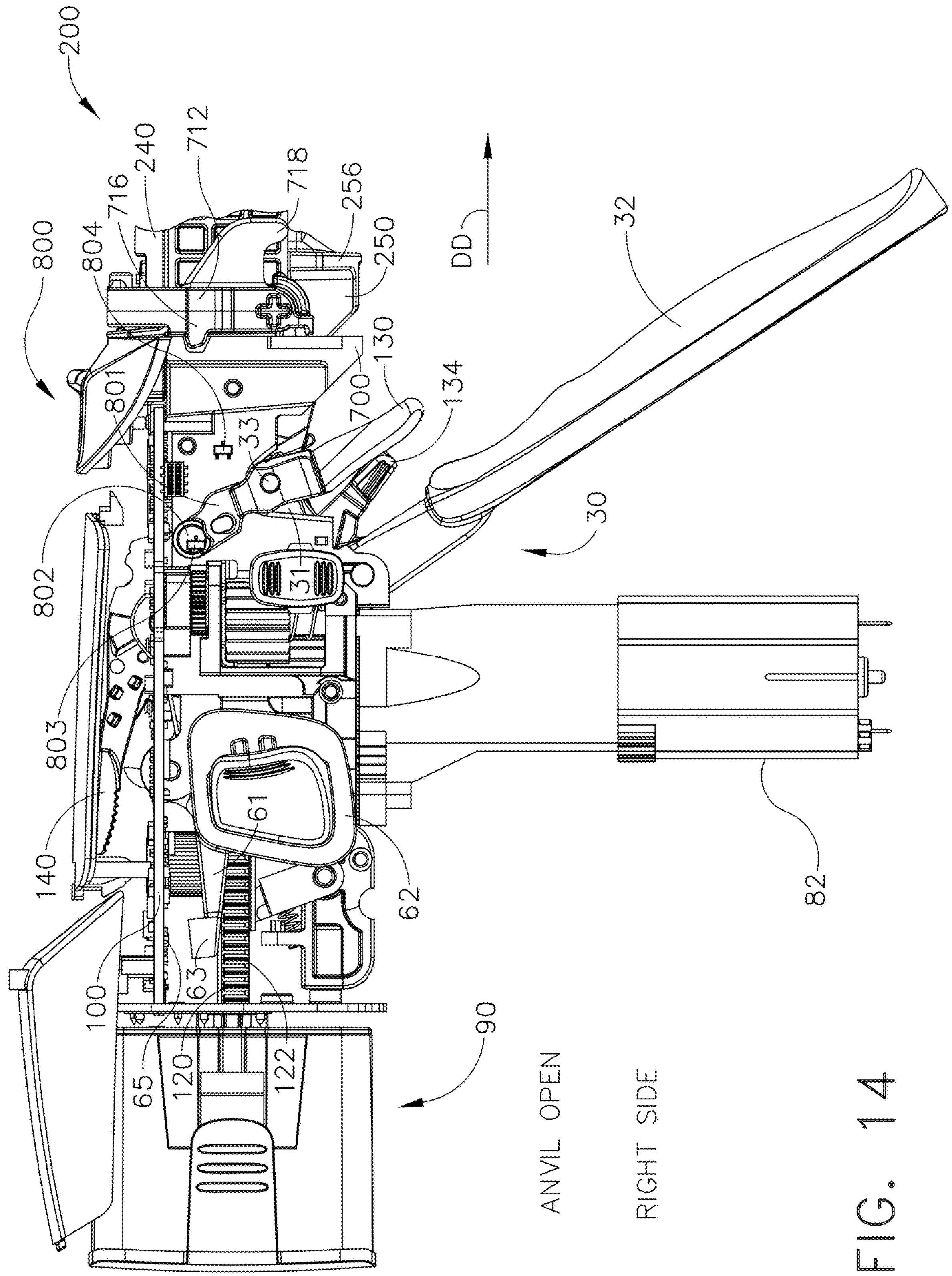
FIG. 14 is a right side elevational view of the interchangeable shaft assembly and surgical instrument of FIG. 13.
Figure 15:
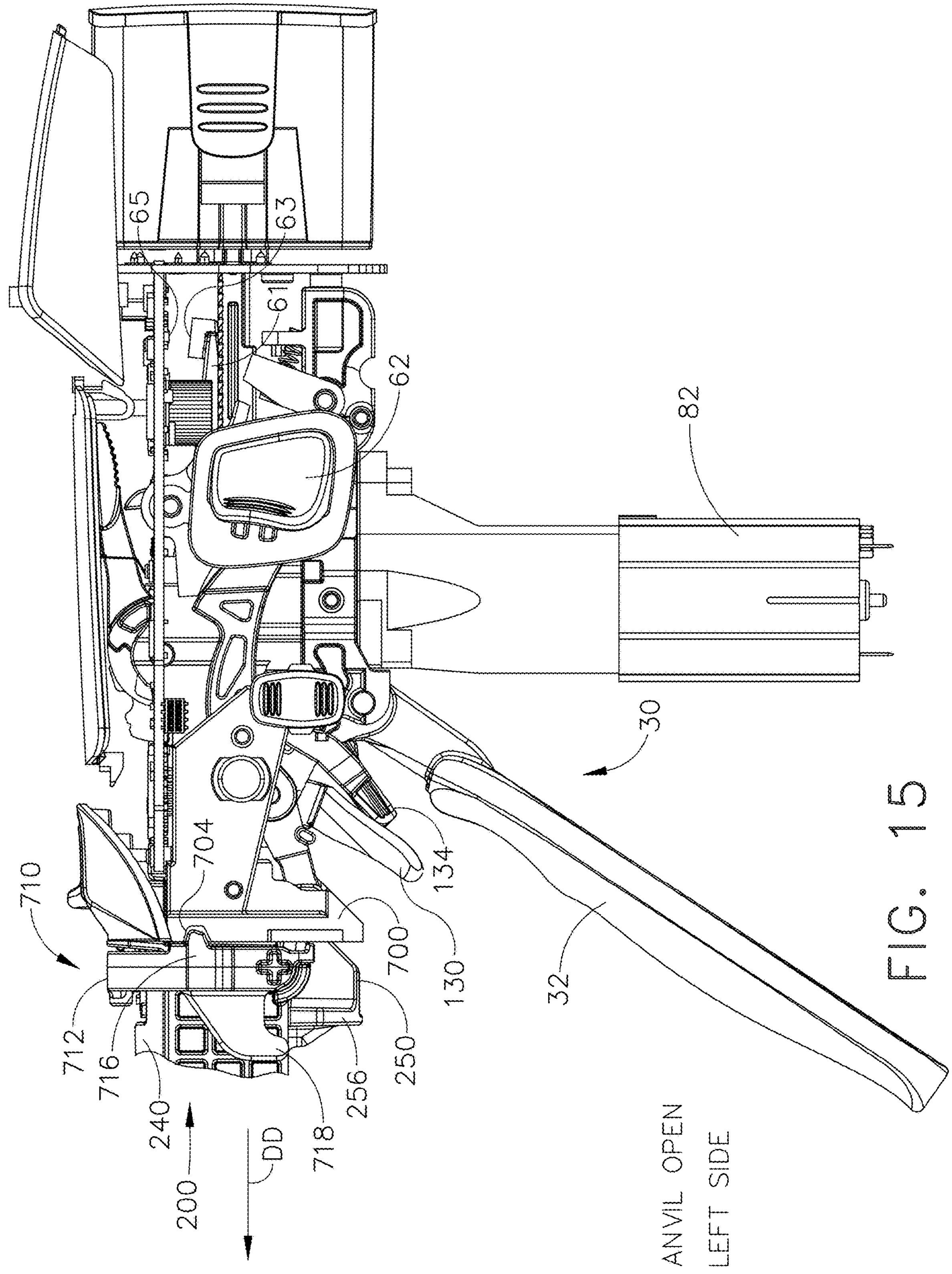
FIG. 15 is a left side elevational view of the interchangeable shaft assembly and surgical instrument of FIGS. 13 and 14.
Figure 16:
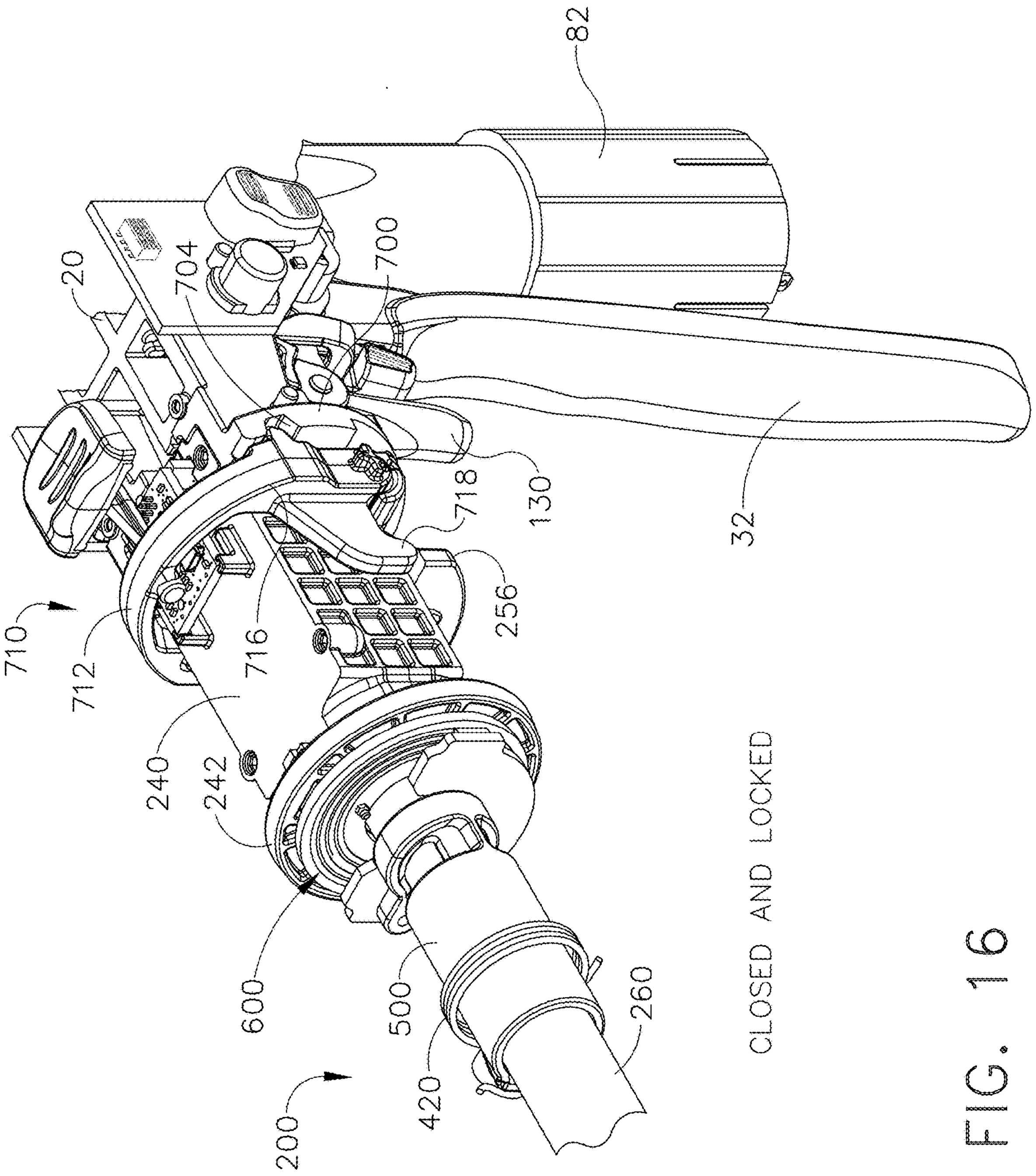
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
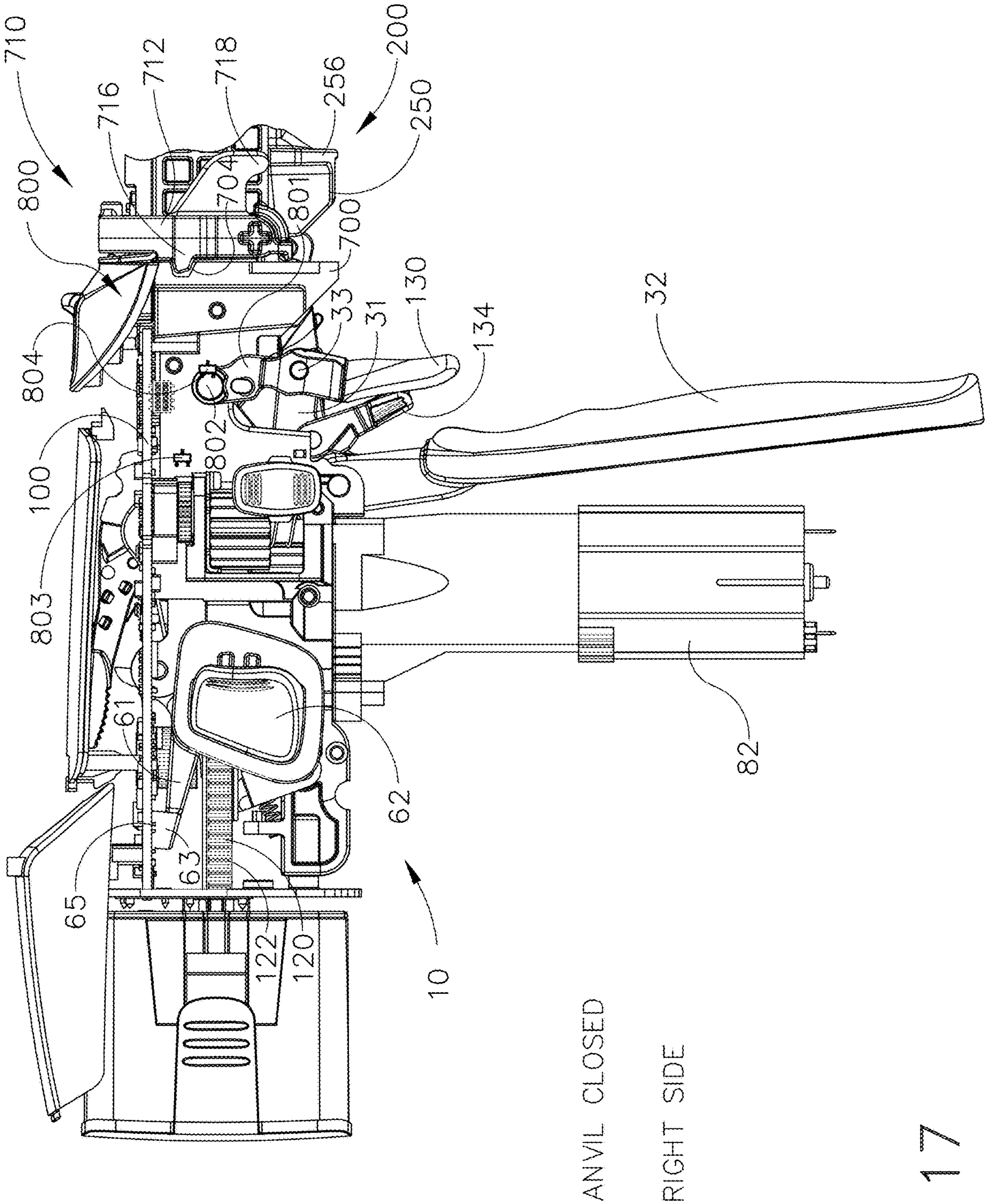
FIG. 17 is a right side elevational view of the interchangeable shaft assembly and surgical instrument of FIG. 16.
Figure 18:
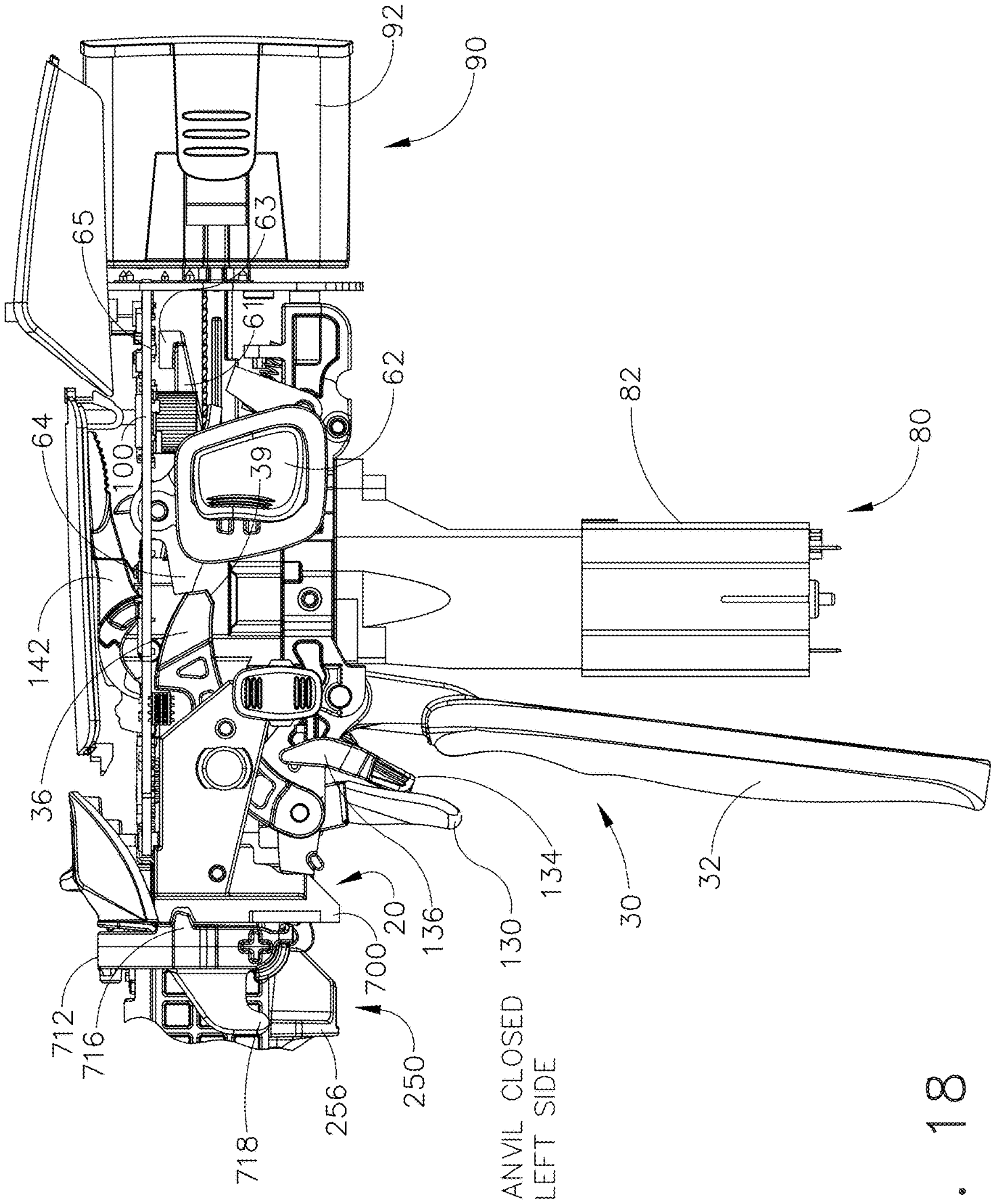
FIG. 18 is a left side elevational view of the interchangeable shaft assembly and surgical instrument of FIGS. 16 and 17.
Figure 18A:
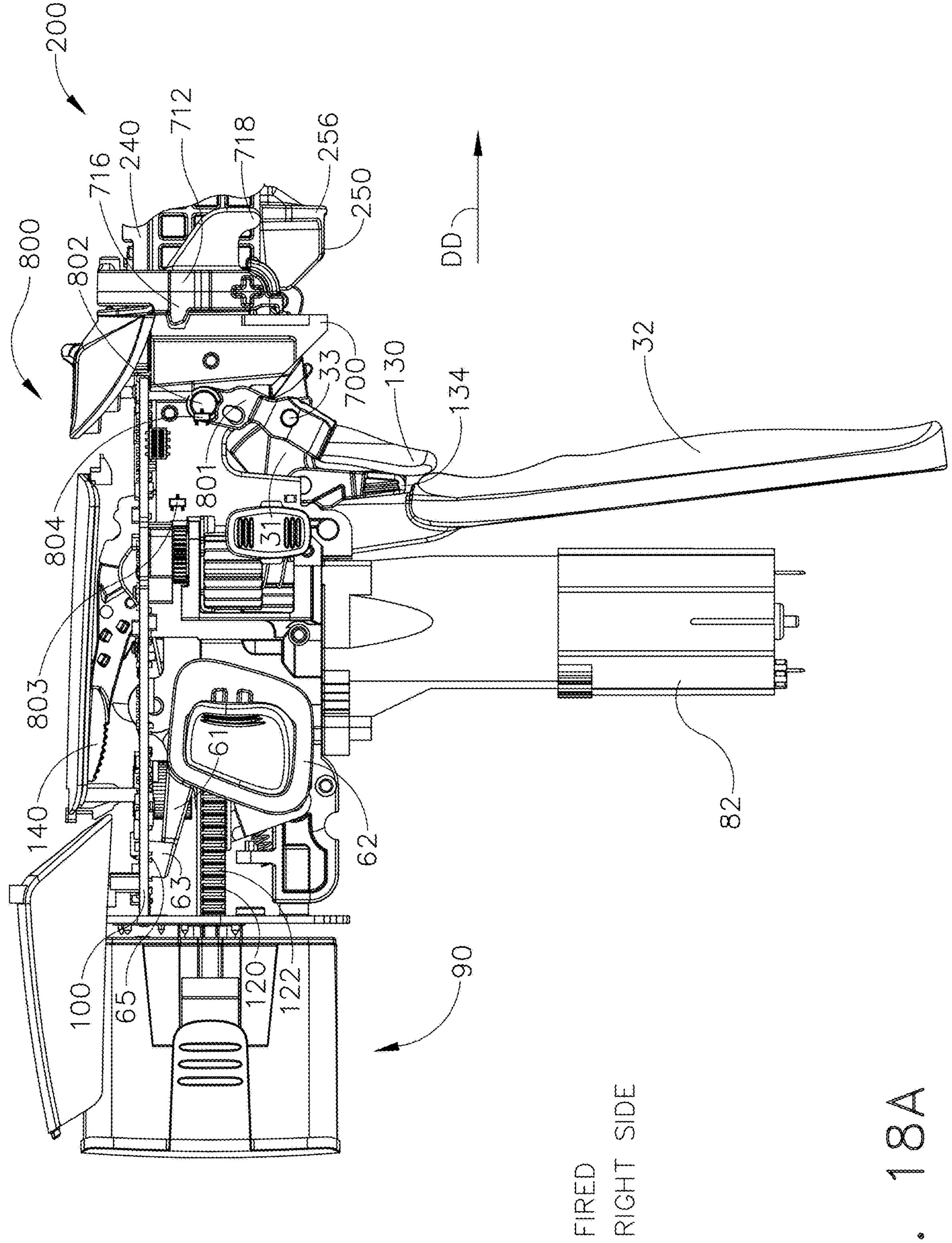
FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position.
Figure 19:
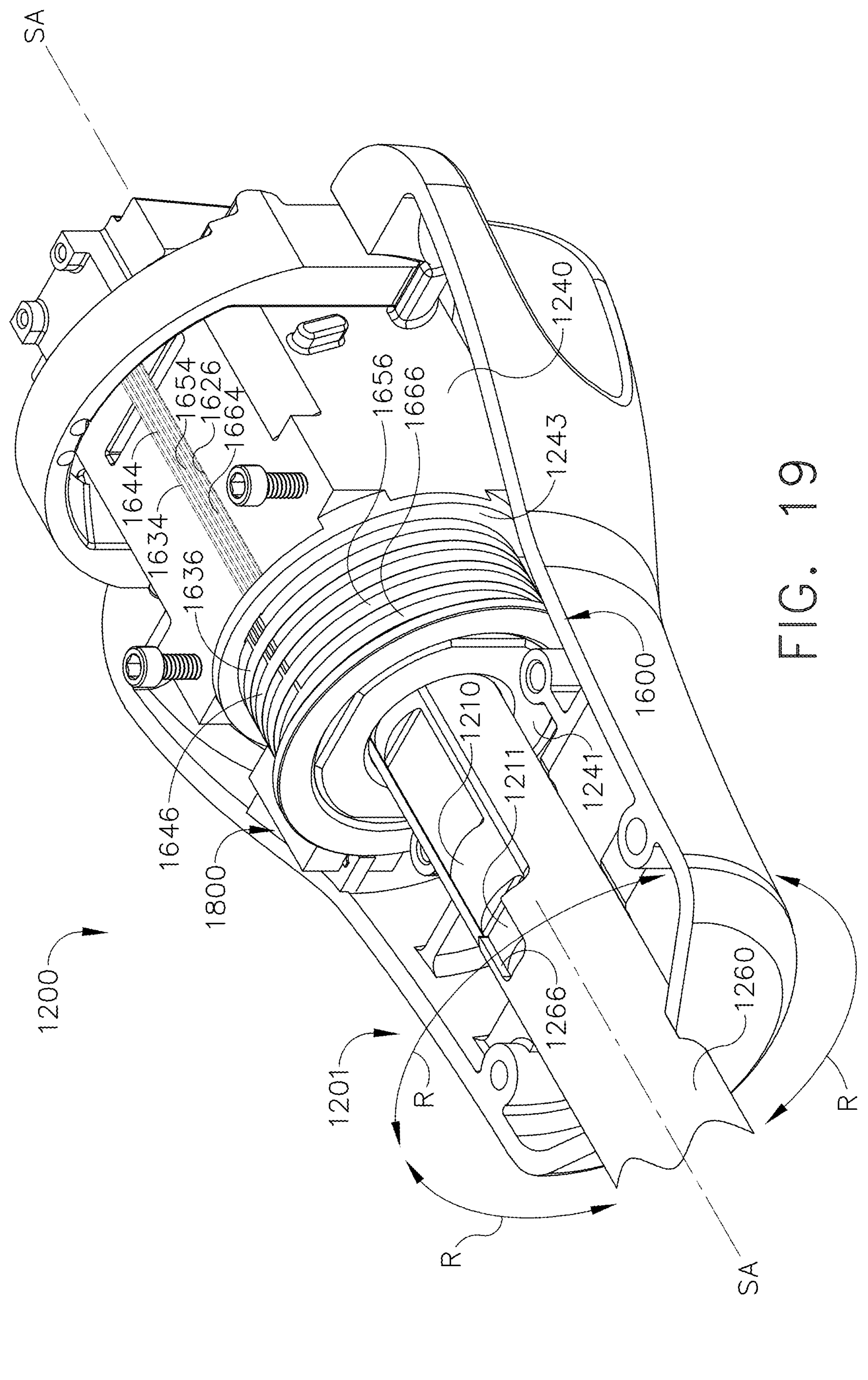
FIG. 19 is a perspective view of a portion of an interchangeable shaft assembly showing an electrical coupler arrangement.
Figure 20:
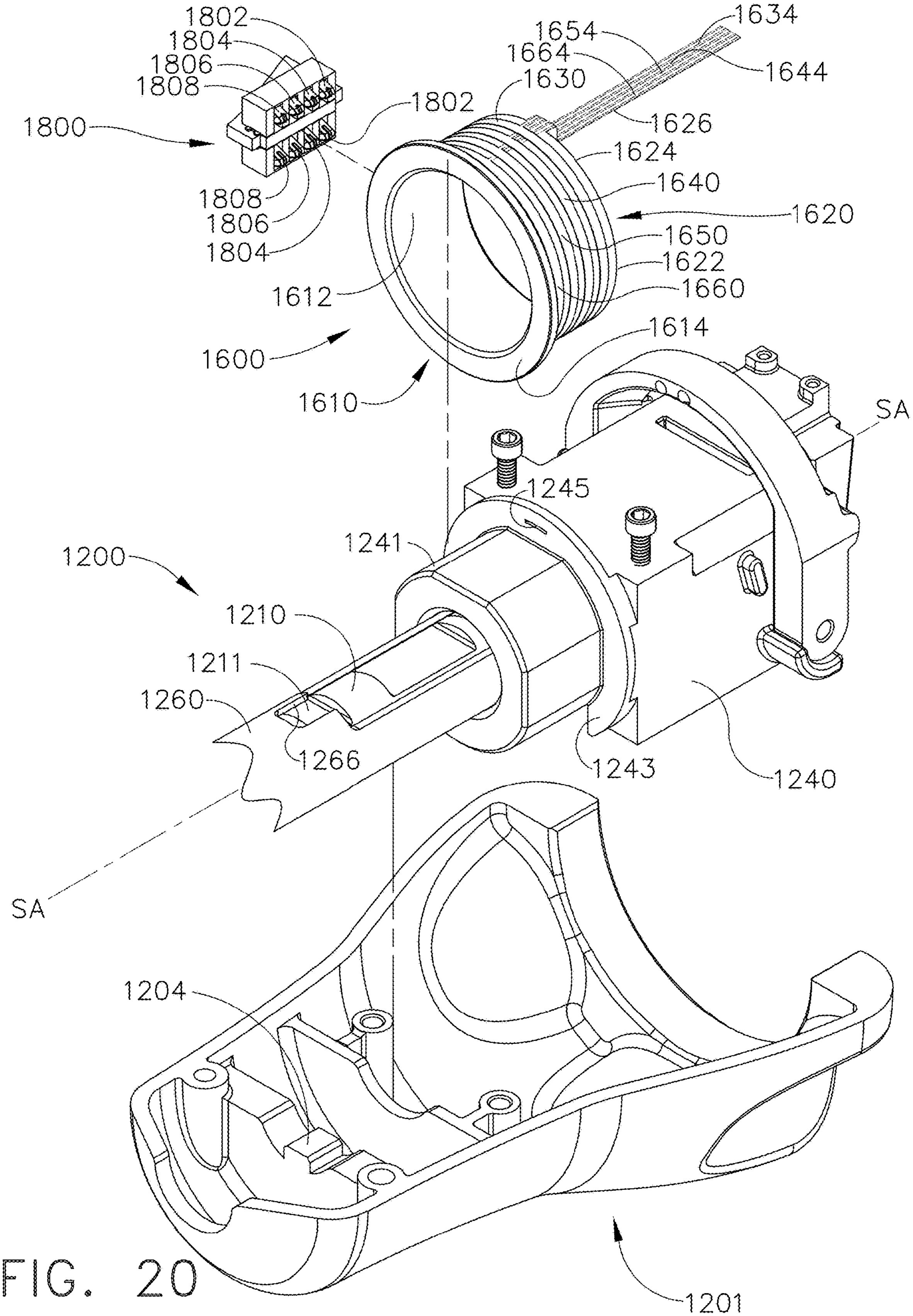
FIG. 20 is an exploded assembly view of portions of the interchangeable shaft assembly and electrical coupler of FIG. 19.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one embodiment, a Hall effect sensor 65, for example, can be mounted to the bottom surface of the circuit board 100. The Hall effect sensor 65 can be configured to detect changes in a magnetic field surrounding the Hall effect sensor 65 caused by the movement of the magnetic element 63. The Hall effect sensor 65 can be in signal communication with a microcontroller 7004 (FIG. 59), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

In at least one form, the handle 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As can be seen in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle 14 can include a switch which can be configured to reverse the polarity applied to the electric motor 82 by the power source 90. As with the other forms described herein, the handle 14 can also include a sensor that is configured to detect the position of the drive member 120 and/or the direction in which the drive member 120 is being moved.

Actuation of the motor 82 can be controlled by a firing trigger 130 that is pivotally supported on the handle 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first Hall effect sensor 803 and a second Hall effect sensor 804, for example, which can be configured to track the position of the magnet 802. Upon comparing FIGS. 14 and 17, the reader will appreciate that, when the closure trigger 32 is moved from its unactuated position to its actuated position, the magnet 802 can move between a first position adjacent the first Hall effect sensor 803 and a second position adjacent the second Hall effect sensor 804. Upon comparing FIGS. 17 and 18A, the reader will further appreciate that, when the firing trigger 130 is moved from an unfired position (FIG. 17) to a fired position (FIG. 18A), the magnet 802 can move relative to the second Hall effect sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 142 that is configured to be manually pivoted into ratcheting engagement with teeth 124 also provided in the drive member 120. Thus, the clinician can manually retract the drive member 120 by using the bailout handle assembly 142 to ratchet the drive member 120 in the proximal direction "PD". U.S. Patent Application Publication No. 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference in its entirety.

Figure 7:
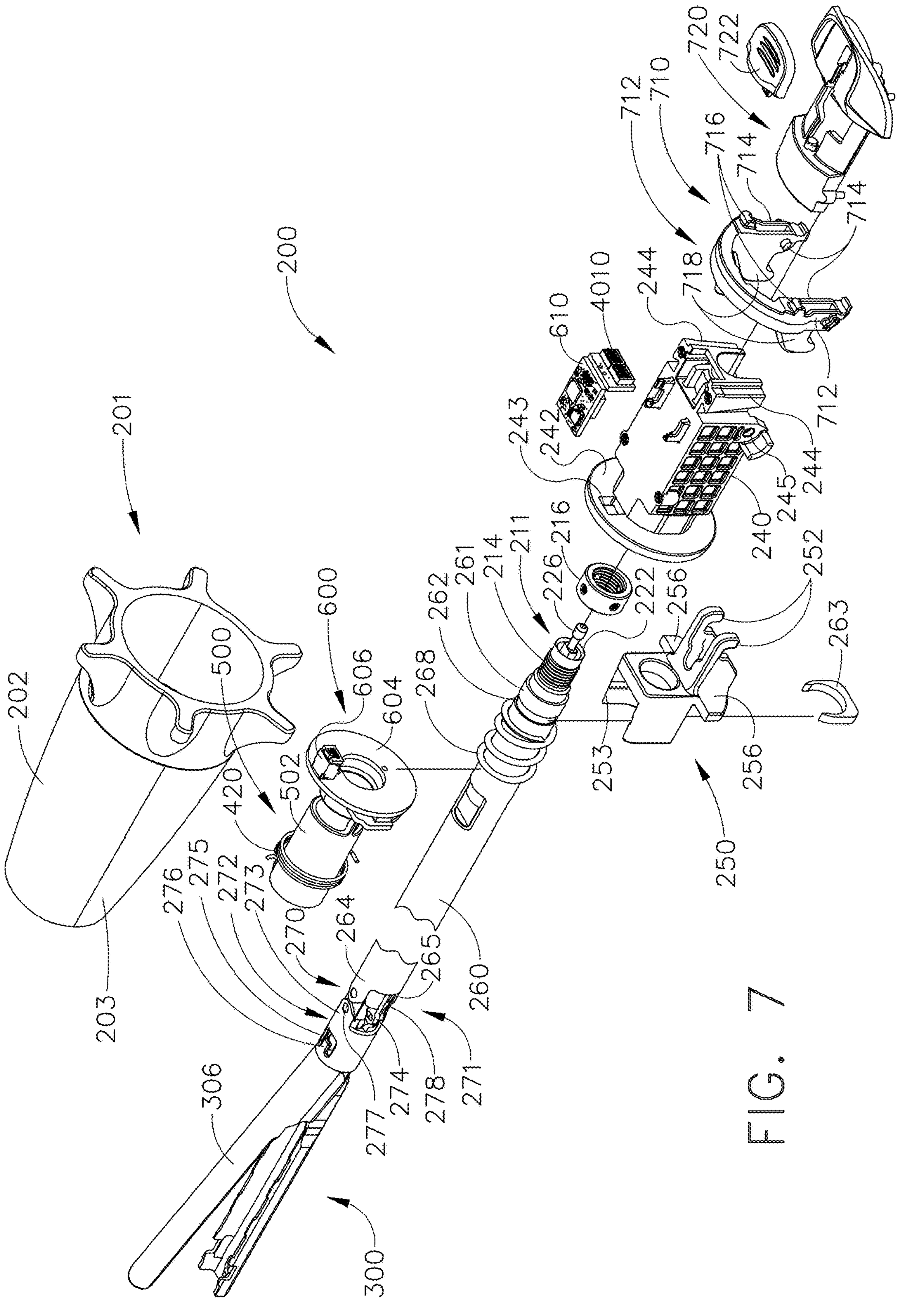
FIG. 7 is an exploded assembly view of one form of an interchangeable shaft assembly.
Figure 8:
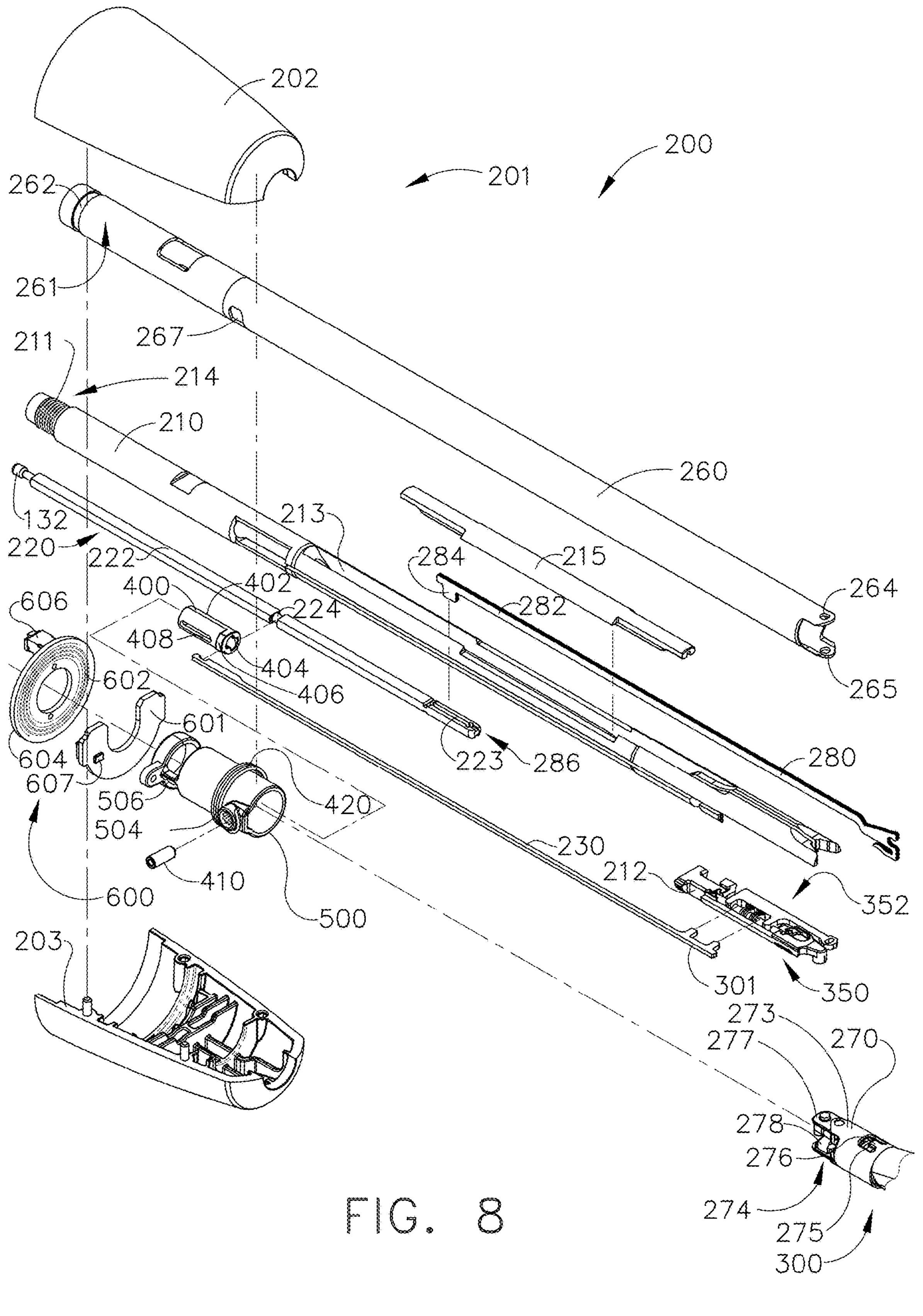
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086, now U.S. Patent Application Publication No. 2014/0263541. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As can be seen in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle 14.

In at least one form, the interchangeable shaft assembly 200 may further include an articulation joint 270. Other interchangeable shaft assemblies, however, may not be capable of articulation. As can be seen in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086, now U.S. Patent Application Publication No. 2014/0263541. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086, now U.S. Patent Application Publication No. 2014/0263541, which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 may also be articulated relative to the closure tube 260 by an articulation driver 230.

Figure 9:
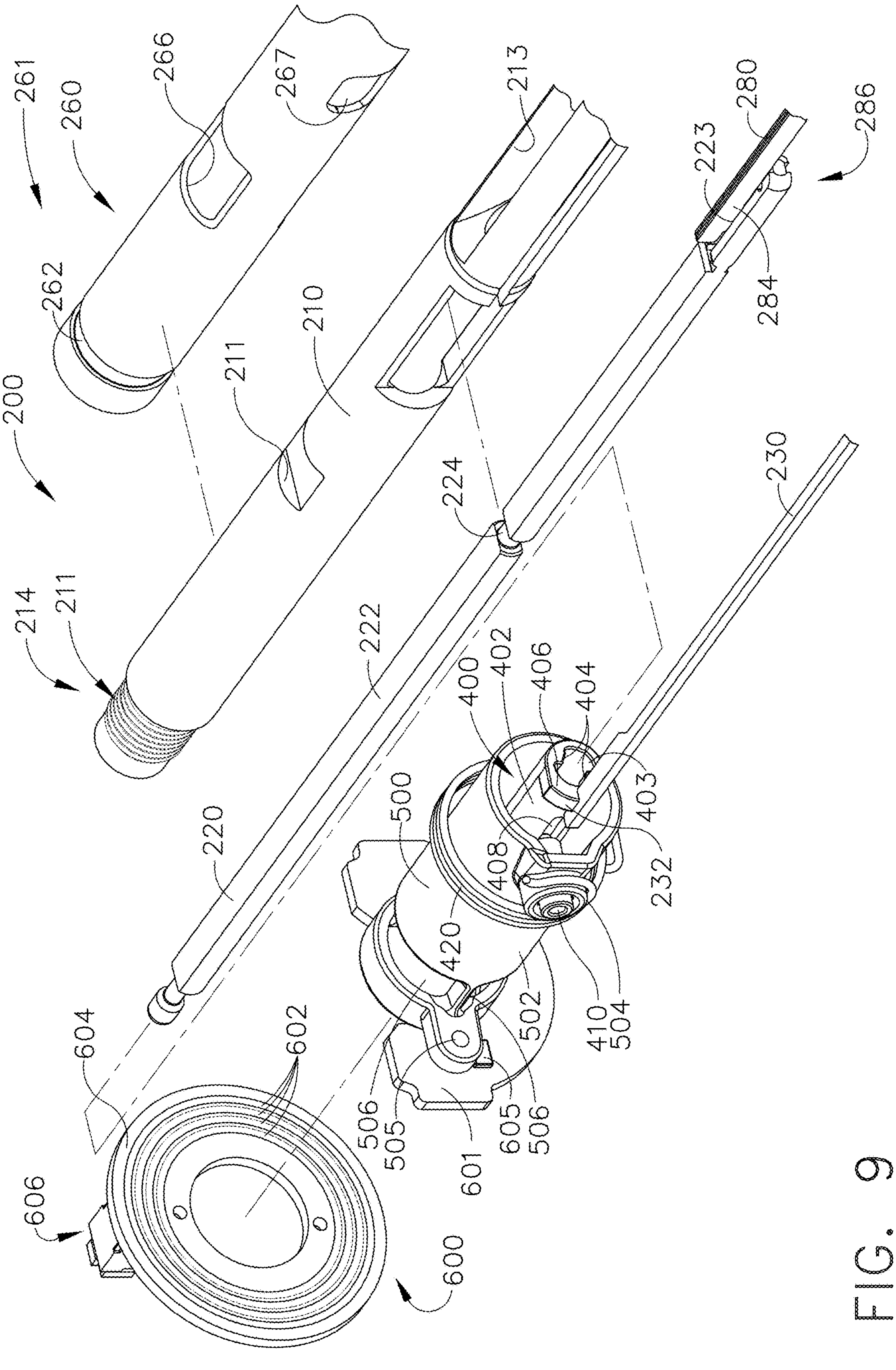
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 may also be referred to herein as a "second shaft" and/or a "second shaft assembly". As can be seen in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086, now U.S. Patent Application Publication No. 2014/0263541.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
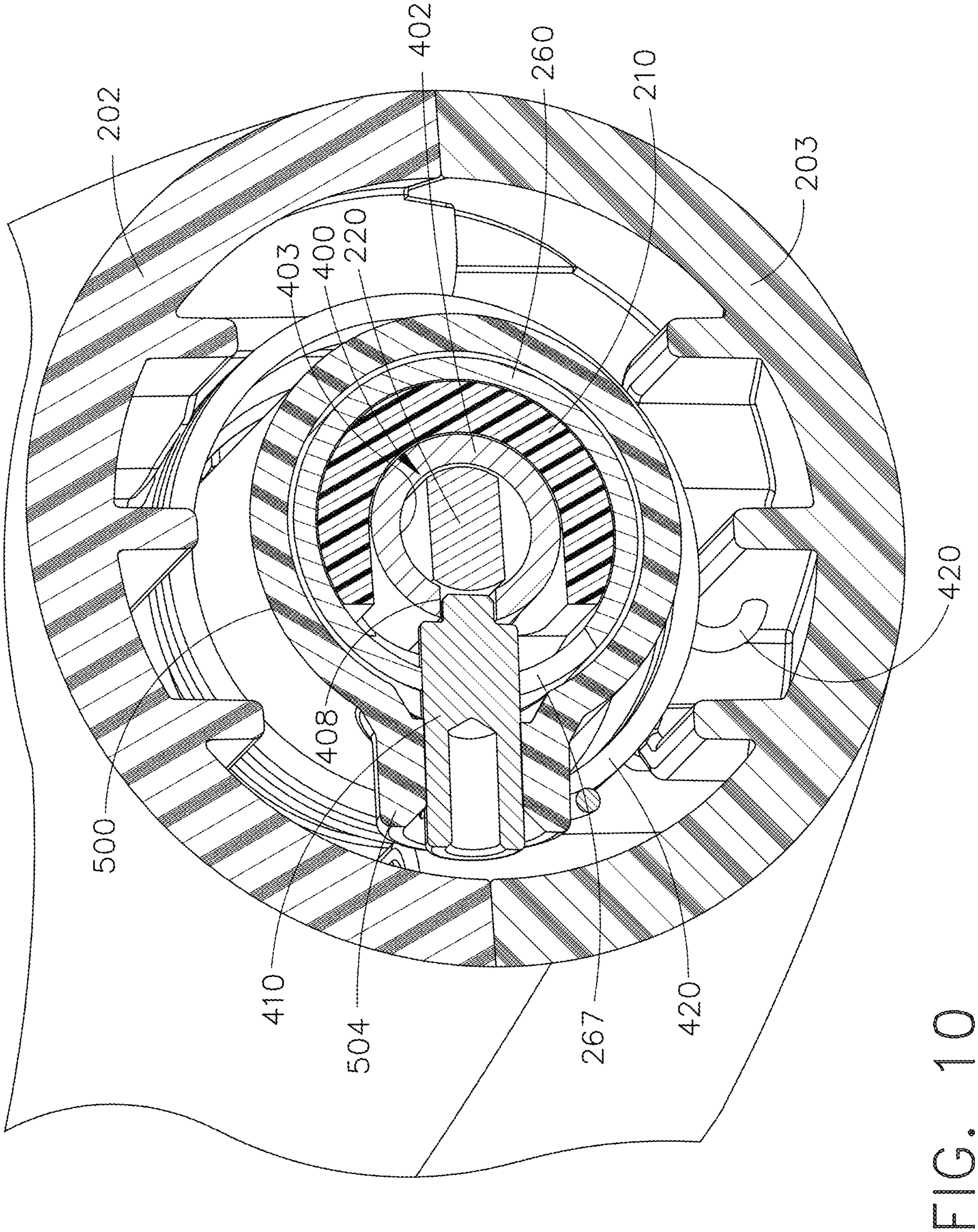
FIG. 10 is a cross-sectional view of a portion of the interchangeable shaft assembly of FIGS. 7-9.

As can be seen in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As can be seen in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of eth actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086, now U.S. Patent Application Publication No. 2014/0263541.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference in its entirety. U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481, is incorporated by reference in its entirety. Further details regarding slip ring assembly 600 may be found in U.S. patent application Ser. No. 13/803,086, now U.S. Patent Application Publication No. 2014/0263541.

Figure 11:
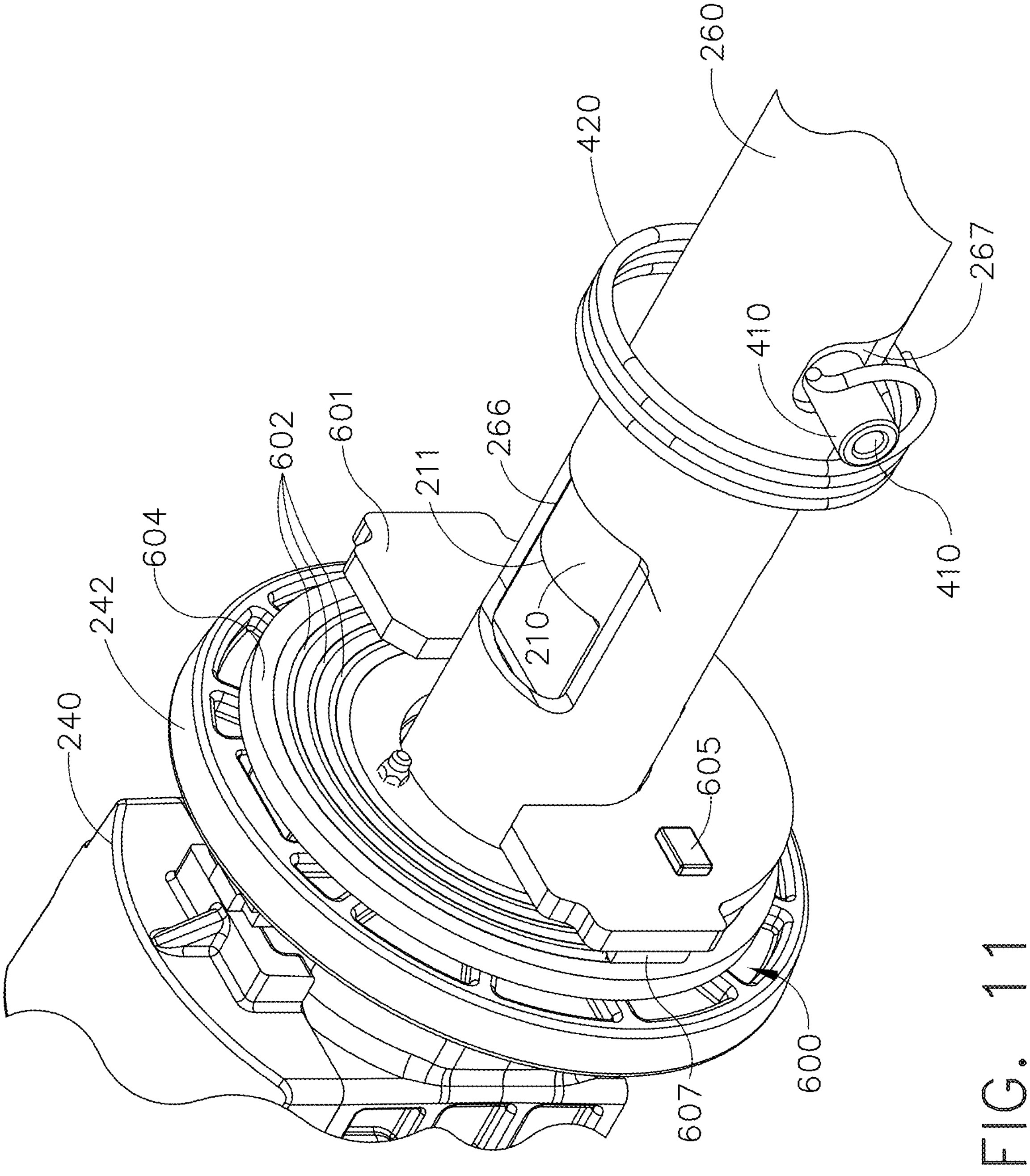
FIG. 11 is a perspective view of a portion of the shaft assembly of FIGS. 7-10 with the switch drum omitted for clarity.
Figure 12:
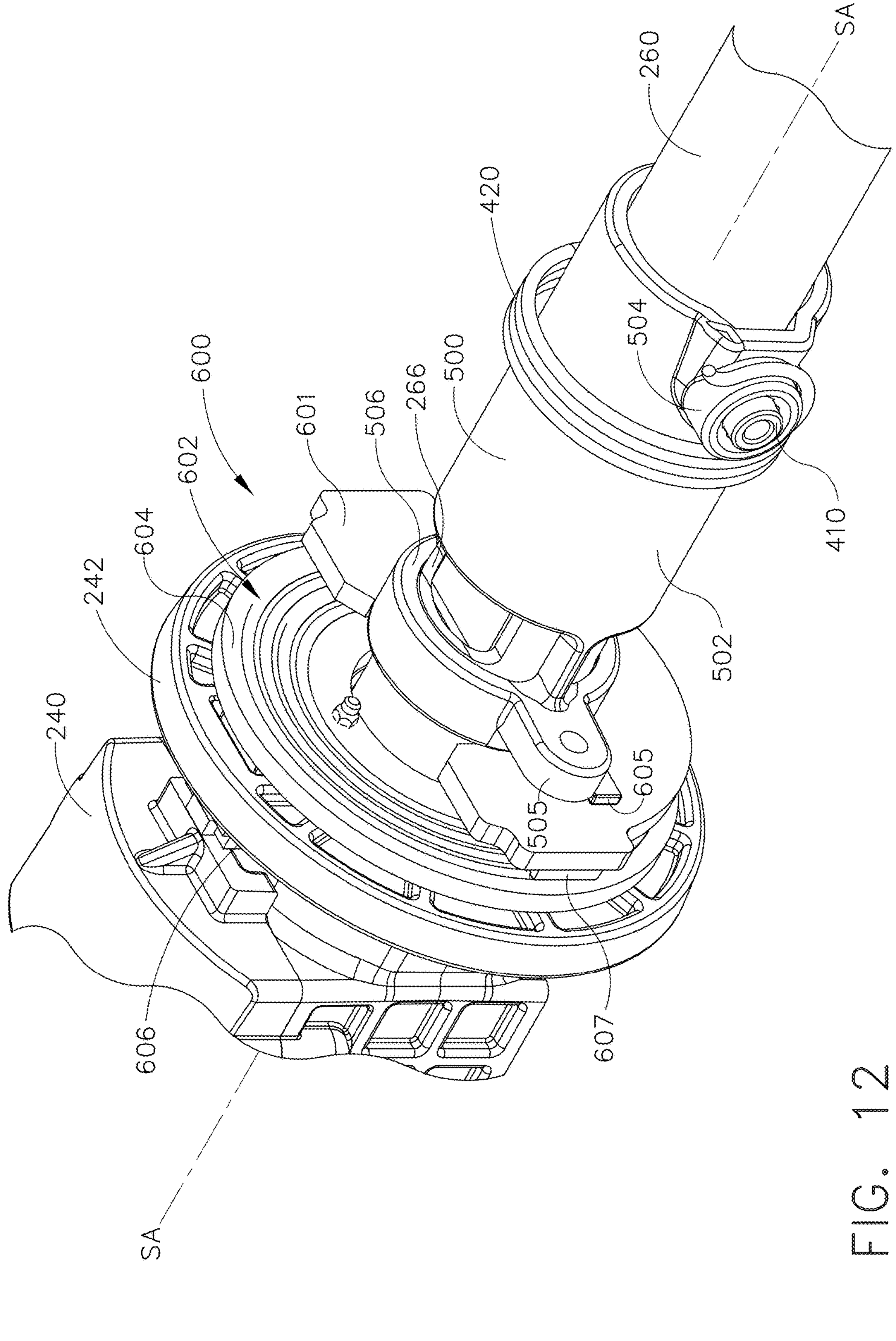
FIG. 12 is another perspective view of the portion of the interchangeable shaft assembly of FIG. 11 with the switch drum mounted thereon.

As discussed above, the shaft assembly 200 can include a proximal portion which is fixably mounted to the handle 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a Hall effect sensor 605, for example, and the switch drum 500 can comprise a magnetic element, such as permanent magnet 505, for example. The Hall effect sensor 605 can be configured to detect the position of the permanent magnet 505. When the switch drum 500 is rotated between its first position and its second position, the permanent magnet 505 can move relative to the Hall effect sensor 605. In various instances, Hall effect sensor 605 can detect changes in a magnetic field created when the permanent magnet 505 is moved. The Hall effect sensor 605 can be in signal communication with the shaft circuit board 610 and/or the handle circuit board 100, for example. Based on the signal from the Hall effect sensor 605, a microcontroller on the shaft circuit board 610 and/or the handle circuit board 100 can determine whether the articulation drive system is engaged with or disengaged from the firing drive system.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle 14, the shaft attachment lug 226 is received in a firing shaft attachment cradle 126 formed in the distal end 125 of the longitudinal drive member 120. See FIGS. 3 and 6.

Various shaft assembly embodiments employ a latch system 710 for removably coupling the shaft assembly 200 to the housing 12 and more specifically to the frame 20. As can be seen in FIG. 7, for example, in at least one form, the latch system 710 includes a lock member or lock yoke 712 that is movably coupled to the chassis 240. In the illustrated embodiment, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was in advertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle 14. A first system can comprise a frame system which couples and/or aligns the frame or spine of the shaft assembly 200 with the frame 20 of the handle 14. Another system can comprise a closure drive system 30 which can operably connect the closure trigger 32 of the handle 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle 14 with the intermediate firing shaft 222 of the shaft assembly 200. As outlined above, the shaft attachment lug 226 can be operably connected with the cradle 126 of the longitudinal drive member 120. Another system can comprise an electrical system which can signal to a controller in the handle 14, such as microcontroller, for example, that a shaft assembly, such as shaft assembly 200, for example, has been operably engaged with the handle 14 and/or, two, conduct power and/or communication signals between the shaft assembly 200 and the handle 14. For instance, the shaft assembly 200 can include an electrical connector 4010 that is operably mounted to the shaft circuit board 610. The electrical connector 4010 is configured for mating engagement with a corresponding electrical connector 4000 on the handle control board 100. Further details regaining the circuitry and control systems may be found in U.S. patent application Ser. No. 13/803,086, now U.S. Patent Application Publication No. 2014/0263541, the entire disclosure of which was previously incorporated by reference herein. The fifth system may consist of the latching system for releasably locking the shaft assembly 200 to the handle 14.

Figure 59:
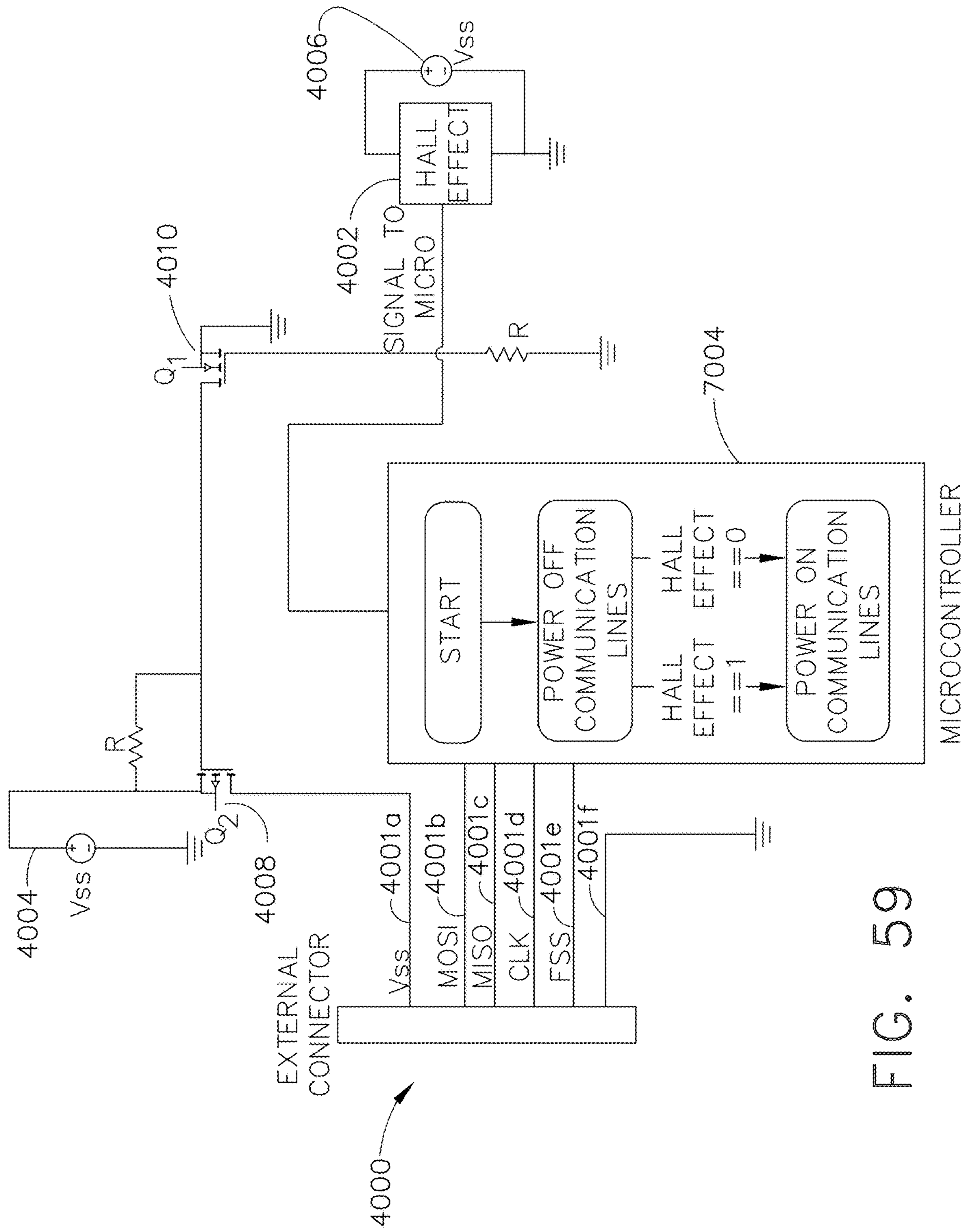
FIG. 59 is a schematic of a system for powering down an electrical connector of a surgical instrument handle when a shaft assembly is not coupled thereto.

Referring again to FIGS. 2 and 3, the handle 14 can include an electrical connector 4000 comprising a plurality of electrical contacts. Turning now to FIG. 59, the electrical connector 4000 can comprise a first contact 4001*a*, a second contact 4001*b*, a third contact 4001*c*, a fourth contact 4001*d*, a fifth contact 4001*e*, and a sixth contact 4001*f*, for example. While the illustrated embodiment utilizes six contacts, other embodiments are envisioned which may utilize more than six contacts or less than six contacts. As illustrated in FIG. 59, the first contact 4001*a* can be in electrical communication with a transistor 4008, contacts 4001*b*-4001*e* can be in electrical communication with a microcontroller 7004, and the sixth contact 4001*f* can be in electrical communication with a ground. In certain circumstances, one or more of the electrical contacts 4001*b*-4001*e* may be in electrical communication with one or more output channels of the microcontroller 7004 and can be energized, or have a voltage potential applied thereto, when the handle 1042 is in a powered state. In some circumstances, one or more of the electrical contacts 4001*b*-4001*e* may be in electrical communication with one or more input channels of the microcontroller 7004 and, when the handle 14 is in a powered state, the microcontroller 7004 can be configured to detect when a voltage potential is applied to such electrical contacts. When a shaft assembly, such as shaft assembly 200, for example, is assembled to the handle 14, the electrical contacts 4001*a*-4001*f* may not communicate with each other. When a shaft assembly is not assembled to the handle 14, however, the electrical contacts 4001*a*-4001*f* of the electrical connector 4000 may be exposed and, in some circumstances, one or more of the contacts 4001*a*-4001*f* may be accidentally placed in electrical communication with each other. Such circumstances can arise when one or more of the contacts 4001*a*-4001*f* come into contact with an electrically conductive material, for example. When this occurs, the microcontroller 7004 can receive an erroneous input and/or the shaft assembly 200 can receive an erroneous output, for example. To address this issue, in various circumstances, the handle 14 may be unpowered when a shaft assembly, such as shaft assembly 200, for example, is not attached to the handle 14. In other circumstances, the handle 1042 can be powered when a shaft assembly, such as shaft assembly 200, for example, is not attached thereto. In such circumstances, the microcontroller 7004 can be configured to ignore inputs, or voltage potentials, applied to the contacts in electrical communication with the microcontroller 7004, i.e., contacts 4001*b*-4001*e*, for example, until a shaft assembly is attached to the handle 14. Eventhough the microcontroller 7004 may be supplied with power to operate other functionalities of the handle 14 in such circumstances, the handle 14 may be in a powered-down state. In a way, the electrical connector 4000 may be in a powered-down state as voltage potentials applied to the electrical contacts 4001*b*-4001*e* may not affect the operation of the handle 14. The reader will appreciate that, eventhough contacts 4001*b*-4001*e* may be in a powered-down state, the electrical contacts 4001*a* and 4001*f*, which are not in electrical communication with the microcontroller 7004, may or may not be in a powered-down state. For instance, sixth contact 4001*f* may remain in electrical communication with a ground regardless of whether the handle 14 is in a powered-up or a powered-down state. Furthermore, the transistor 4008, and/or any other suitable arrangement of transistors, such as transistor 4010, for example, and/or switches may be configured to control the supply of power from a power source 4004, such as a battery 90 within the handle 14, for example, to the first electrical contact 4001*a* regardless of whether the handle 14 is in a powered-up or a powered-down state. In various circumstances, the shaft assembly 200, for example, can be configured to change the state of the transistor 4008 when the shaft assembly 200 is engaged with the handle 14. In certain circumstances, further to the below, a Hall effect sensor 4002 can be configured to switch the state of transistor 4010 which, as a result, can switch the state of transistor 4008 and ultimately supply power from power source 4004 to first contact 4001*a*. In this way, both the power circuits and the signal circuits to the connector 4000 can be powered down when a shaft assembly is not installed to the handle 14 and powered up when a shaft assembly is installed to the handle 14.

In various circumstances, referring again to FIG. 59, the handle 14 can include the Hall effect sensor 4002, for example, which can be configured to detect a detectable element, such as a magnetic element 4007 (FIG. 3), for example, on a shaft assembly, such as shaft assembly 200, for example, when the shaft assembly is coupled to the handle 14. The Hall effect sensor 4002 can be powered by a power source 4006, such as a battery, for example, which can, in effect, amplify the detection signal of the Hall effect sensor 4002 and communicate with an input channel of the microcontroller 7004 via the circuit illustrated in FIG. 59. Once the microcontroller 7004 has a received an input indicating that a shaft assembly has been at least partially coupled to the handle 14, and that, as a result, the electrical contacts 4001*a*-4001*f* are no longer exposed, the microcontroller 7004 can enter into its normal, or powered-up, operating state. In such an operating state, the microcontroller 7004 will evaluate the signals transmitted to one or more of the contacts 4001*b*-4001*e* from the shaft assembly and/or transmit signals to the shaft assembly through one or more of the contacts 4001*b*-4001*e* in normal use thereof. In various circumstances, the shaft assembly 1200 may have to be fully seated before the Hall effect sensor 4002 can detect the magnetic element 4007. While a Hall effect sensor 4002 can be utilized to detect the presence of the shaft assembly 200, any suitable system of sensors and/or switches can be utilized to detect whether a shaft assembly has been assembled to the handle 14, for example. In this way, further to the above, both the power circuits and the signal circuits to the connector 4000 can be powered down when a shaft assembly is not installed to the handle 14 and powered up when a shaft assembly is installed to the handle 14.

In various embodiments, any number of magnetic sensing elements may be employed to detect whether a shaft assembly has been assembled to the handle 14, for example. For example, the technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 59, the microcontroller 7004 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 7004 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 7004 may include a hybrid circuit comprising discrete and integrated circuit elements or components on one or more substrates, for example.

Referring to FIG. 59, the microcontroller 7004 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle 14 and/or the shaft assembly 200 can include systems and configurations configured to prevent, or at least reduce the possibility of, the contacts of the handle electrical connector 4000 and/or the contacts of the shaft electrical connector 4010 from becoming shorted out when the shaft assembly 200 is not assembled, or completely assembled, to the handle 14. Referring to FIG. 3, the handle electrical connector 4000 can be at least partially recessed within a cavity 4009 defined in the handle frame 20. The six contacts 4001*a*-4001*f* of the electrical connector 4000 can be completely recessed within the cavity 4009. Such arrangements can reduce the possibility of an object accidentally contacting one or more of the contacts 4001*a*-4001*f*. Similarly, the shaft electrical connector 4010 can be positioned within a recess defined in the shaft chassis 240 which can reduce the possibility of an object accidentally contacting one or more of the contacts 4011*a*-4011*f* of the shaft electrical connector 4010. With regard to the particular embodiment depicted in FIG. 3, the shaft contacts 4011*a*-4011*f* can comprise male contacts. In at least one embodiment, each shaft contact 4011*a*-4011*f* can comprise a flexible projection extending therefrom which can be configured to engage a corresponding handle contact 4001*a*-4001*f*, for example. The handle contacts 4001*a*-4001*f* can comprise female contacts. In at least one embodiment, each handle contact 4001*a*-4001*f* can comprise a flat surface, for example, against which the male shaft contacts 4001*a*-4001*f* can wipe, or slide, against and maintain an electrically conductive interface therebetween. In various instances, the direction in which the shaft assembly 200 is assembled to the handle 14 can be parallel to, or at least substantially parallel to, the handle contacts 4001*a*-4001*f* such that the shaft contacts 4011*a*-4011*f* slide against the handle contacts 4001*a*-4001*f* when the shaft assembly 200 is assembled to the handle 14. In various alternative embodiments, the handle contacts 4001*a*-4001*f* can comprise male contacts and the shaft contacts 4011*a*-4011*f* can comprise female contacts. In certain alternative embodiments, the handle contacts 4001*a*-4001*f* and the shaft contacts 4011*a*-4011*f* can comprise any suitable arrangement of contacts.

In various instances, the handle 14 can comprise a connector guard configured to at least partially cover the handle electrical connector 4000 and/or a connector guard configured to at least partially cover the shaft electrical connector 4010. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one embodiment, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 4000, for example. In various instances, the contacts can be transitioned between an unactivated condition and an activated condition. In certain instances, the contacts can be transitioned between a monitored condition, a deactivated condition, and an activated condition. For instance, the microcontroller 7004, for example, can monitor the contacts 4001*a*-4001*f* when a shaft assembly has not been assembled to the handle 14 to determine whether one or more of the contacts 4001*a*-4001*f* may have been shorted. The microcontroller 7004 can be configured to apply a low voltage potential to each of the contacts 4001*a*-4001*f* and assess whether only a minimal resistance is present at each of the contacts. Such an operating state can comprise the monitored condition. In the event that the resistance detected at a contact is high, or above a threshold resistance, the microcontroller 7004 can deactivate that contact, more than one contact, or, alternatively, all of the contacts. Such an operating state can comprise the deactivated condition. If a shaft assembly is assembled to the handle 14 and it is detected by the microcontroller 7004, as discussed above, the microcontroller 7004 can increase the voltage potential to the contacts 4001*a*-4001*f*. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

FIGS. 19-22 depict one form of electric coupler or slip ring connector 1600 that may be employed with, for example an interchangeable shaft assembly 1200 or a variety of other applications that require electrical connections between components that rotate relative to each other. The shaft assembly 1200 may be similar to shaft assembly 200 described herein and include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240 for rotation relative thereto about a shaft axis SA-SA. As was discussed above, the proximal nozzle 1201 may include mounts or mounting lugs 1204 (FIG. 20) that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240, the clinician simply rotates the nozzle 1201 as represented by arrows "R" in FIG. 19.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800 mounted within the nozzle 1201. Thus, the distal electrical component 1800 is rotatable with the nozzle 1201 about the shaft axis SA-SA. In the embodiment illustrated in FIG. 20, the electrical component 1800 comprises a connector, battery, etc. that includes contacts 1802, 1804, 1806, and 1808 that are laterally displaced from each other.

The slip ring connector 1600 further includes a mounting member 1610 that includes a cylindrical body portion 1612 that defines an annular mounting surface 1613. A distal flange 1614 may be formed on at least one end of the cylindrical body portion 1612. The body portion 1612 of the mounting member 1610 is sized to be non-rotatably mounted on a mounting hub 1241 on the chassis 1240. In the illustrated embodiment, one distal flange 1614 is provided on one end of the body portion 1612. A second flange 1243 is formed on the chassis 1240 such that when the body portion 1612 is fixedly (non-rotatably) mounted thereon, the second flange 1243 abuts the proximal end of the body portion 1612.

Figure 21:
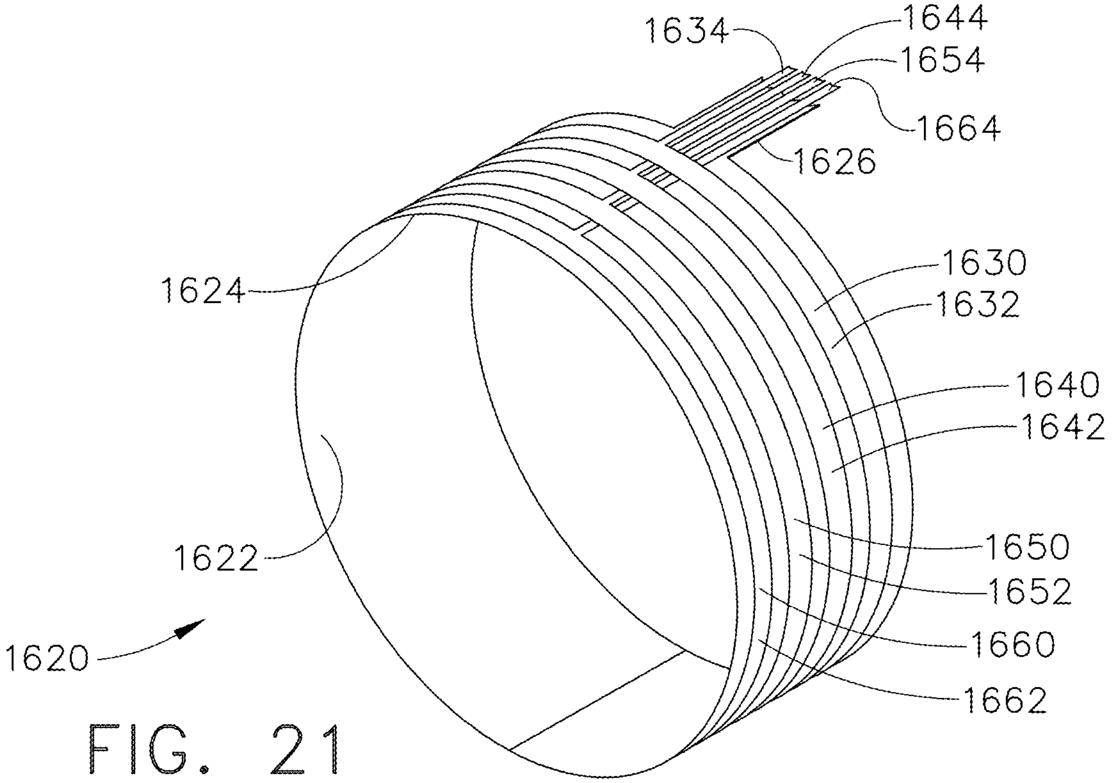
FIG. 21 is a perspective view of circuit trace assembly.
Figure 22:
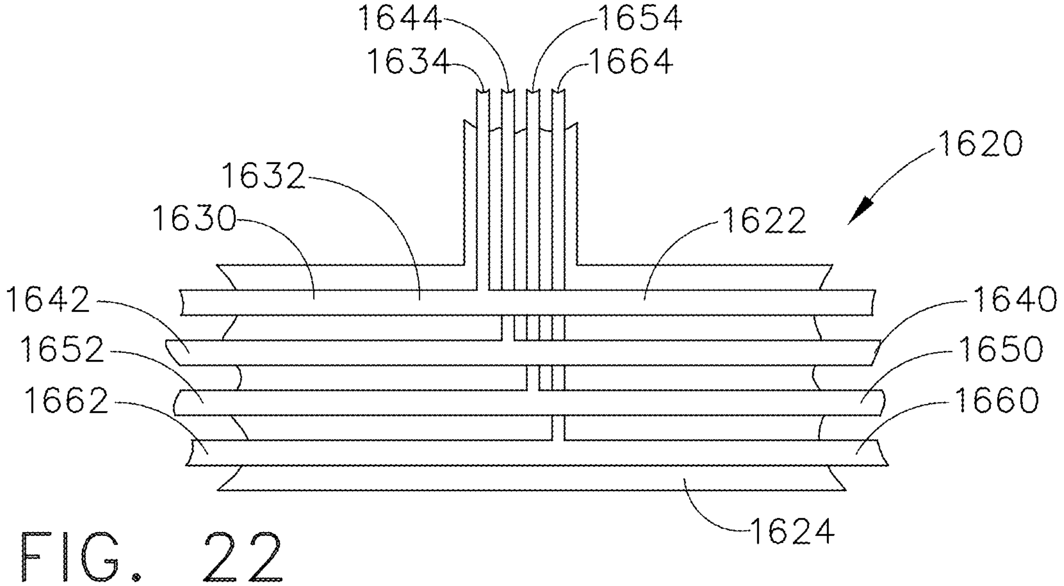
FIG. 22 is a plan view of a portion of the circuit trace assembly of FIG. 21.

The slip ring connector 1600 also employs a unique and novel annular circuit trace assembly 1620 that is wrapped around the annular mounting surface 1613 of the body portion 1612 such that it is received between the first and second flanges 1614 and 1243. Referring now to FIGS. 21 and 22, the circuit trace assembly 1620 may comprise an adhesive-backed flexible substrate 1622 that may be wrapped around the circumference of the body portion 1612 (i.e., the annular mounting surface 1613). Prior to being wrapped around the body portion 1612, the flexible substrate 1622 may have a "T-shape" with a first annular portion 1624 and a lead portion 1626. As can also be seen in FIGS. 19-21, the circuit trace assembly 1620 may further include circuit traces 1630, 1640, 1650, 1660 that may comprise, for example, electrically-conductive gold-plated traces. However, other electrically-conductive materials may also be used. Each electrically-conductive circuit trace includes an "annular portion" that will form an annular part of the trace when the substrate is wrapped around the body portion 1612 as well as another "lead portion" that extends transversely from or perpendicular from the annular portion. More specifically, referring to FIG. 22, first electrically-conductive circuit trace 1630 has a first annular portion 1632 and first lead portion 1634. The second electrically-conductive circuit trace 1640 has a second annular portion 1642 and a second lead portion 1644 extending transversely or perpendicularly therefrom. The third electrically conductive circuit trace 1650 has a third annular portion 1652 and a third lead portion 1654 extending transversely or perpendicularly therefrom. The fourth electrically-conductive circuit trace has a fourth annular portion 1662 and a fourth lead portion 1664 extending transversely or perpendicularly therefrom.

The electrically-conductive circuit traces 1630, 1640, 1650, 1660 may be applied to the flexible substrate 1622 while the substrate is in a planar orientation (i.e., prior to being wrapped onto the annular body portion 1612 of the mounting member 1610) using conventional manufacturing techniques. As can be seen in FIG. 22, the annular portions 1632, 1642, 1652, 1662 are laterally displaced from each other. Likewise, the lead portions 1634, 1644, 1654, 1664 are laterally displaced from each other.

When the circuit trace assembly 1620 is wrapped around the annular mounting surface 1613 and attached thereto by adhesive, double-stick tape, etc., the ends of the portion of the substrate that contains the annular portions 1632, 1642, 1652, 1664 are butted together such that the annular portions 1632, 1642, 1652, 1664 form discrete continuous annular electrically-conductive paths 1636, 1646, 1656, 1666, respectively that extend around the shaft axis SA-SA. Thus, the electrically-conductive paths 1636, 1646, 1656, and 1666 are laterally or axially displaced from each other along the shaft axis SA-SA. The lead portion 1626 may extend through a slot 1245 in the flange 1243 and be electrically coupled to a circuit board (see e.g., FIG. 7—circuit board 610) or other suitable electrical component(s).

In the depicted embodiment for example, the electrical component 1800 is mounted within the nozzle 1261 for rotation about the mounting member 1610 such that: contact 1802 is in constant electrical contact with the first annular electrically-conductive path 1636; contact 1804 is in constant electrical contact with the second annular electrically-conductive path 1646; contact 1806 is in constant electrical contact with the third annular electrically-conductive path 1656; and contact 1808 is in constant electrical contact with the fourth electrically-conductive path 1666. It will be understood however, that the various advantages of the slip ring connector 1600 may also be obtained in applications wherein the mounting member 1610 is supported for rotation about the shaft axis SA-SA and the electrical component 1800 is fixedly mounted relative thereto. It will be further appreciated that the slip ring connector 1600 may be effectively employed in connection with a variety of different components and applications outside the field of surgery wherein it is desirable to provide electrical connections between components that rotate relative to each other.

The slip ring connector 1600 comprises a radial slip ring that provides a conductive contact means of passing signal (s) and power to and from any radial position and after shaft rotation. In applications wherein the electrical component comprises a battery contact, the battery contact position can be situated relative to the mounting member to minimize any tolerance stack up between those components. The coupler arrangement may represent a low cost coupling arrangement that can be assembled with minimal manufacturing costs. The gold plated traces may also minimize the likelihood of corrosion. The unique and novel contact arrangement facilitates complete clockwise and counterclockwise rotation about the shaft axis SA-SA while remaining in electrical contact with the corresponding annular electrically-conductive paths.

Figure 23:
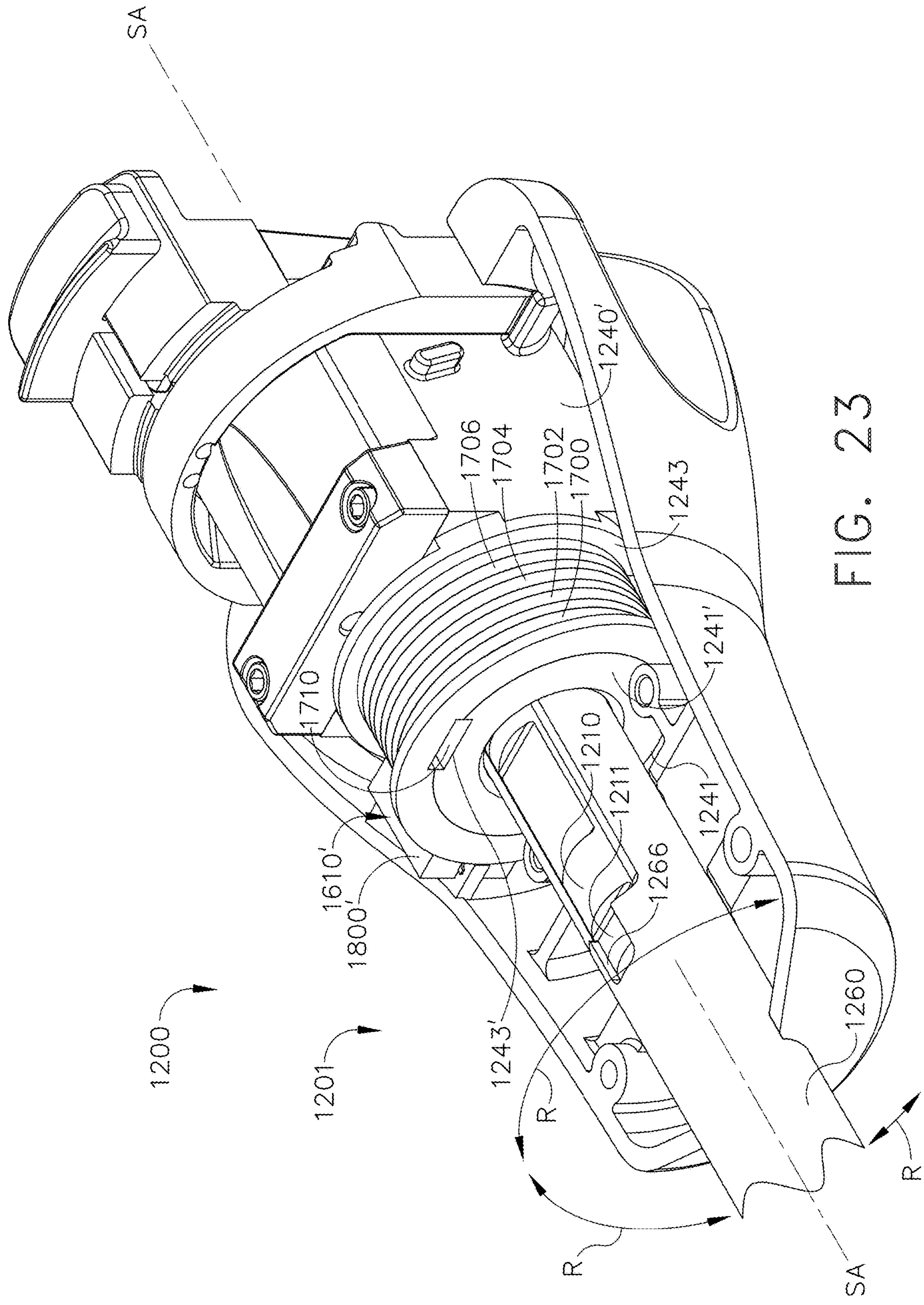
FIG. 23 is a perspective view of a portion of another interchangeable shaft assembly showing another electrical coupler arrangement.
Figure 24:
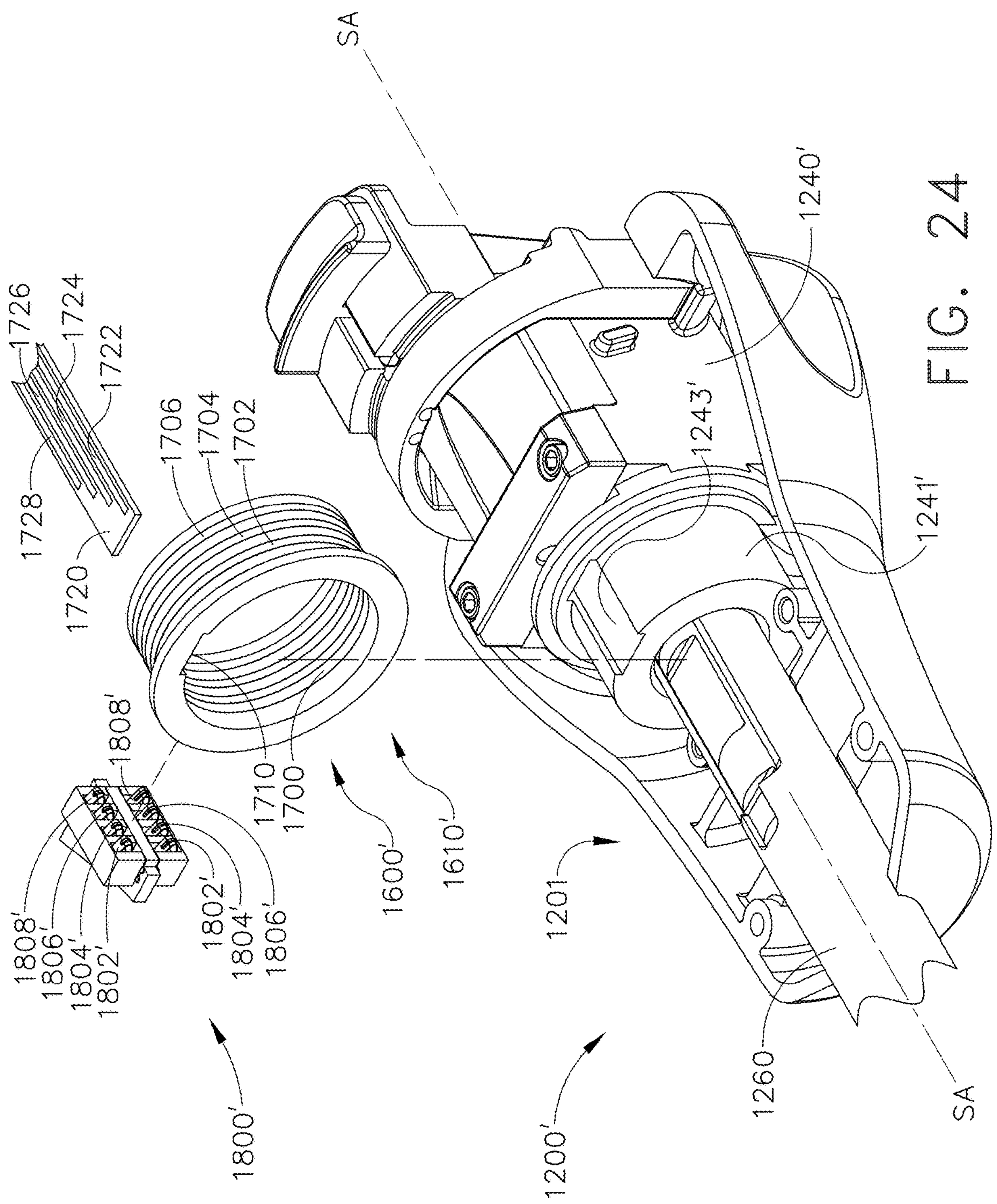
FIG. 24 is an exploded assembly view of portions of the interchangeable shaft assembly and electrical coupler of FIG. 23.
Figure 25:
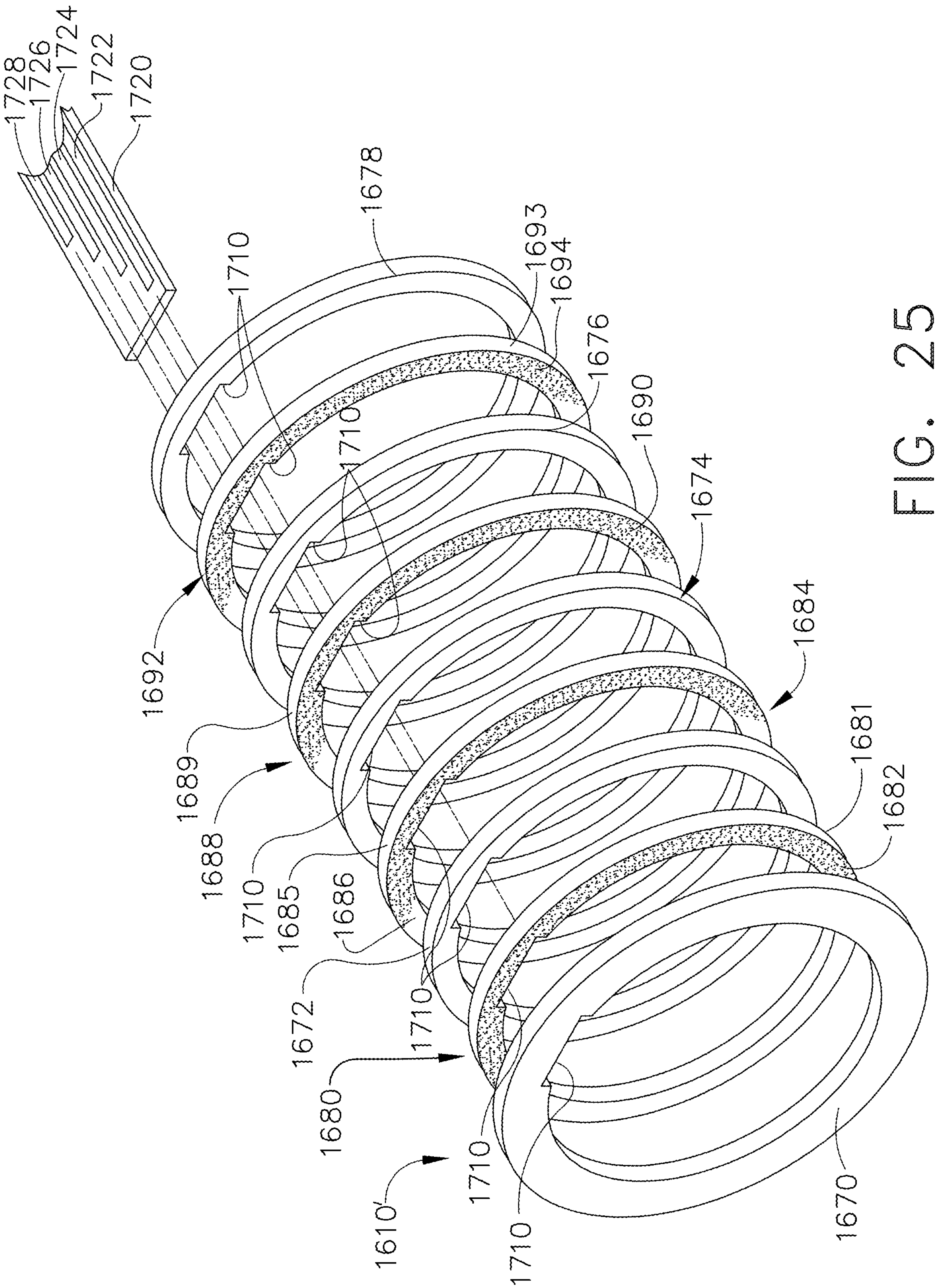
FIG. 25 is an exploded slip ring assembly of the electrical coupler of FIGS. 23 and 24.

FIGS. 23-25 depict one form of electric coupler or slip ring connector 1600' that may be employed with, for example an interchangeable shaft assembly 1200' or a variety of other applications that require electrical connections between components that rotate relative to each other. The shaft assembly 1200' may be similar to shaft assembly 1200 described herein and include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240' for rotation relative thereto about a shaft axis SA-SA. As was discussed above, the proximal nozzle 1201 may include mounts or mounting lugs that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240', the clinician simply rotates the nozzle 1201 as represented by arrows "R" in FIG. 23.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800' mounted within the nozzle 1201. Thus, the distal electrical component 1800' is rotatable with the nozzle 1201 and the wires/traces attached thereto. In the embodiment illustrated in FIG. 23, the electrical component 1800 comprises a connector, battery, etc. that includes contacts 1802', 1804', 1806', 1808' that are laterally displaced from each other.

The slip ring connector 1600' further includes a laminated slip ring assembly 1610' that is fabricated from a plurality of conductive rings that are laminated together. More specifically and with reference to FIG. 25, one form of slip ring assembly 1610' may comprise a first non-electrically conductive flange 1670 that forms a distal end of the slip ring assembly 1610'. The flange 1670 may be fabricated from a high-heat resistant material, for example. A first electrically conductive ring 1680 is positioned immediately adjacent the first flange 1670. The first electrically conductive ring 1680 may comprise a first copper ring 1681 that has a first gold plating 1682 thereon. A second non-electrically conductive ring 1672 is adjacent to the first electrically-conductive ring 1680. A second electrically-conductive ring 1684 is adjacent to the second non-electrically-conductive ring 1672. The second electrically-conductive ring 1684 may comprise a second copper ring 1685 that has a second gold plating 1686 thereon. A third non-electrically-conductive ring 1674 is adjacent to the second electrically-conductive ring 1684. A third electrically conductive ring 1688 is adjacent to the third non-electrically conductive ring 1674. The third electrically conductive ring 1688 may comprise a third copper ring 1689 that has a third gold plating 1690 thereon. A fourth non-electrically conductive ring 1676 is adjacent to the third electrically-conductive ring 1688. A fourth electrically conductive ring 1692 is adjacent to the fourth non-electrically-conductive ring 1676. The fourth electrically-conductive ring 1692 is adjacent to the fourth non-electrically conductive ring 1676. A fifth non-electrically conductive ring 1678 is adjacent to the fourth electrically-conductive ring 1692 and forms the proximal end of the mounting member 1610'. The non-electrically conductive rings 1670, 1672, 1674, 1676, and 1678 may be fabricated from the same material. The first electrically-conductive ring 1680 forms a first annular electrically-conductive pathway 1700. The second electrically-conductive ring 1682 forms a second annular electrically-conductive pathway 1702 that is laterally or axially spaced from the first annular electrically-conductive pathway 1700. The third electrically-conductive ring 1688 forms a third annular electrically conductive pathway 1704 that is laterally or axially spaced from the second annular electrically-conductive pathway 1702. The fourth electrically-conductive ring 1692 forms a fourth annular electrically-conductive pathway 1706 that is laterally or axially spaced from the third annular electrically-conductive pathway 1704. The slip ring assembly 1610' comprises a one piece molded high temperature resistant, non-conductive material with molded in channels for electromagnetic forming (EMF—Magneformed) copper rings.

As can be seen in FIG. 24, the slip ring connector 1600' further includes a non-conductive transverse mounting member 1720 that is adapted to be inserted into axially-aligned notches 1710 in each of the rings 1670, 1680, 1672, 1684, 1674, 1688, 1676, 1692, and 1678. The transverse mounting member 1720 has a first circuit trace 1722 thereon that is adapted for electrical contact with the first annular electrically-conductive pathway 1700 when the transverse mounting member 1672 is mounted within the notches 1710. Likewise, a second circuit trace 1724 is printed on the transverse mounting member 1720 and is configured for electrical contact with the second annular electrically conductive pathway 1702. A third circuit trace 1726 is printed on the transverse mounting member 1720 and is configured for electrical contact with the third annular electrically-conductive pathway 1704. A fourth circuit trace 1728 is printed on the transverse mounting member 1720 and is configured for electrical contact with the fourth annular electrically-conductive pathway 1706.

In the arrangement depicted in FIGS. 23-25, the slip ring assembly 1610' is configured to be fixedly (non-rotatably) received on a mounting hub 1241' on the chassis 1240'. The transverse mounting member 1720 is received within groove 1243' formed in the mounting hub 1241' which acts as a keyway for the transverse mounting member 1720 and which serves to prevent the slip ring assembly 1610' from rotating relative to the mounting hub 1241'.

In the depicted embodiment for example, the electrical component 1800' is mounted within the nozzle 1201 for rotation about the slip ring assembly 1610' such that: contact 1802' is in constant electrical contact with the first annular electrically-conductive path 1700; contact 1804' is in constant electrical contact with the second annular electrically-conductive path 1702; contact 1806' is in constant electrical contact with the third annular electrically-conductive path 1704; and contact 1808' is in constant electrical contact with the fourth electrically-conductive path 1706. It will be understood however, that the various advantages of the slip ring connector 1600' may also be obtained in applications wherein the slip ring assembly 1610' is supported for rotation about the shaft axis SA-SA and the electrical component 1800' is fixedly mounted relative thereto. It will be further appreciated that the slip ring connector 1600' may be effectively employed in connection with a variety of different components and applications outside the field of surgery wherein it is desirable to provide electrical connections between components that rotate relative to each other.

The slip ring connector 1600' comprises a radial slip ring that provides a conductive contact means of passing signal (s) and power to and from any radial position and after shaft rotation. In applications wherein the electrical component comprises a battery contact, the battery contact position can be situated relative to the mounting member to minimize any tolerance stack-up between those components. The slip ring connector 1600' represents a low cost coupling arrangement that can be assembled with minimal manufacturing costs. The gold plated traces may also minimize the likelihood of corrosion. The unique and novel contact arrangement facilitates complete clockwise and counterclockwise rotation about the shaft axis while remaining in electrical contact with the corresponding annular electrically-conductive paths.

FIGS. 26-30 depict another form of electric coupler or slip ring connector 1600" that may be employed with, for example an interchangeable shaft assembly 1200" or a variety of other applications that require electrical connections between components that rotate relative to each other. The shaft assembly 1200" may be similar to shaft assemblies 1200 and/or 1200' described herein except for the differences noted below. The shaft assembly 1200" may include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240" for rotation relative thereto about a shaft axis SA-SA. As was discussed above, the proximal nozzle 1201 may include mounts or mounting lugs that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240", the clinician simply rotates the nozzle 1201.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800'" mounted within the nozzle 1201. In the illustrated embodiment, for example, the electrical component 1800" is mounted in the nozzle 1201 such that it is substantially aligned with the shaft axis SA-SA. The distal electrical component 1800" is rotatable about the shaft axis SA-SA with the nozzle 1201 and the wires/traces attached thereto. The electrical component 1800" may comprise a connector, a battery, etc. that includes four contacts 1802", 1804", 1806", 1808" that are laterally displaced from each other.

The slip ring connector 1600" further includes a slip ring assembly 1610" that includes a base ring 1900 that is fabricated from a non-electrically conductive material and has a central mounting bore 1902 therethrough. The mounting bore 1902 has a flat surface 1904 and is configured for non-rotational attachment to a mounting flange assembly 1930 that is supported at a distal end of the chassis 1240". A distal side 1905 of the base ring 1900 has a series of concentric electrical-conductive rings 1906, 1908, 1910, and 1912 attached or laminated thereto. The rings 1906, 1908, 1910, and 1912 may be attached to the base ring 1900 by any suitable method.

Figure 28:
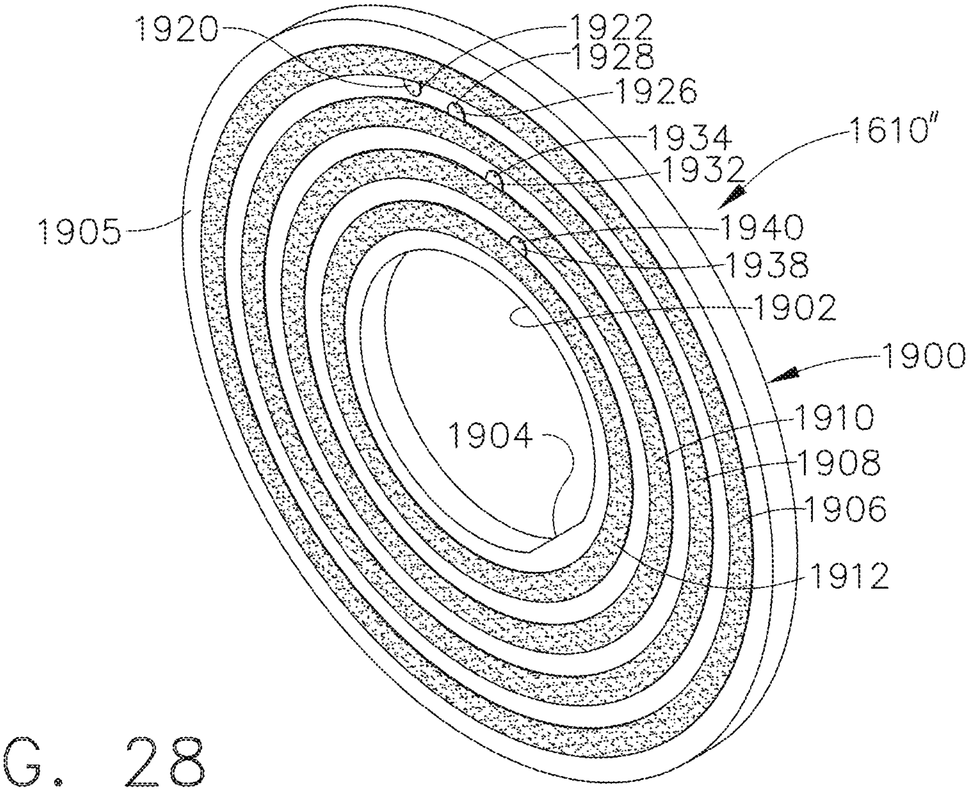
FIG. 28 is a front perspective view of a portion of the slip ring assembly of the electrical coupler of FIGS. 26 and 27.
Figure 29:
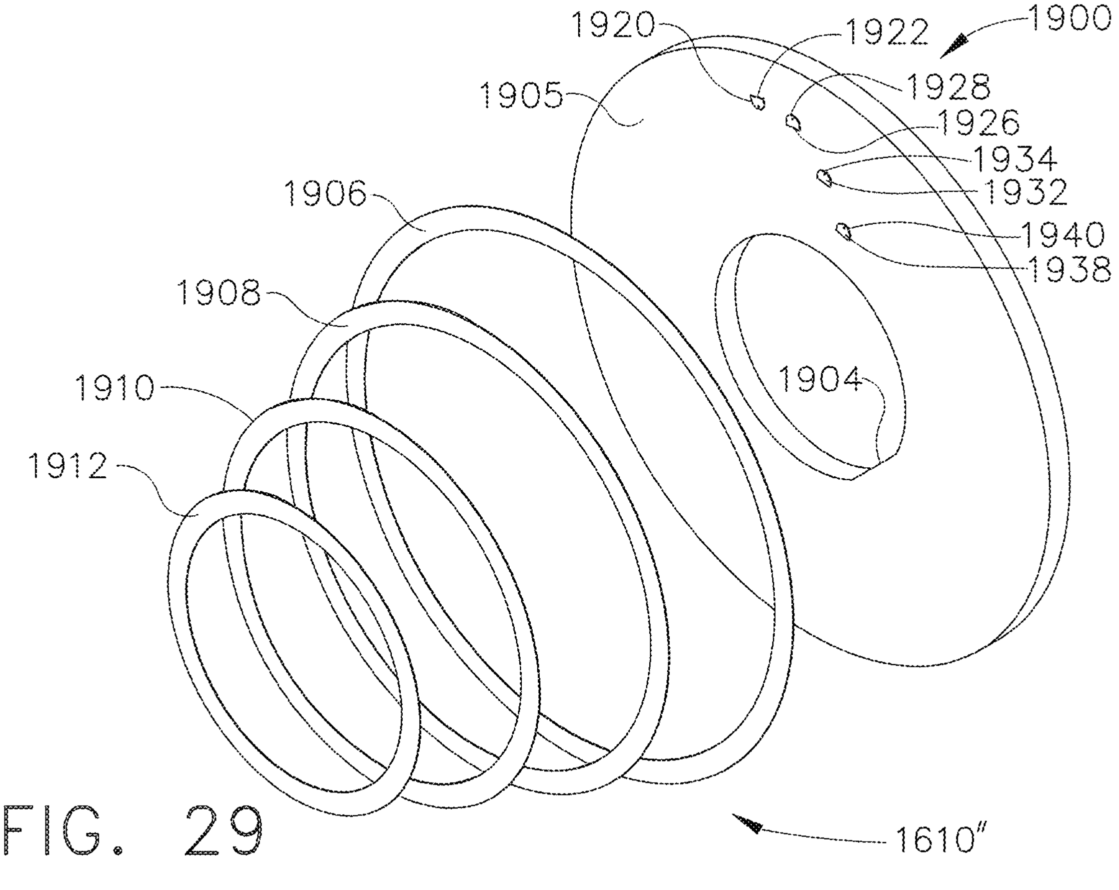
FIG. 29 is an exploded assembly view of the slip ring assembly portion of FIG. 28.
Figure 30:
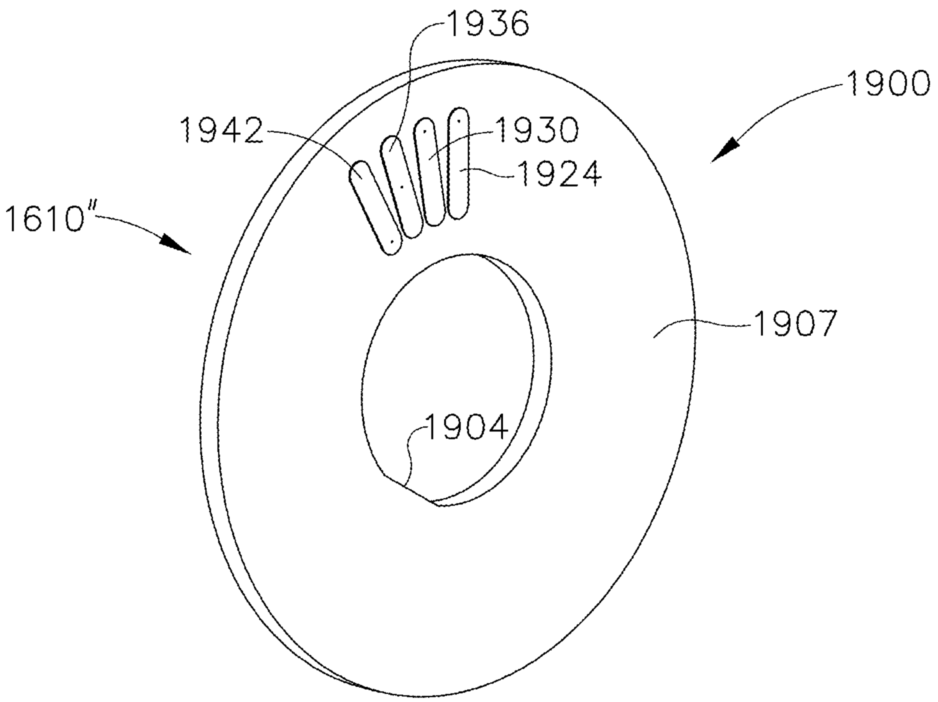
FIG. 30 is a rear perspective view of the portion of slip ring assembly of FIGS. 28 and 29.

The base ring 1900 may further include a circuit trace extending therethrough that is coupled to each of the electrically-conductive rings 1906, 1908, 1910, and 1912. Referring now to FIGS. 28-30, a first circuit trace 1922 extends through a first hole 1920 in the base ring 1900 and is coupled to the first electrically conductive ring 1906. The first circuit trace 1922 terminates in a first proximal contact portion 1924 on the proximal side 1907 of the base ring 1900. See FIG. 30. Similarly, a second circuit trace 1928 extends through a second hole 1926 in the base ring 1900 and is coupled to the second electrically-conductive ring 1908. The second circuit trace 1928 terminates in a second proximal contact 1930 on the proximal side 1907 of the base ring 1900. A third circuit trace 1934 extends through a third hole 1932 in the base ring and is attached to the third electrically-conductive ring 1910. The third circuit trace 1934 terminates in a third proximal contact 1936 on the proximal side 1907 of the base ring. A fourth circuit trace 1940 extends through a fourth hole 1938 in the base ring 1900 to be attached to the fourth electrically-conductive ring 1912. The fourth circuit trace 1940 terminates in a fourth proximal contact 1942 on the proximal side 1907 of the base ring 1900.

Figure 26:
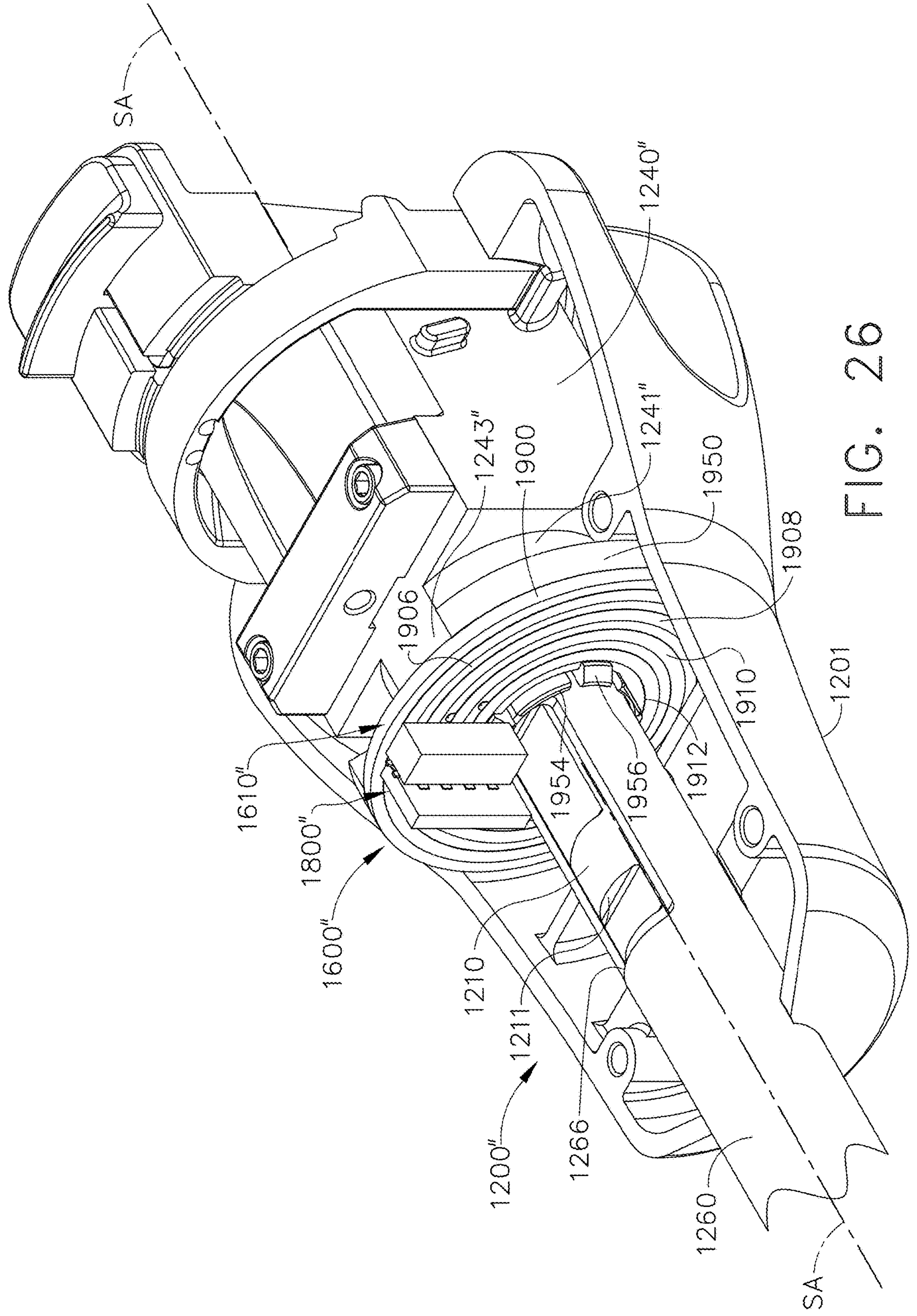
FIG. 26 is a perspective view of a portion of another interchangeable shaft assembly showing another electrical coupler arrangement.
Figure 27:
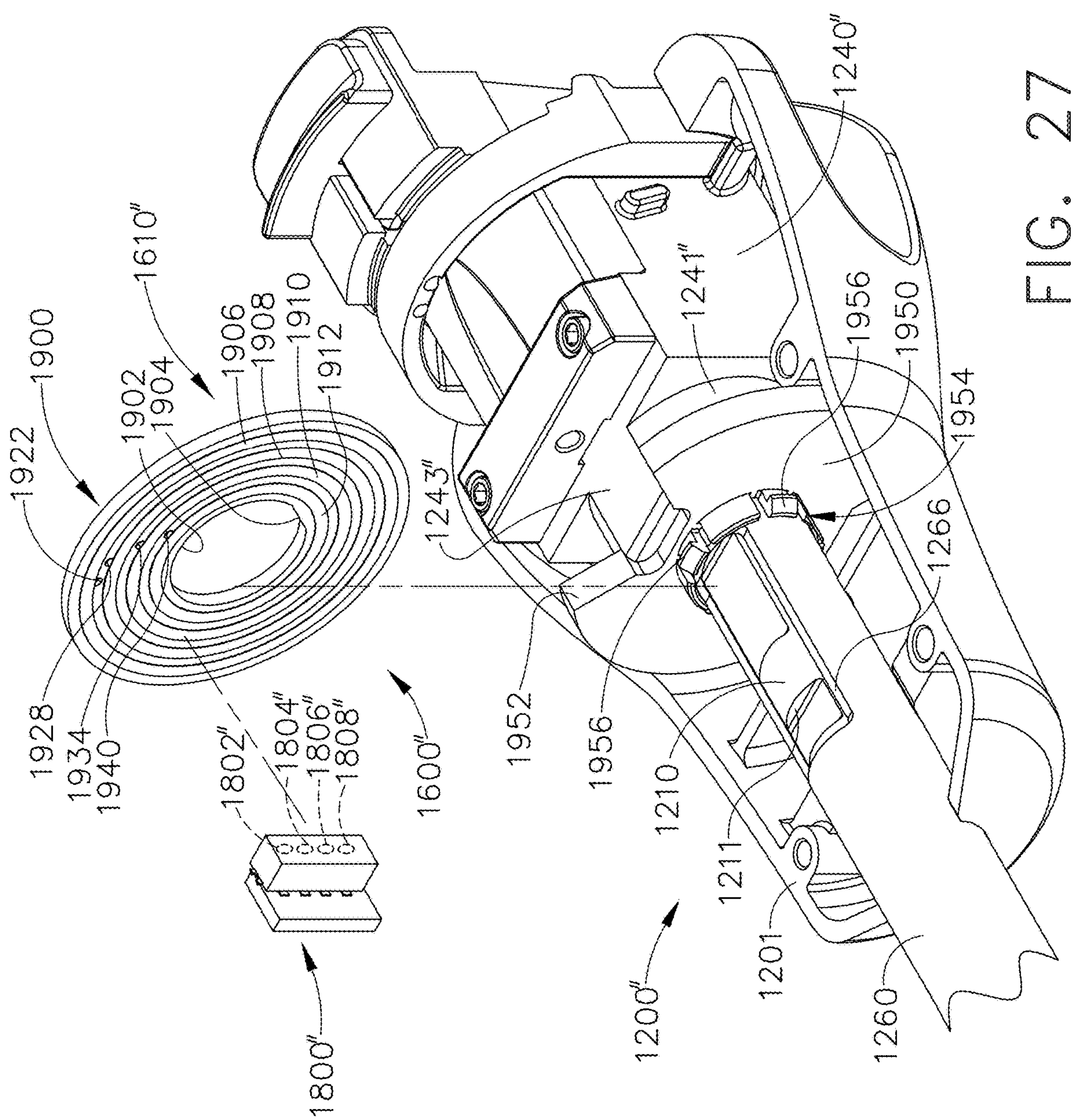
FIG. 27 is an exploded assembly view of portions of the interchangeable shaft assembly and electrical coupler of FIG. 26.

Referring now to FIG. 27, the base ring 1900 is configured to be non-rotatably supported within the nozzle 1201 by a mounting flange 1950 that is non-rotatably coupled to the mounting hub portion 1241" of the chassis 1240". The mounting hub portion 1241" may be formed with a flat surface 1243" for supporting a transverse mounting member of the type, for example, described above that includes a plurality (preferably four) leads that may be coupled to, for example, a circuit board or other corresponding electrical components supported on the chassis in the various manners and arrangements described herein as well as in U.S. patent application Ser. No. 13/803,086, now U.S. Patent Application Publication No. 2014/0263541. The transverse support member has been omitted for clarity in FIGS. 26 and 27. However, as can be seen in FIGS. 26 and 27, the mounting flange 1950 has a notch 1952 therein that is adapted to engage a portion of the flat surface 1243" on the mounting hub portion 1241". As can be seen in FIG. 27, the mounting flange 1950 may further include a flange hub portion 1954 that comprises a series of spring tabs 1956 that serve to fixedly attach the base ring 1900 to the mounting flange 1950. It will be understood that the closure tube 1260 and spine 1210 extend through the flange hub 1954 and are rotatable relative thereto with the nozzle 1201.

In the depicted embodiment for example, the electrical component 1800" is mounted within the nozzle 1201 for rotation about the slip ring assembly 1610" such that, for example, contact 1802" in the component 1800" is in constant electrical contact with rings 1906; contact 1804" is in contact with ring 1908; contact 1806" is in contact with ring 1910; and contact 1808" is in contact with ring 1912 even when the nozzle 1201 is rotated relative to the chassis 1240". It will be understood however, that the various advantages of the slip ring connector 1600" may also be obtained in applications wherein the slip ring assembly 1610" is supported for rotation about the shaft axis SA-SA and the electrical component 1800" is fixedly mounted relative thereto. It will be further appreciated that the slip ring connector 1600" may be effectively employed in connection with a variety of different components and applications outside the field of surgery wherein it is desirable to provide electrical connections between components that rotate relative to each other.

The slip ring connector 1600" comprises a radial slip ring that provides a conductive contact means of passing signal (s) and power to and from any radial position and after shaft rotation. In applications wherein the electrical component comprises a battery contact, the battery contact position can be situated relative to the mounting member to minimize any tolerance stack-up between those components. The slip ring connector 1600" represents a low cost and compact coupling arrangement that can be assembled with minimal manufacturing costs. The unique and novel contact arrangement facilitates complete clockwise and counterclockwise rotation about the shaft axis while remaining in electrical contact with the corresponding annular electrically-conductive rings.

Figure 31:
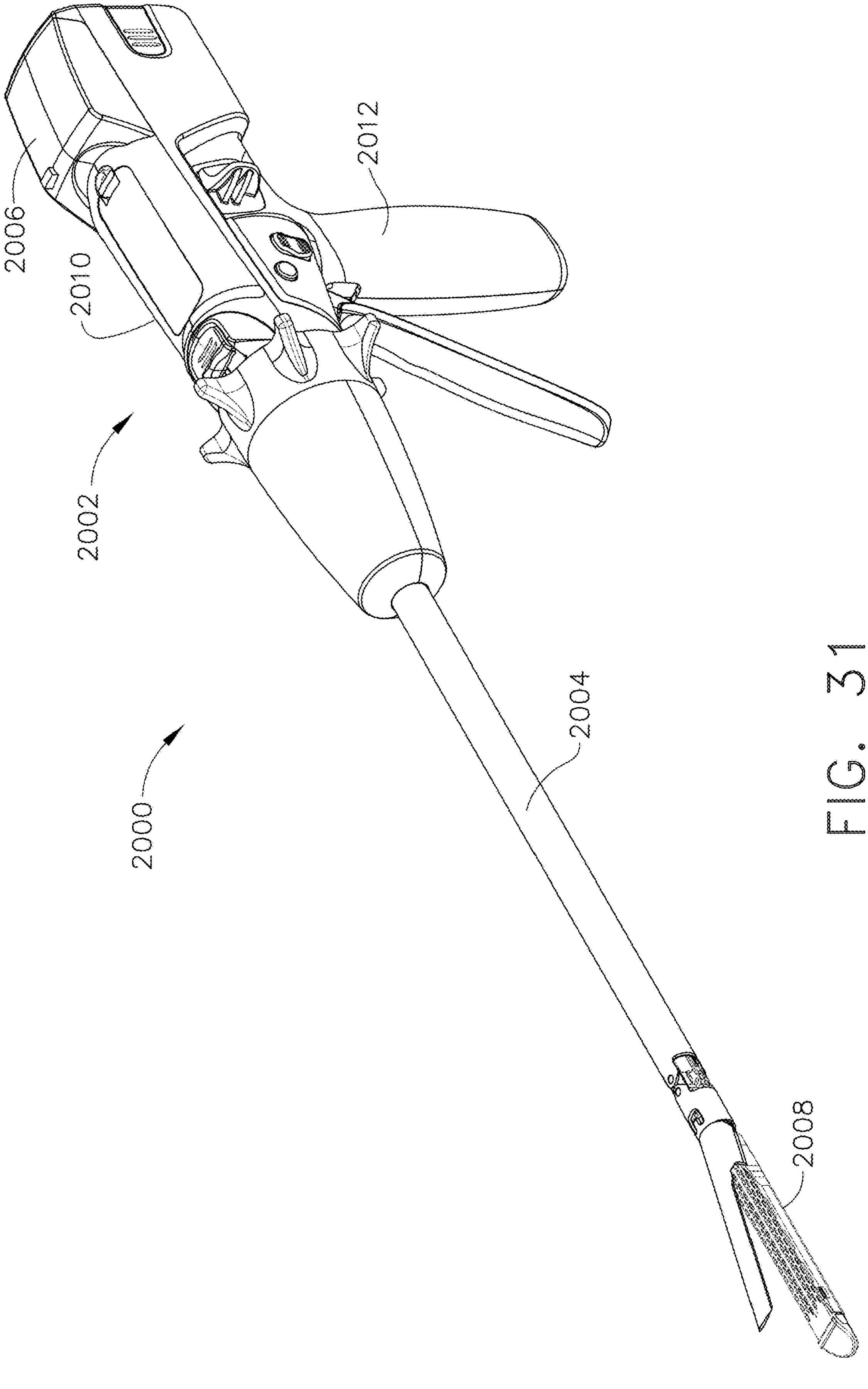
FIG. 31 is a perspective view of a surgical instrument comprising a power assembly, a handle assembly, and an interchangeable shaft assembly.
Figure 32:
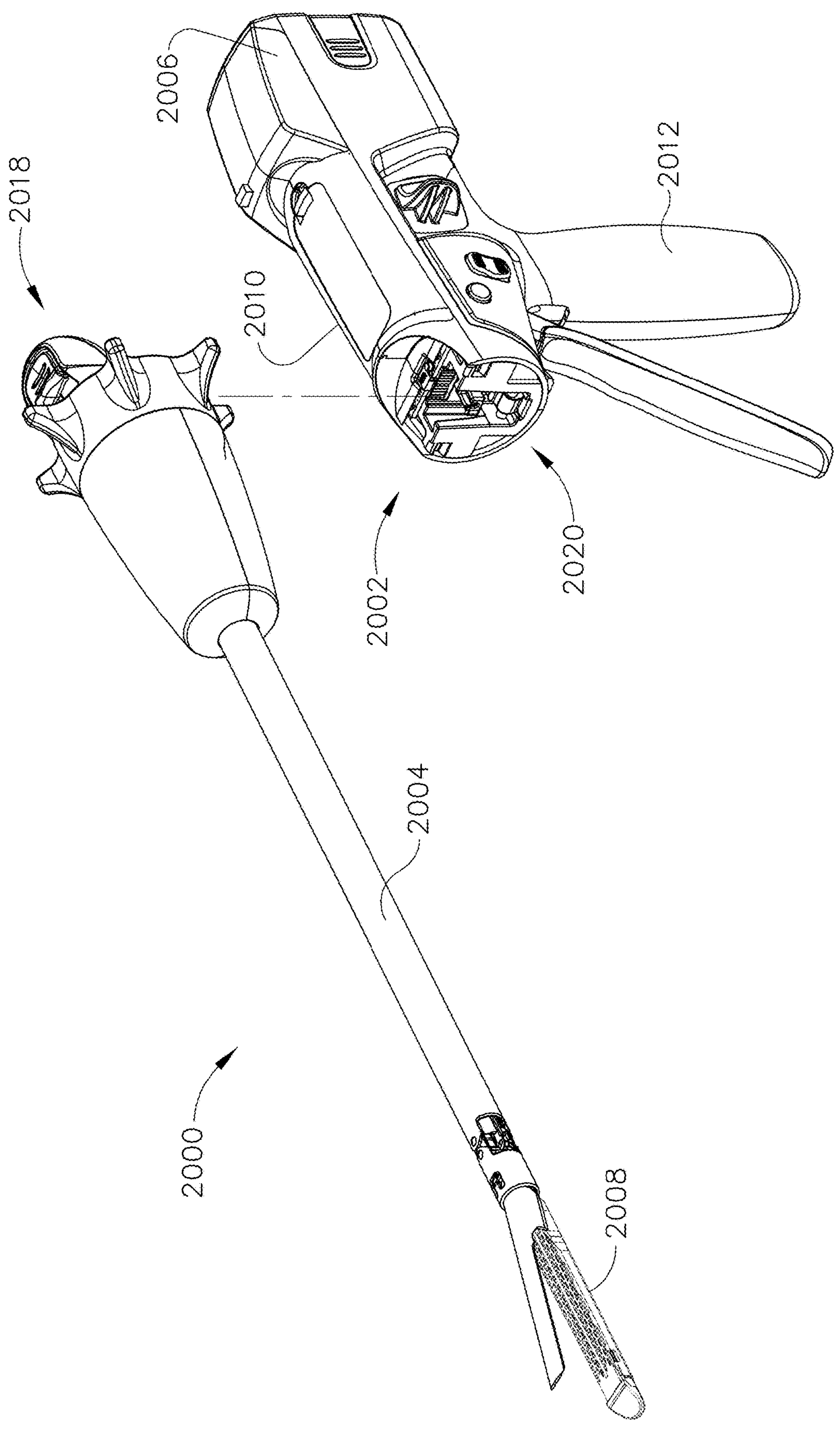
FIG. 32 is perspective view of the surgical instrument of FIG. 31 with the interchangeable shaft assembly separated from the handle assembly.

FIGS. 31-36 generally depict a motor-driven surgical fastening and cutting instrument 2000. As illustrated in FIGS. 31 and 32, the surgical instrument 2000 may include a handle assembly 2002, a shaft assembly 2004, and a power assembly 2006 (or "power source" or "power pack"). The shaft assembly 2004 may include an end effector 2008 which, in certain circumstances, can be configured to act as an endocutter for clamping, severing, and/or stapling tissue, although, in other instances, different types of end effectors may be used, such as end effectors for other types of surgical devices, graspers, cutters, staplers, clip appliers, access devices, drug/gene therapy devices, ultrasound devices, RF device, and/or laser devices, for example. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008. The entire disclosures of U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, are incorporated herein by reference in their entirety.

Figure 33A:
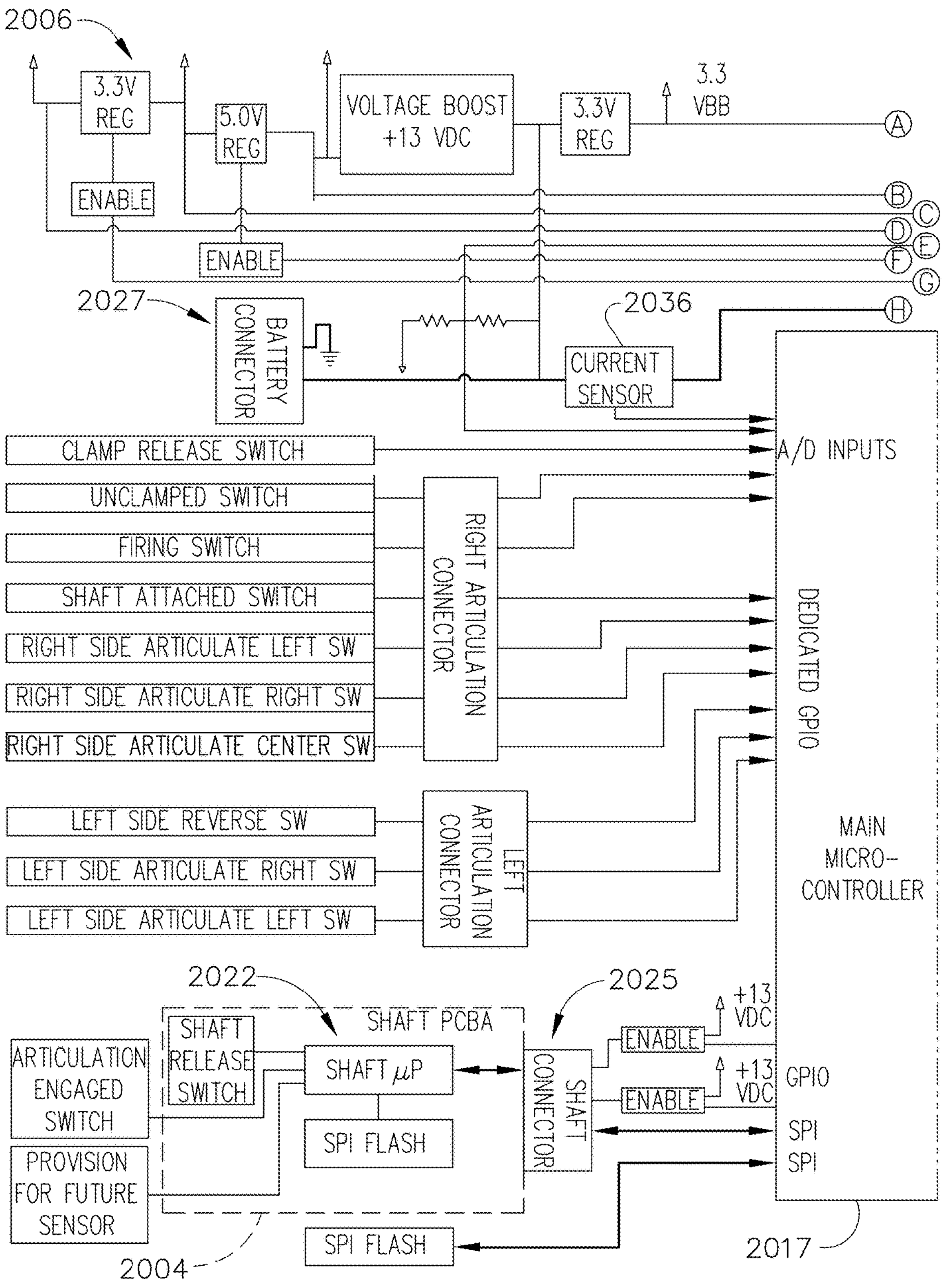
FIGS. 33A and 33B, is a circuit diagram of the surgical instrument of FIG. 31.
Figure 33B:
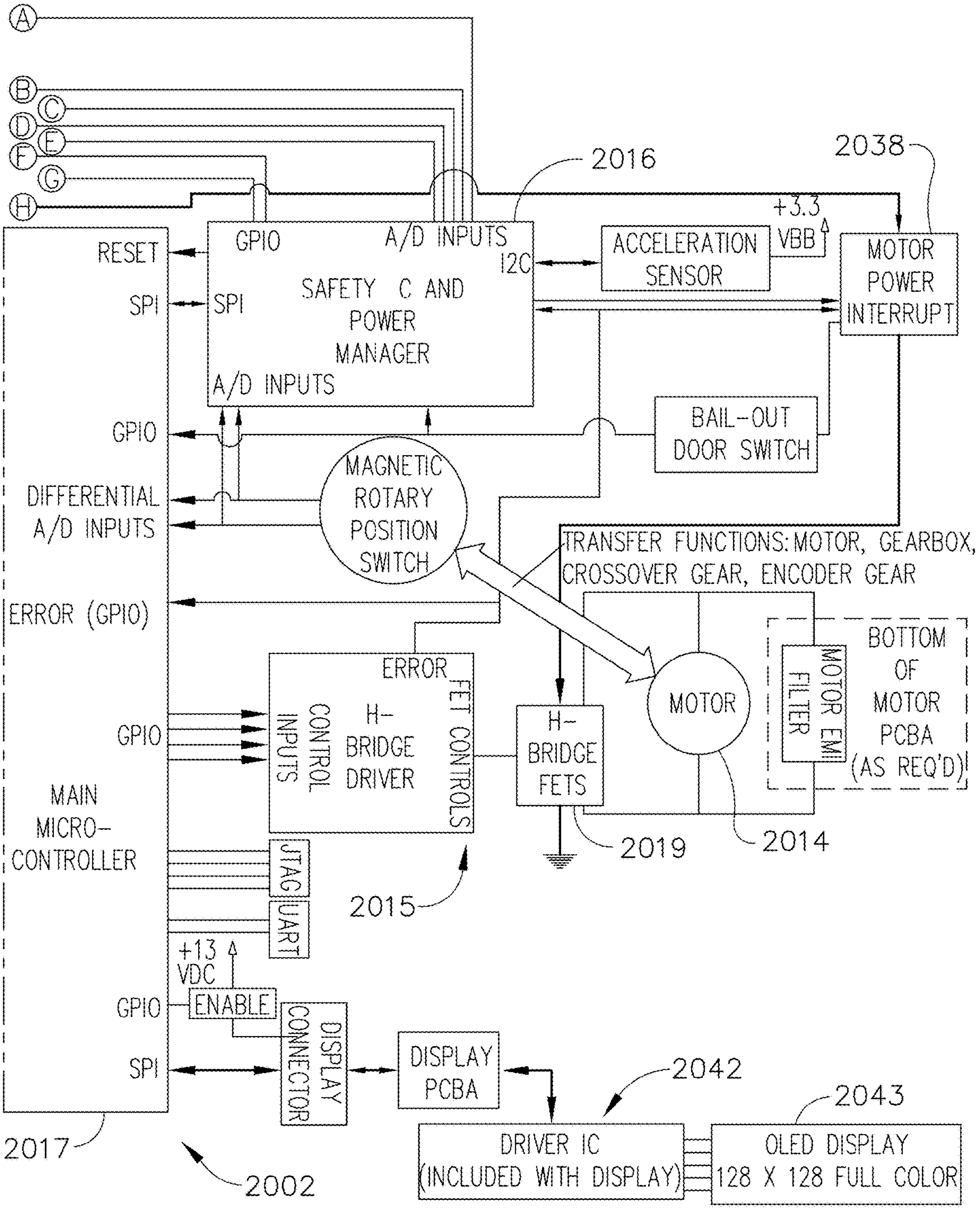

Referring primarily to FIGS. 32, 33A and 33B, the handle assembly 2002 can be employed with a plurality of interchangeable shaft assemblies such as, for example, the shaft assembly 2004. Such interchangeable shaft assemblies may comprise surgical end effectors such as, for example, the end effector 2008 that can be configured to perform one or more surgical tasks or procedures. Examples of suitable interchangeable shaft assemblies are disclosed in U.S. Provisional Patent Application Ser. No. 61/782,866, entitled CONTROL SYSTEM OF A SURGICAL INSTRUMENT, filed Mar. 14, 2013. The entire disclosure of U.S. Provisional Patent Application Ser. No. 61/782,866, entitled CONTROL SYSTEM OF A SURGICAL INSTRUMENT, filed Mar. 14, 2013, is hereby incorporated by reference herein in its entirety.

Referring primarily to FIG. 32, the handle assembly 2002 may comprise a housing 2010 that consists of a handle 2012 that may be configured to be grasped, manipulated and actuated by a clinician. However, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

Referring again to FIG. 32, the handle assembly 2002 may operably support a plurality of drive systems therein that can be configured to generate and apply various control motions to corresponding portions of the interchangeable shaft assembly that is operably attached thereto. For example, the handle assembly 2002 can operably support a first or closure drive system, which may be employed to apply closing and opening motions to the shaft assembly 2004 while operably attached or coupled to the handle assembly 2002. In at least one form, the handle assembly 2002 may operably support a firing drive system that can be configured to apply firing motions to corresponding portions of the interchangeable shaft assembly attached thereto.

Referring primarily to FIGS. 33A and 33B, the handle assembly 2002 may include a motor 2014 which can be controlled by a motor driver 2015 and can be employed by the firing system of the surgical instrument 2000. In various forms, the motor 2014 may be a DC brushed driving motor having a maximum rotation of, approximately, 25,000 RPM, for example. In other arrangements, the motor 2014 may include a brushless motor, a cordless motor, a synchronous motor, a stepper motor, or any other suitable electric motor. In certain circumstances, the motor driver 2015 may comprise an H-Bridge FETs 2019, as illustrated in FIGS. 33A and 33B, for example. The motor 2014 can be powered by the power assembly 2006 (FIG. 35), which can be releasably mounted to the handle assembly 2002, power assembly 2006 being configured to supply control power to the surgical instrument 2000. The power assembly 2006 may comprise a battery 2007 (FIG. 36) which may include a number of battery cells connected in series that can be used as the power source to power the surgical instrument 2000. In such configuration, the power assembly 2006 may be referred to as a battery pack. In certain circumstances, the battery cells of the power assembly 2006 may be replaceable and/or rechargeable. In at least one example, the battery cells can be Lithium-Ion batteries which can be separably couplable to the power assembly 2006.

Examples of drive systems and closure systems that are suitable for use with the surgical instrument 2000 are disclosed in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety. For example, the electric motor 2014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery 2007 (FIG. 36) can operate the electric motor 2014 to drive the longitudinally-movable drive member to effectuate the end effector 2008. For example, the motor 2014 can be configured to drive the longitudinally-movable drive member to advance a firing mechanism to fire staples into tissue captured by the end effector 2008 from a staple cartridge assembled with the end effector 2008 and/or advance a cutting member 2011 (FIG. 34) to cut tissue captured by the end effector 2008, for example.

Figure 35:
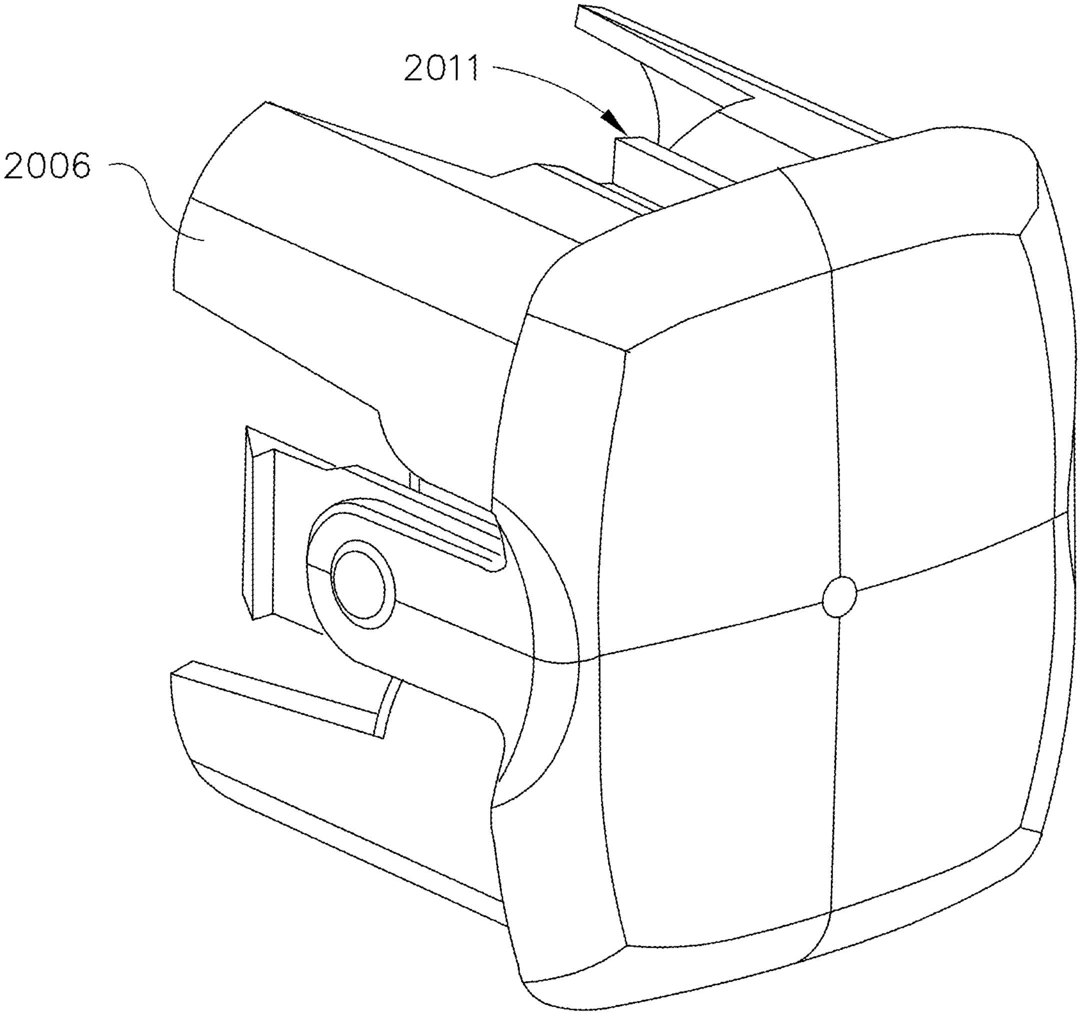
FIG. 35 is a perspective view of the power assembly of the surgical instrument of FIG. 31 separated from the handle assembly.

In certain circumstances, the surgical instrument 2000 may comprise a lockout mechanism to prevent a user from coupling incompatible handle assemblies and power assemblies. For example, as illustrated in FIG. 35, the power assembly 2006 may include a mating element 2011. In certain circumstances, the mating element 2011 can be a tab extending from the power assembly 2006. In certain instances, the handle assembly 2002 may comprise a corresponding mating element (not shown) for mating engagement with the mating element 2011. Such an arrangement can be useful in preventing a user from coupling incompatible handle assemblies and power assemblies.

Figure 34:
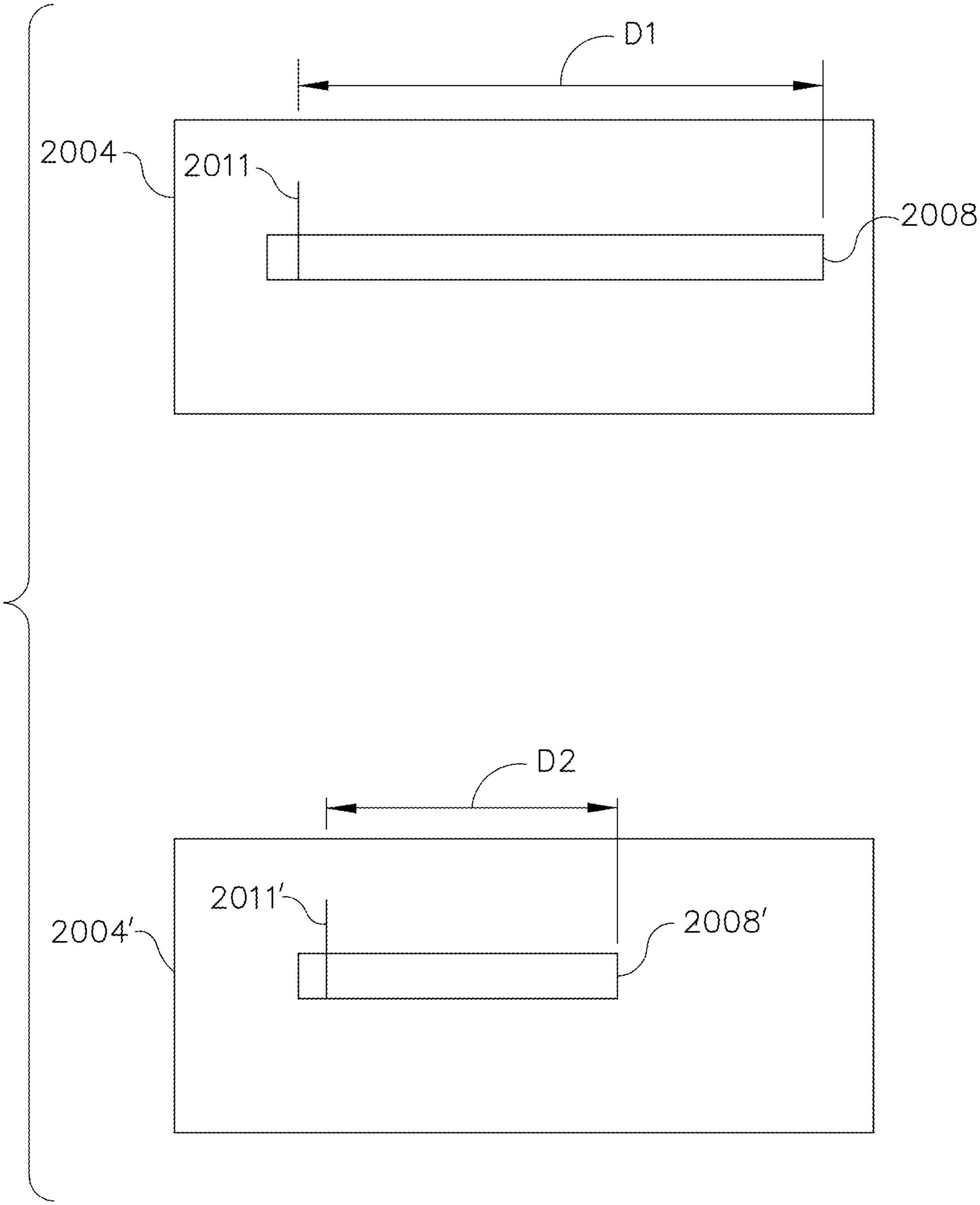
FIG. 34 is a block diagram of interchangeable shaft assemblies for use with the surgical instrument of FIG. 31.

The reader will appreciate that different interchangeable shaft assemblies may possess different power requirements. The power required to advance a cutting member through an end effector and/or to fire staples may depend, for example, on the distance traveled by the cutting member, the staple cartridge being used, and/or the type of tissue being treated. That said, the power assembly 2006 can be configured to meet the power requirements of various interchangeable shaft assemblies. For example, as illustrated in FIG. 34, the cutting member 2011 of the shaft assembly 2004 can be configured to travel a distance D1 along the end effector 2008. On the other hand, another interchangeable shaft assembly 2004' may include a cutting member 2011' which can be configured to travel a distance D2, different from the distance D1, along an end effector 2008' of the interchangeable shaft assembly 2004'. The power assembly 2006 can be configured to provide a first power output sufficient to power the motor 2014 to advance the cutting member 2011 the distance D1 while the interchangeable shaft assembly 2004 is coupled to the handle assembly 2002 and can be configured to provide a second power output, different from the first power output, which is sufficient to power the motor 2014 to advance the cutting member 2011' the distance D2 while the interchangeable shaft assembly 2004' is coupled to the handle assembly 2002, for example. As illustrated in FIGS. 33A and 33B and as described below in greater detail, the power assembly 2006 may include a power management controller 2016 (FIG. 36) which can be configured to modulate the power output of the power assembly 2006 to deliver a first power output to power the motor 2014 to advance the cutting member 2011 the distance D1 while the interchangeable shaft assembly 2004 is coupled to the handle assembly 2002 and to deliver a second power output to power the motor 2014 to advance the cutting member 2011' the distance D2 while the interchangeable shaft assembly 2004' is coupled to the handle assembly 2002, for example. Such modulation can be beneficial in avoiding transmission of excessive power to the motor 2014 beyond the requirements of an interchangeable shaft assembly that is coupled to the handle assembly 2002.

Referring again to FIGS. 32-36, the handle assembly 2002 can be releasably coupled or attached to an interchangeable shaft assembly such as, for example, the shaft assembly 2004. In certain instances, the handle assembly 2002 can be releasably coupled or attached to the power assembly 2006. Various coupling means can be utilized to releasably couple the handle assembly 2002 to the shaft assembly 2004 and/or to the power assembly 2006. Exemplary coupling mechanisms are described in U.S. Provisional Patent Application Ser. No. 61/782,866, entitled CONTROL SYSTEM OF A SURGICAL INSTRUMENT, and filed Mar. 14, 2013. For example, the shaft assembly 2004 may include a shaft attachment module 2018 (FIG. 32) which may further include a latch actuator assembly that may be configured to cooperate with a lock yoke that is pivotally coupled to the shaft attachment module 2018 for selective pivotal travel relative thereto, wherein the lock yoke may include proximally protruding lock lugs that are configured for releasable engagement with corresponding lock detents or grooves formed in a hand assembly attachment module 2020 of the handle assembly 2002.

Referring now primarily to FIGS. 33A-36, the shaft assembly 2004 may include a shaft assembly controller 2022 which can communicate with the power management controller 2016 through an interface 2024 while the shaft assembly 2004 and the power assembly 2006 are coupled to the handle assembly 2002. For example, the interface 2024 may comprise a first interface portion 2025 which may include one or more electric connectors 2026 for coupling engagement with corresponding shaft assembly electric connectors 2028 and a second interface portion 2027 which may include one or more electric connectors 2030 for coupling engagement with corresponding power assembly electric connectors 2032 to permit electrical communication between the shaft assembly controller 2022 and the power management controller 2016 while the shaft assembly 2004 and the power assembly 2006 are coupled to the handle assembly 2002. One or more communication signals can be transmitted through the interface 2024 to communicate one or more of the power requirements of the attached interchangeable shaft assembly 2004 to the power management controller 2016. In response, the power management controller may modulate the power output of the battery 2007 of the power assembly 2006, as described below in greater detail, in accordance with the power requirements of the attached shaft assembly 2004. In certain circumstances, one or more of the electric connectors 2026, 2028, 2030, and/or 2032 may comprise switches which can be activated after mechanical coupling engagement of the handle assembly 2002 to the shaft assembly 2004 and/or to the power assembly 2006 to allow electrical communication between the shaft assembly controller 2022 and the power management controller 2016.

In certain circumstances, the interface 2024 can facilitate transmission of the one or more communication signals between the power management controller 2016 and the shaft assembly controller 2022 by routing such communication signals through a main controller 2017 (FIGS. 33A and 33B) residing in the handle assembly 2002, for example. In other circumstances, the interface 2024 can facilitate a direct line of communication between the power management controller 2016 and the shaft assembly controller 2022 through the handle assembly 2002 while the shaft assembly 2004 and the power assembly 2006 are coupled to the handle assembly 2002.

In one instance, the main microcontroller 2017 may be any single core or multicore processor such as those known under the trade name ARM Cortex by Texas Instruments. In one instance, the surgical instrument 2000 may comprise a power management controller 2016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 1004 may be configured specifically for IEC 61508 and ISO 26262 safety critical applications, among others, to provide advanced integrated safety features while delivering scalable performance, connectivity, and memory options.

In certain instances, the microcontroller 2017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Figure 36:
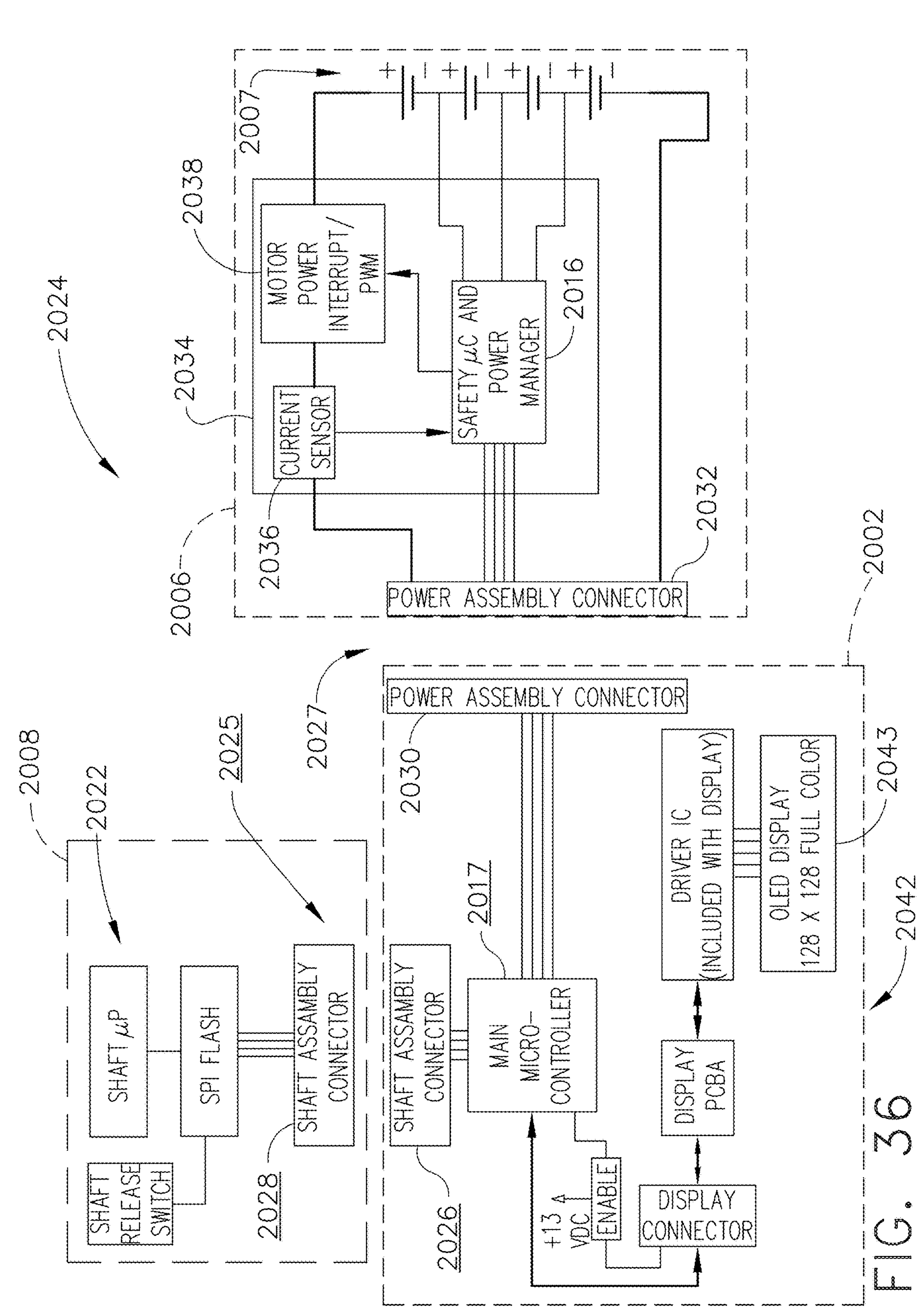
FIG. 36 is a block diagram the surgical instrument of FIG. 31 illustrating interfaces between the handle assembly and the power assembly and between the handle assembly and the interchangeable shaft assembly.
Figure 37:
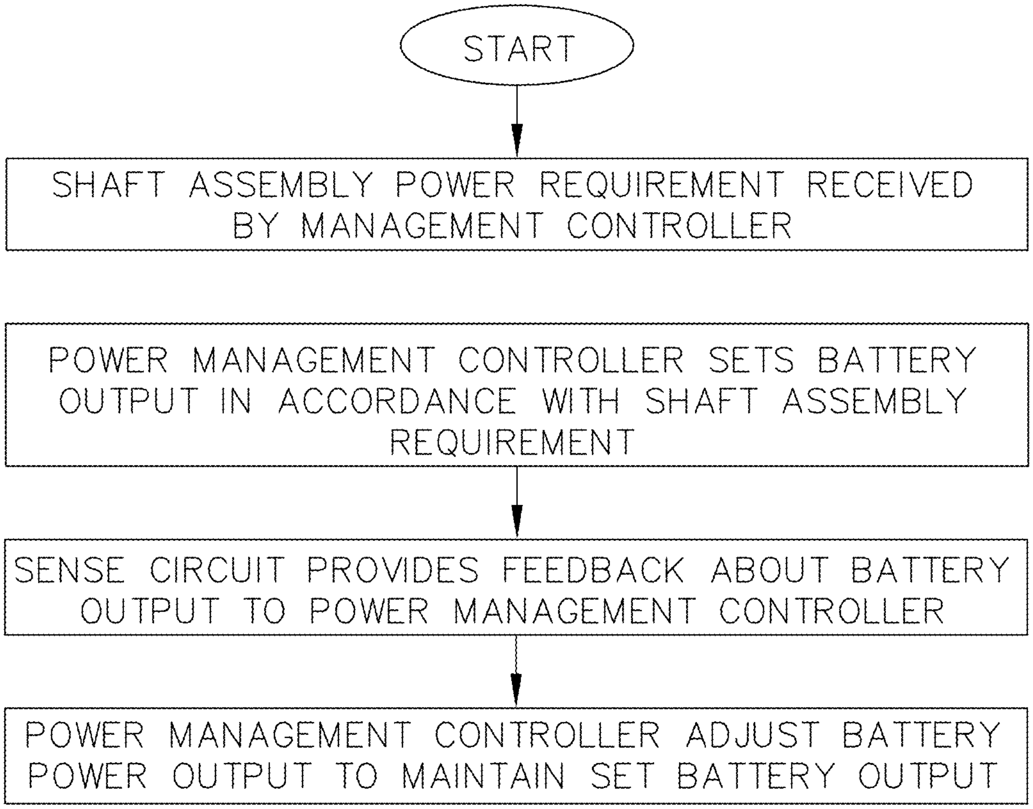
FIG. 37 is a power management module of the surgical instrument of FIG. 31.

Referring now primarily to FIGS. 36 and 37, the power assembly 2006 may include a power management circuit 2034 which may comprise the power management controller 2016, a power modulator 2038, and a current sense circuit 2036. The power management circuit 2034 can be configured to modulate power output of the battery 2007 based on the power requirements of the shaft assembly 2004 while the shaft assembly 2004 and the power assembly 2006 are coupled to the handle assembly 2002. For example, the power management controller 2016 can be programmed to control the power modulator 2038 of the power output of the power assembly 2006 and the current sense circuit 2036 can be employed to monitor power output of the power assembly 2006 to provide feedback to the power management controller 2016 about the power output of the battery 2007 so that the power management controller 2016 may adjust the power output of the power assembly 2006 to maintain a desired output, as illustrated in FIG. 37.

It is noteworthy that the power management controller 2016 and/or the shaft assembly controller 2022 each may comprise one or more processors and/or memory units which may store a number of software modules. Although certain modules and/or blocks of the surgical instrument 2000 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 2000 may comprise an output device 2042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 2042 may comprise a display 2043 which may be included in the handle assembly 2002, as illustrated in FIG. 36. The shaft assembly controller 2022 and/or the power management controller 2016 can provide feedback to a user of the surgical instrument 2000 through the output device 2042. The interface 2024 can be configured to connect the shaft assembly controller 2022 and/or the power management controller 2016 to the output device 2042. The reader will appreciate that the output device 2042 can instead be integrated with the power assembly 2006. In such circumstances, communication between the output device 2042 and the shaft assembly controller 2022 may be accomplished through the interface 2024 while the shaft assembly 2004 is coupled to the handle assembly 2002.

Figure 38:
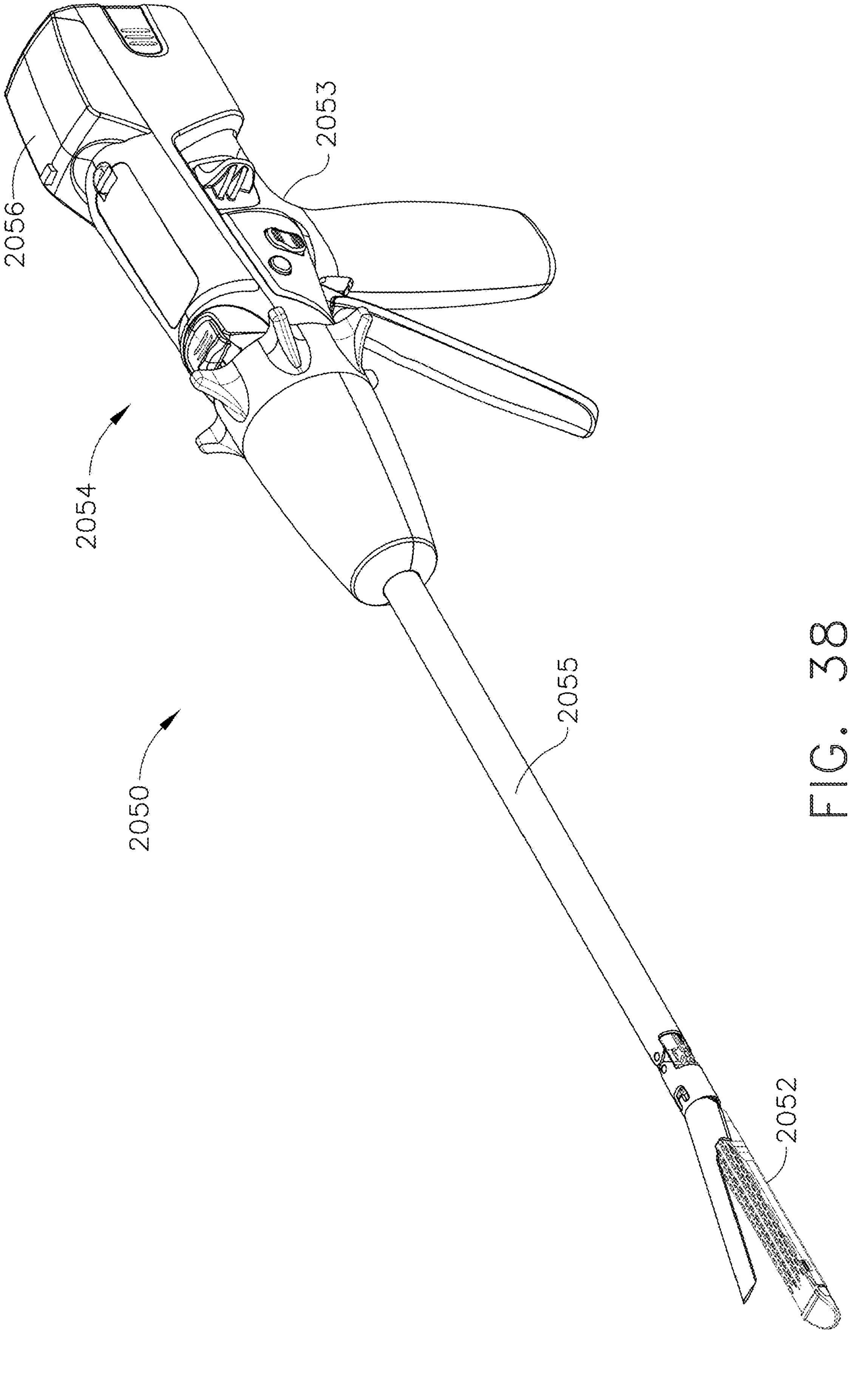
FIG. 38 is a perspective view of a surgical instrument comprising a power assembly and an interchangeable working assembly assembled with the power assembly.
Figure 39:
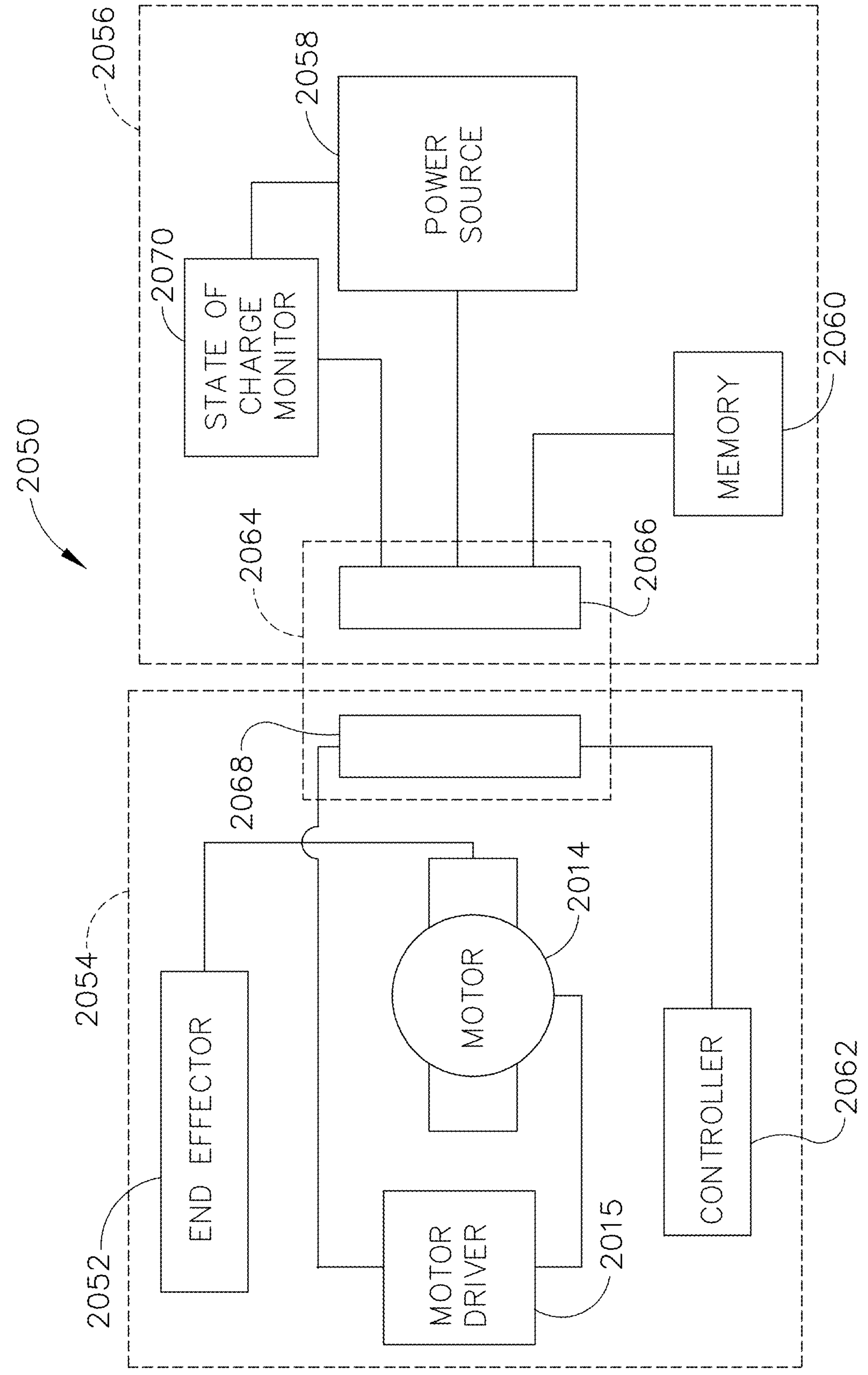
FIG. 39 is a block diagram of the surgical instrument of FIG. 38 illustrating an interface between the interchangeable working assembly and the power assembly.

Referring to FIGS. 38 and 39, a surgical instrument 2050 is illustrated. The surgical instrument 2050 is similar in many respects to the surgical fastening and cutting instrument 2000 (FIG. 31). For example, the surgical instrument 2050 may include an end effector 2052 which is similar in many respects to the end effector 2008. For example, the end effector 2052 can be configured to act as an endocutter for clamping, severing, and/or stapling tissue.

Further to the above, the surgical instrument 2050 may include an interchangeable working assembly 2054 which may include a handle assembly 2053 and a shaft 2055 extending between the handle assembly 2053 and the end effector 2052, as illustrated in FIG. 38. In certain instances, the surgical instrument 2050 may include a power assembly 2056 which can be employed with a plurality of interchangeable working assemblies such as, for example, the interchangeable working assembly 2054. Such interchangeable working assemblies may include surgical end effectors such as, for example, the end effector 2052 that can be configured to perform one or more surgical tasks or procedures. In certain circumstances, the handle assembly 2053 and the shaft 2055 may be integrated into a single unit. In other circumstances, the handle assembly 2053 and the shaft 2055 may be separably couplable to each other.

Similar to the surgical instrument 2000, the surgical instrument 2050 may operably support a plurality of drive systems which can be powered by the power assembly 2056 while the power assembly 2056 is coupled to the interchangeable working assembly 2054. For example, the interchangeable working assembly 2054 can operably support a closure drive system, which may be employed to apply closing and opening motions to the end effector 2052. In at least one form, the interchangeable working assembly 2054 may operably support a firing drive system that can be configured to apply firing motions to the end effector 2052. Examples of drive systems suitable for use with the surgical instrument 2050 are described in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety.

Referring to FIG. 39, the power assembly 2056 of the surgical instrument 2050 can be separably coupled to an interchangeable working assembly such as, for example, the interchangeable working assembly 2054. Various coupling means can be utilized to releasably couple the power assembly 2056 to the interchangeable working assembly 2054. Exemplary coupling mechanisms are described herein and are described in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety.

Still referring to FIG. 39, the power assembly 2056 may include a power source 2058 such as, for example, a battery which can be configured to power the interchangeable working assembly 2054 while coupled to the power assembly 2056. In certain instances, the power assembly 2056 may include a memory 2060 which can be configured to receive and store information about the battery 2058 and/or the interchangeable working assembly 2054 such as, for example, the state of charge of the battery 2058, the number of treatment cycles performed using the battery 2058, and/or identification information for the interchangeable working assemblies coupled to the power assembly 2056 during the life cycle of the battery 2058. Further to the above, the interchangeable working assembly 2054 may include a controller 2062 which can be configured to provide the memory 2060 with such information about the battery 2058 and/or the interchangeable working assembly 2054.

Still referring to FIG. 39, the power assembly 2056 may include an interface 2064 which can be configured to facilitate electrical communication between the memory 2060 of the power assembly 2056 and a controller of an interchangeable working assembly that is coupled to the power assembly 2056 such as, for example, the controller 2062 of the interchangeable working assembly 2054. For example, the interface 2064 may comprise one or more connectors 2066 for coupling engagement with corresponding working assembly connectors 2068 to permit electrical communication between the controller 2062 and the memory 2060 while the interchangeable working assembly 2054 is coupled to the power assembly 2056. In certain circumstances, one or more of the electric connectors 2066 and/or 2068 may comprise switches which can be activated after coupling engagement of the interchangeable working assembly 2054 and the power assembly 2056 to allow electric communication between the controller 2062 and the memory 2060.

Still referring to FIG. 39, the power assembly 2056 may include a state of charge monitoring circuit 2070. In certain circumstances, the state of charge monitoring circuit 2070 may comprise a coulomb counter. The controller 2062 can be in communication with the state of charge monitoring circuit 2070 while the interchangeable working assembly 2054 is coupled to the power assembly 2056. The state of charge monitoring circuit 2070 can be operable to provide for accurate monitoring of charge states of the battery 2058.

Figure 40:
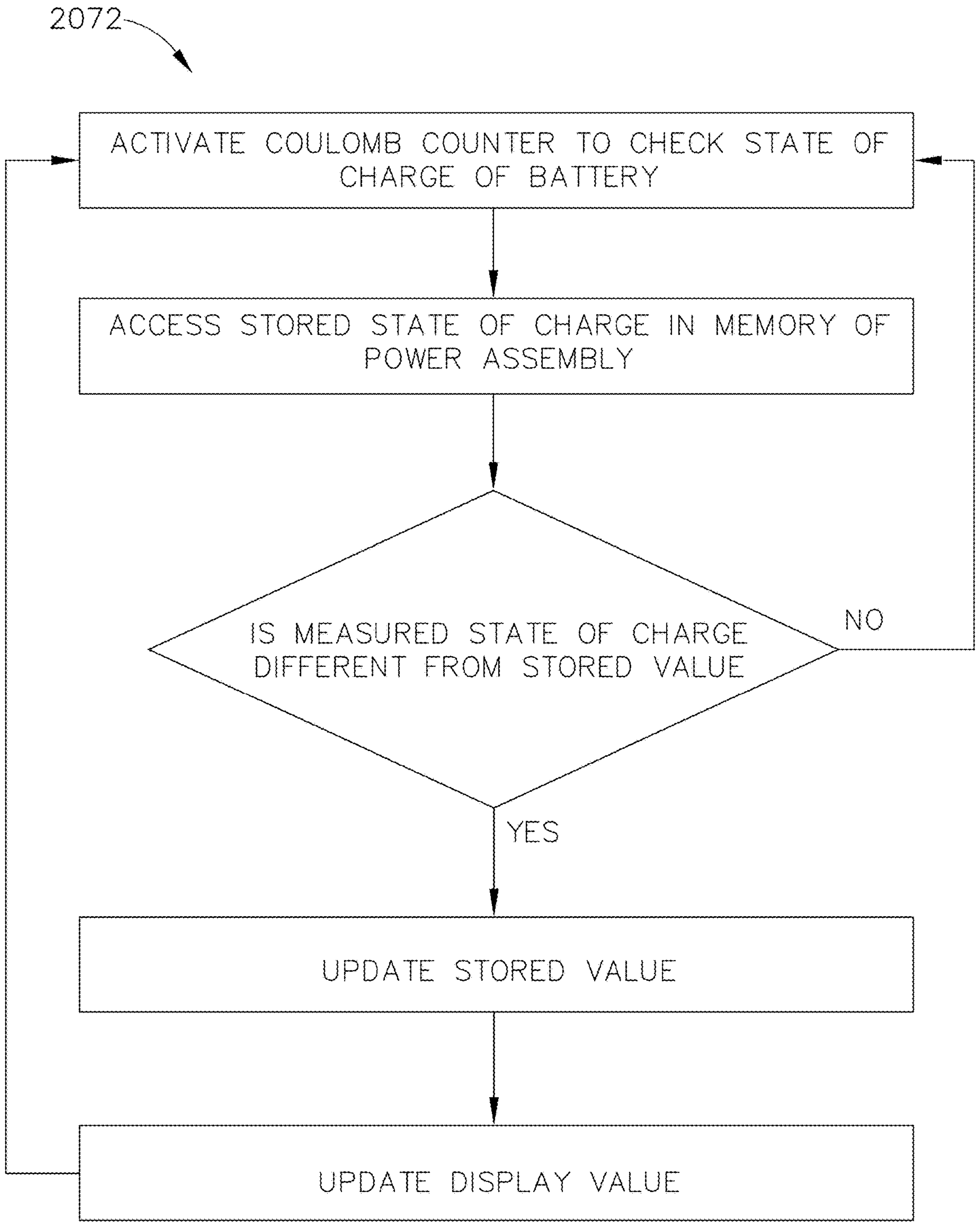
FIG. 40 is a block diagram illustrating a module of the surgical instrument of FIG. 38.

FIG. 40 depicts an exemplary module 2072 for use with a controller of an interchangeable working assembly such as, for example, the controller 2062 of the interchangeable working assembly 2054 while coupled to the power assembly 2056. For example, the controller 2062 may comprise one or more processors and/or memory units which may store a number of software modules such as, for example, the module 2072. Although certain modules and/or blocks of the surgical instrument 2050 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

In any event, upon coupling the interchangeable working assembly 2054 to the power assembly 2056, the interface 2064 may facilitate communication between the controller 2062 and the memory 2060 and/or the state of charge monitoring circuit 2070 to execute the module 2072, as illustrated in FIG. 40. For example, the controller 2062 of the interchangeable working assembly 2054 may utilize the state of charge monitoring circuit 2070 to measure the state of charge of the battery 2058. The controller 2062 may then access the memory 2060 and determine whether a previous value for the state of charge of the battery 2058 is stored in the memory 2060. When a previous value is detected, the controller 2060 may compare the measured value to the previously stored value. When the measured value is different from the previously stored value, the controller 2060 may update the previously stored value. When no value is previously recorded, the controller 2060 may store the measured value into the memory 2060. In certain circumstances, the controller 2060 may provide visual feedback to a user of the surgical instrument 2050 as to the measured state of charge of the battery 2058. For example, the controller 2060 may display the measured value of the state of charge of the battery 2058 on an LCD display screen which, in some circumstances, can be integrated with the interchangeable working assembly 2054.

Further to the above, the module 2072 also can be executed by other controllers upon coupling the interchangeable working assemblies of such other controllers to the power assembly 2056. For example, a user may disconnect the interchangeable working assembly 2054 from the power assembly 2056. The user may then connect another interchangeable working assembly comprising another controller to the power assembly 2056. Such controller may in turn utilize the coulomb counting circuit 2070 to measure the state of charge of the battery 2058 and may then access the memory 2060 and determine whether a previous value for the state of charge of the battery 2058 is stored in the memory 2060 such as, for example, a value entered by the controller 2060 while the interchangeable working assembly 2054 was coupled to the power assembly 2056. When a previous value is detected, the controller may compare the measured value to the previously stored value. When the measured value is different from the previously stored value, the controller may update the previously stored value.

Figure 41:
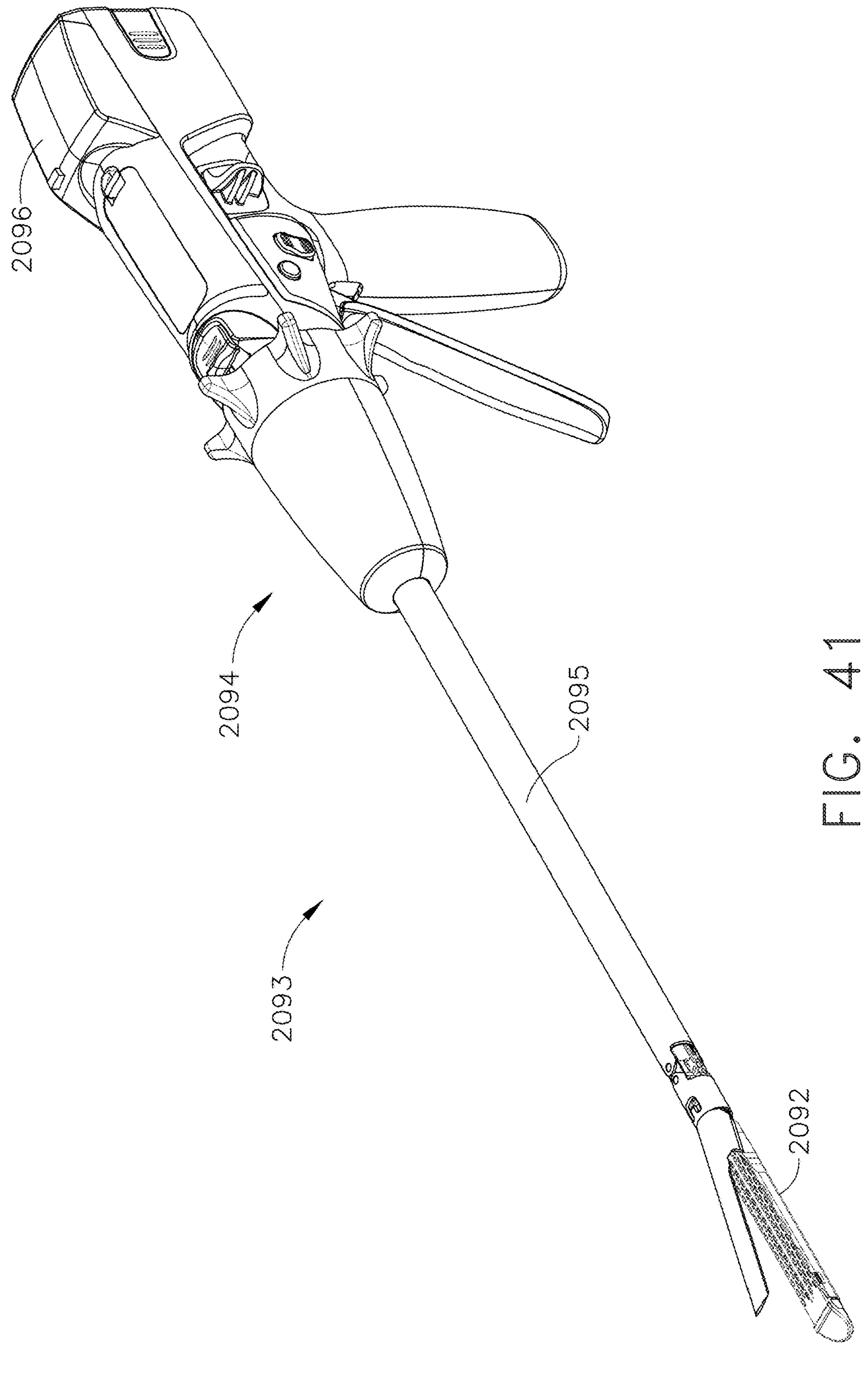
FIG. 41 is a perspective view of a surgical instrument comprising a power assembly and a interchangeable working assembly assembled with the power assembly.

FIG. 41 depicts a surgical instrument 2090 which is similar in many respects to the surgical instrument 2000 (FIG. 31) and/or the surgical instrument 2050 (FIG. 38). For example, the surgical instrument 2090 may include an end effector 2092 which is similar in many respects to the end effector 2008 and/or the end effector 2052. For example, the end effector 2092 can be configured to act as an endocutter for clamping, severing, and/or stapling tissue.

Further to the above, the surgical instrument 2090 may include an interchangeable working assembly 2094 which may include a handle assembly 2093 and a shaft 2095 which may extend between the handle assembly 2093 and the end effector 2092. In certain instances, the surgical instrument 2090 may include a power assembly 2096 which can be employed with a plurality of interchangeable working assemblies such as, for example, the interchangeable working assembly 2094. Such interchangeable working assemblies may comprise surgical end effectors such as, for example, the end effector 2092 that can be configured to perform one or more surgical tasks or procedures. In certain circumstances, the handle assembly 2093 and the shaft 2095 may be integrated into a single unit. In other circumstances, the handle assembly 2093 and the shaft 2095 can be separably couplable to each other.

Furthermore, the power assembly 2096 of the surgical instrument 2090 can be separably couplable to an interchangeable working assembly such as, for example, the interchangeable working assembly 2094. Various coupling means can be utilized to releasably couple the power assembly 2096 to the interchangeable working assembly 2094. Similar to the surgical instrument 2050 and/or the surgical instrument 2000, the surgical instrument 2090 may operably support one or more drive systems which can be powered by the power assembly 2096 while the power assembly 2096 is coupled to the interchangeable working assembly 2094. For example, the interchangeable working assembly 2094 may operably support a closure drive system, which may be employed to apply closing and/or opening motions to the end effector 2092. In at least one form, the interchangeable working assembly 2094 may operably support a firing drive system that can be configured to apply firing motions to the end effector 2092. Exemplary drive systems and coupling mechanisms for use with the surgical instrument 2090 are described in greater detail U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety.

Figure 42:
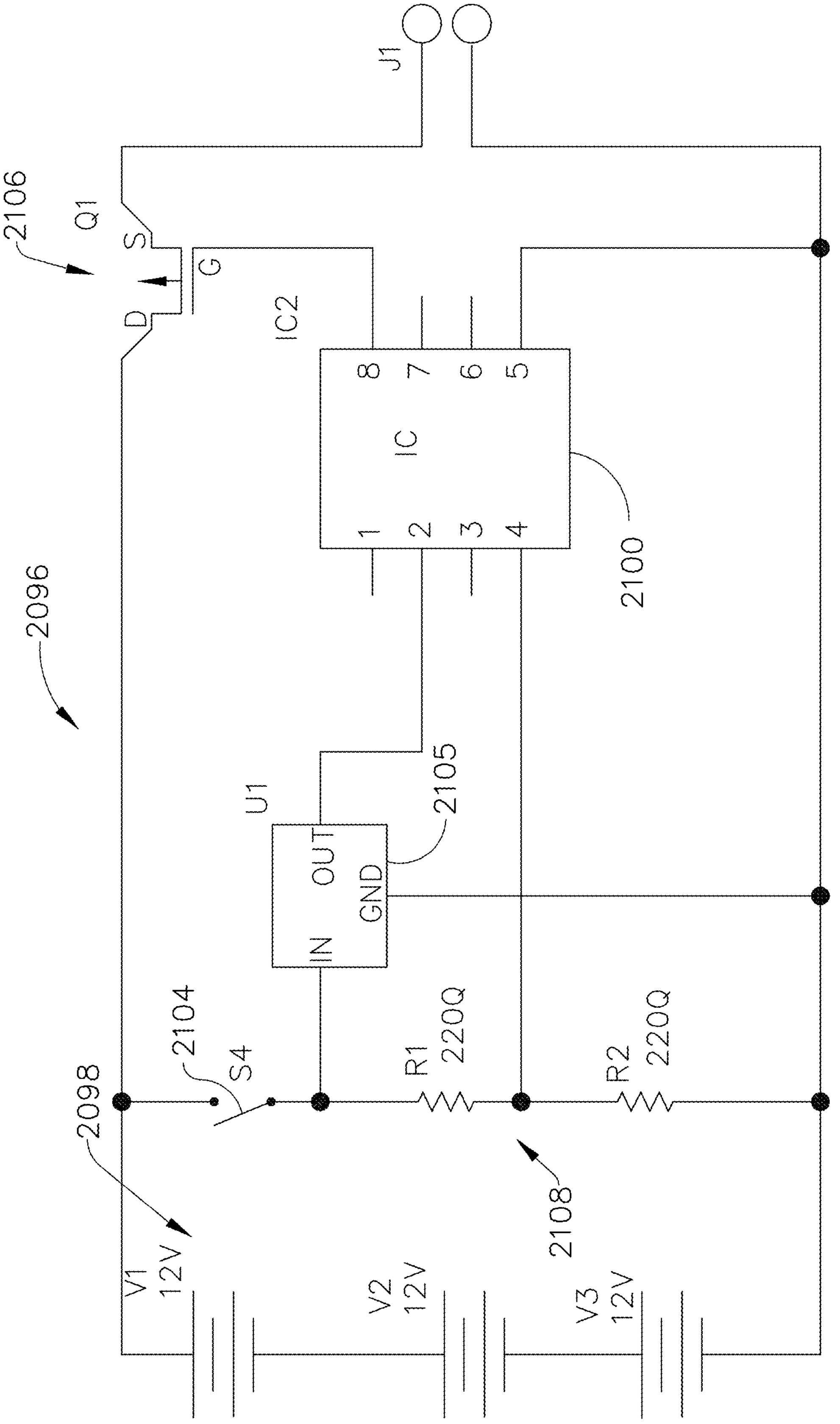
FIG. 42 is a circuit diagram of an exemplary power assembly of the surgical instrument of FIG. 41.
Figure 43:
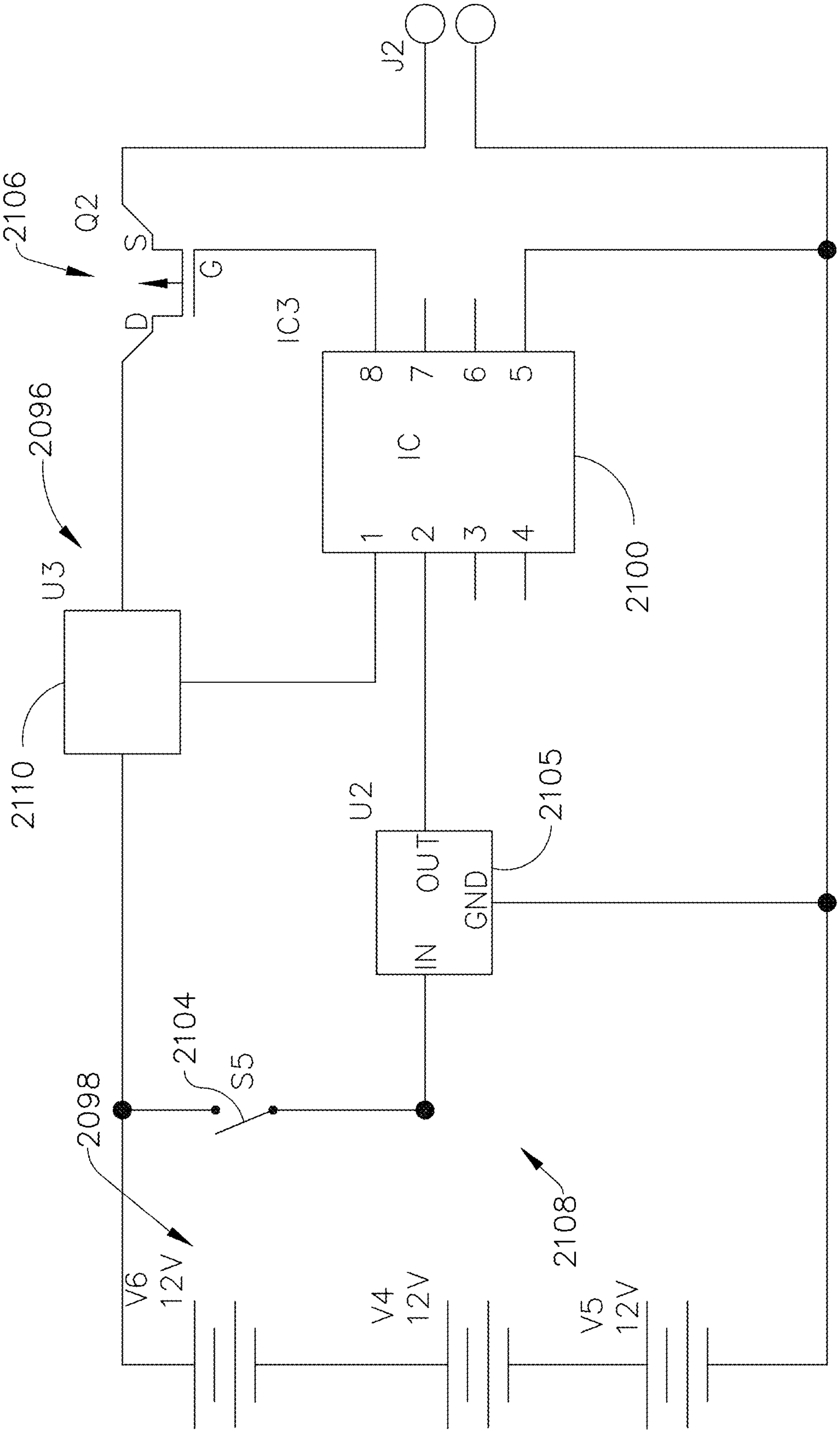
FIG. 43 is a circuit diagram of an exemplary power assembly of the surgical instrument of FIG. 41.

Referring to FIGS. 41-45, the interchangeable working assembly 2094 may include a motor such as, for example, the motor 2014 (FIG. 44) and a motor driver such as, for example, the motor driver 2015 (FIG. 44) which can be employed to motivate the closure drive system and/or the firing drive system of the interchangeable working assembly 2094, for example. The motor 2014 can be powered by a battery 2098 (FIG. 42) which may reside in the power assembly 2096. As illustrated in FIGS. 42 and 43, the battery 2098 may include a number of battery cells connected in series that can be used as a power source to power the motor 2014. In certain instances, the battery cells of the power assembly 2096 may be replaceable and/or rechargeable. The battery cells can be Lithium-Ion batteries which can be separably couplable to the power assembly 2096, for example. In use, a voltage polarity provided by the power assembly 2096 can operate the motor 2014 to drive a longitudinally-movable drive member to effectuate the end effector 2092. For example, the motor 2014 can be configured to drive the longitudinally-movable drive member to advance a cutting member to cut tissue captured by the end effector 2092 and/or a firing mechanism to fire staples from a staple cartridge assembled with the end effector 2092, for example. The staples can be fired into tissue captured by the end effector 2092, for example.

Referring now to FIGS. 41-45, the interchangeable working assembly 2094 may include a working assembly controller 2102 (FIGS. 44 and 45) and the power assembly 2096 may include a power assembly controller 2100 (FIGS. 42 and 43). The working assembly controller 2102 can be configured to generate one or more signals to communicate with the power assembly controller 2100. In certain instances, the working assembly controller 2102 may generate the one or more signals to communicate with the power assembly controller 2100 by modulating power transmission from the power assembly 2096 to the interchangeable working assembly 2094 while the power assembly 2096 is coupled to the interchangeable working assembly 2094.

Furthermore, the power assembly controller 2100 can be configured to perform one or more functions in response to receiving the one or more signals generated by the working assembly controller 2102. For example, the interchangeable working assembly 2094 may comprise a power requirement and the working assembly controller 2102 may be configured to generate a signal to instruct the power assembly controller 2100 to select a power output of the battery 2098 in accordance with the power requirement of the interchangeable working assembly 2094; the signal can be generated, as described above, by modulating power transmission from the power assembly 2096 to the interchangeable working assembly 2094 while the power assembly 2096 is coupled to the interchangeable working assembly 2094. In response to receiving the signal, the power assembly controller 2100 may set the power output of the battery 2098 to accommodate the power requirement of the interchangeable working assembly 2094. The reader will appreciate that various interchangeable working assemblies may be utilized with the power assembly 2096. The various interchangeable working assemblies may comprise various power requirements and may generate signals unique to their power requirements during their coupling engagement with the power assembly 2096 to alert the power assembly controller 2100 to set the power output of the battery 2098 in accordance with their power requirements.

Referring now primarily to FIGS. 42 and 43, the power assembly 2096 may include a power modulator control 2106 which may comprise, for example, one or more field-effect transistors (FETs), a Darlington array, an adjustable amplifier, and/or any other power modulator. The power assembly controller 2100 may actuate the power modulator control 2106 to set the power output of the battery 2098 to the power requirement of the interchangeable working assembly 2094 in response to the signal generated by working assembly controller 2102 while the interchangeable working assembly 2094 is coupled to the power assembly 2096.

Still referring primarily to FIGS. 42 and 43, the power assembly controller 2100 can be configured to monitor power transmission from the power assembly 2096 to the interchangeable working assembly 2094 for the one or more signals generated by the working assembly controller 2102 of the interchangeable working assembly 2094 while he interchangeable working assembly 2094 is coupled to the power assembly 2096. As illustrated in FIG. 42, the power assembly controller 2100 may utilize a voltage monitoring mechanism for monitoring the voltage across the battery 2098 to detect the one or more signals generated by the working assembly controller 2102, for example. In certain instances, a voltage conditioner can be utilized to scale the voltage of the battery 2098 to be readable by an Analog to Digital Converter (ADC) of the power assembly controller 2100. As illustrated in FIG. 42, the voltage conditioner may comprise a voltage divider 2108 which can create a reference voltage or a low voltage signal proportional to the voltage of the battery 2098 which can be measured and reported to the power assembly controller 2100 through the ADC, for example.

In other circumstances, as illustrated in FIG. 43, the power assembly 2096 may comprise a current monitoring mechanism for monitoring current transmitted to the interchangeable working assembly 2094 to detect the one or more signals generated by the working assembly controller 2102, for example. In certain instances, the power assembly 2096 may comprise a current sensor 2110 which can be utilized to monitor current transmitted to the interchangeable working assembly 2094. The monitored current can be reported to the power assembly controller 2100 through an ADC, for example. In other circumstances, the power assembly controller 2100 may be configured to simultaneously monitor both of the current transmitted to the interchangeable working assembly 2094 and the corresponding voltage across the battery 2098 to detect the one or more signals generated by the working assembly controller 2102. The reader will appreciate that various other mechanisms for monitoring current and/or voltage can be utilized by the power assembly controller 2100 to detect the one or more signals generated by the working assembly controller 2102; all such mechanisms are contemplated by the present disclosure.

Figure 44:
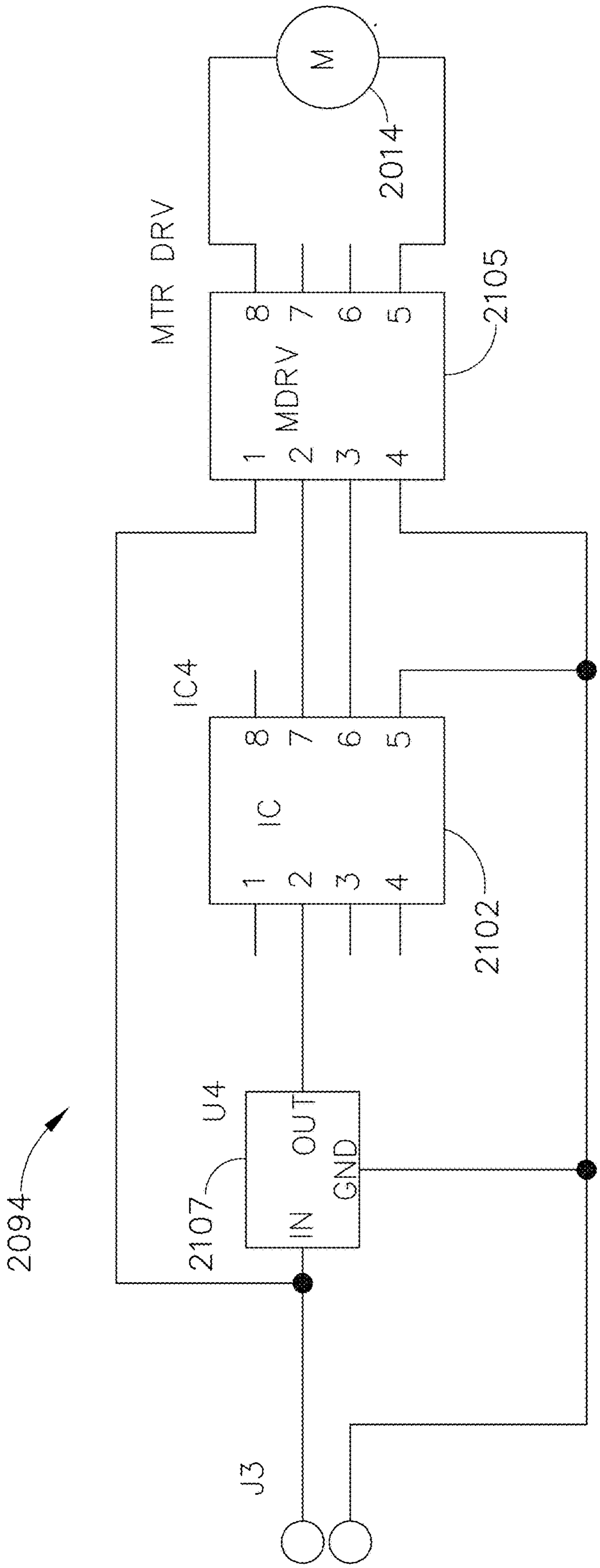
FIG. 44 is a circuit diagram of an exemplary interchangeable working assembly of the surgical instrument of FIG. 41.

As illustrated in FIG. 44, the working assembly controller 2102 can be configured to generate the one or more signals for communication with the power assembly controller 2100 by effectuating the motor driver 2015 to modulate the power transmitted to the motor 2014 from the battery 2098. In result, the voltage across the battery 2098 and/or the current drawn from the battery 2098 to power the motor 2014 may form discrete patterns or waveforms that represent the one or more signals. As described above, the power assembly controller 2100 can be configured to monitor the voltage across the battery 2098 and/or the current drawn from the battery 2098 for the one or more signals generated by the working assembly controller 2102.

Upon detecting a signal, the power assembly controller 2100 can be configured to perform one or more functions that correspond to the detected signal. In at least one example, upon detecting a first signal, the power assembly controller 2100 can be configured to actuate the power modulator control 2106 to set the power output of the battery 2098 to a first duty cycle. In at least one example, upon detecting a second signal, the power assembly controller 2100 can be configured to actuate the power modulator control 2106 to set the power output of the battery 2098 to a second duty cycle different from the first duty cycle.

Figure 45:
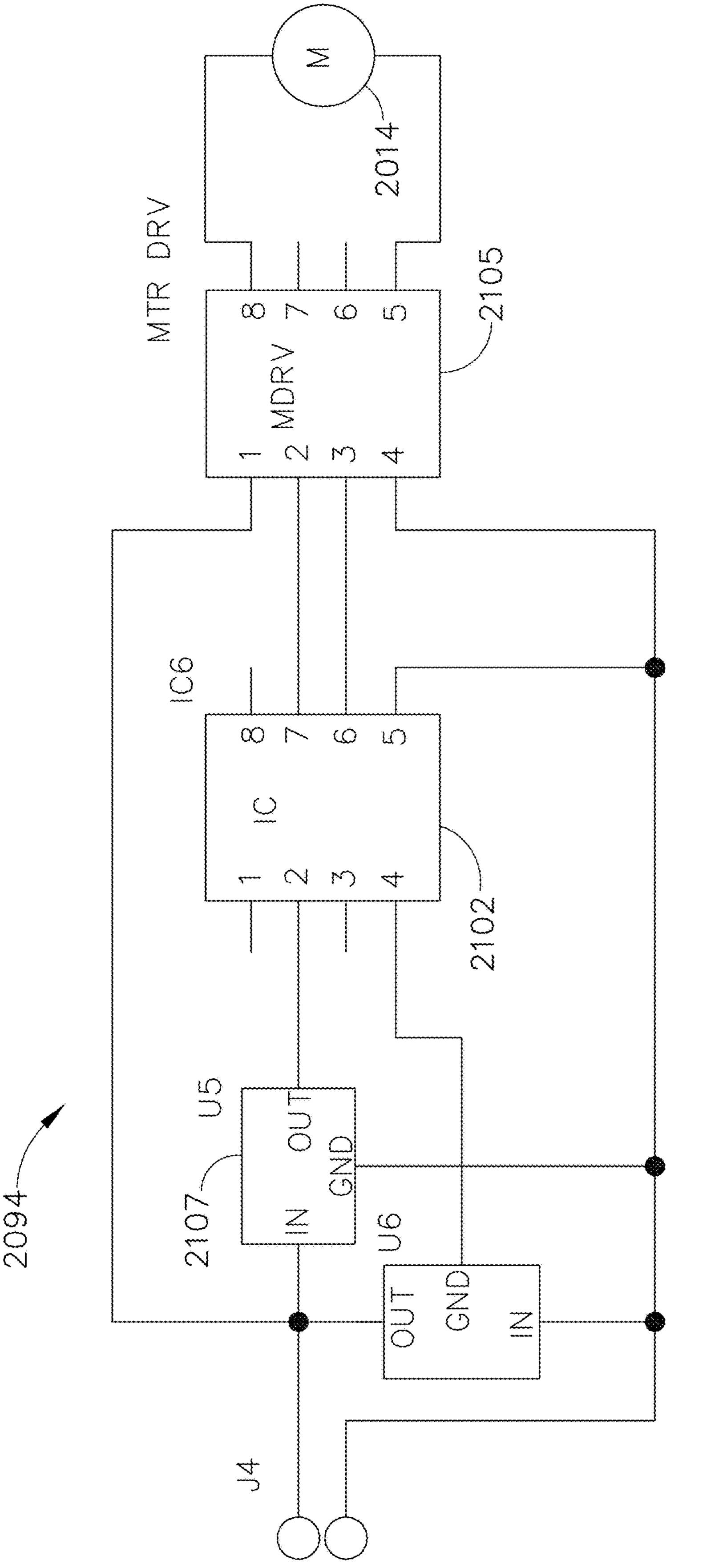
FIG. 45 is a circuit diagram of an exemplary interchangeable working assembly of the surgical instrument of FIG. 41.

In certain circumstances, as illustrated in FIG. 45, the interchangeable working assembly 2094 may include a power modulation circuit 2012 which may comprise one or more field-effect transistors (FETs) which can be controlled by the working assembly controller 2102 to generate a signal or a waveform recognizable by the power assembly controller 2100. For example, in certain circumstances, the working assembly controller 2102 may operate the power modulation circuit 2012 to amplify the voltage higher than the voltage of the battery 2098 to trigger a new power mode of the power assembly 2096, for example.

Referring now primarily to FIGS. 42 and 43, the power assembly 2096 may comprise a switch 2104 which can be switchable between an open position and a closed position. The switch 2104 can be transitioned from the open position to the closed positioned when the power assembly 2096 is coupled with the interchangeable working assembly 2094, for example. In certain instances, the switch 2104 can be manually transitioned from the open position to the closed position after the power assembly 2096 is coupled with the interchangeable working assembly 2094, for example. While the switch 2104 is in the open position, components of the power assembly 2096 may draw sufficiently low or no power to retain capacity of the battery 2098 for clinical use. The switch 2104 can be a mechanical, reed, hall, or any other suitable switching mechanism. Furthermore, in certain circumstances, the power assembly 2096 may include an optional power supply 2105 which may be configured to provide sufficient power to various components of the power assembly 2096 during use of the battery 2098. Similarly, the interchangeable working assembly 2094 also may include an optional power supply 2107 which can be configured to provide sufficient power to various components of the interchangeable working assembly 2094.

Figure 46:
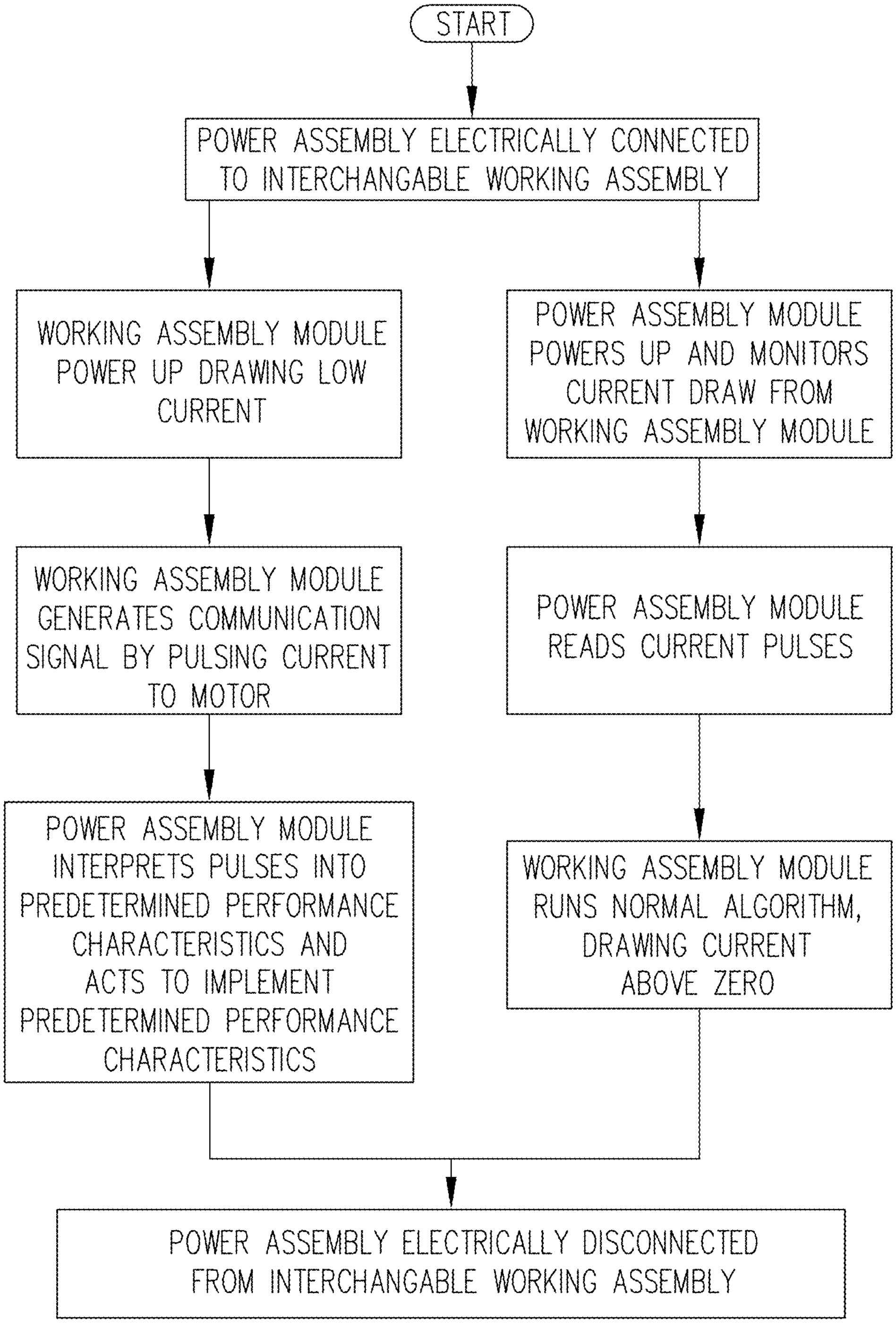
FIG. 46 is a block diagram depicting an exemplary module of the surgical instrument of FIG. 41.

In use, as illustrated in FIG. 46, the power assembly 2096 can be coupled to the interchangeable working assembly 2094. In certain instances, as described above, the switch 2104 can be transitioned to the closed configuration to electrically connect the interchangeable working assembly 2094 to the power assembly 2096. In response, the interchangeable working assembly 2094 may power up and may, at least initially, draw relatively low current from the battery 2098. For example, the interchangeable working assembly 2094 may draw less than or equal to 1 ampere to power various components of the interchangeable working assembly 2094. In certain instances, the power assembly 2096 also may power up as the switch 2014 is transitioned to the closed position. In response, the power assembly controller 2100 may begin to monitor current draw from the interchangeable working assembly 2094, as described in greater detail above, by monitoring voltage across the battery 2098 and/or current transmission from the battery 2098 to the interchangeable working assembly 2094, for example.

Figure 47A:
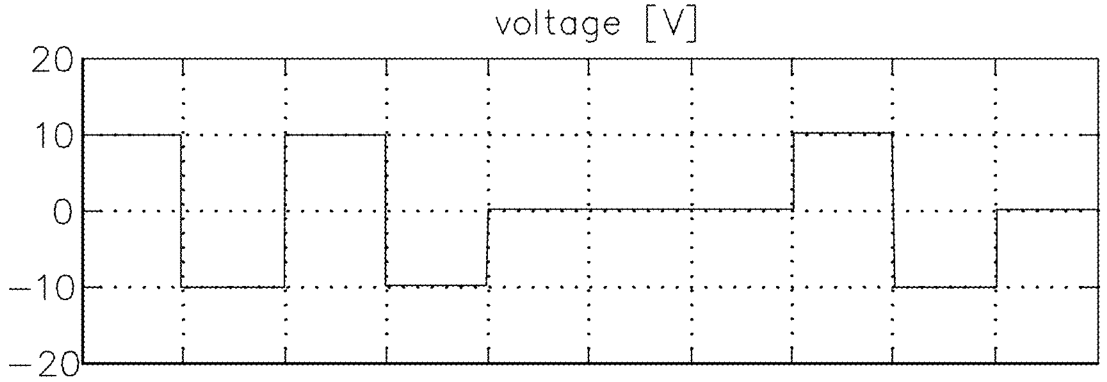
FIG. 47A is a graphical representation of an exemplary communication signal generated by a working assembly controller of the interchangeable working assembly of the surgical instrument of FIG. 41 as detected by a voltage monitoring mechanism.
Figure 47B:
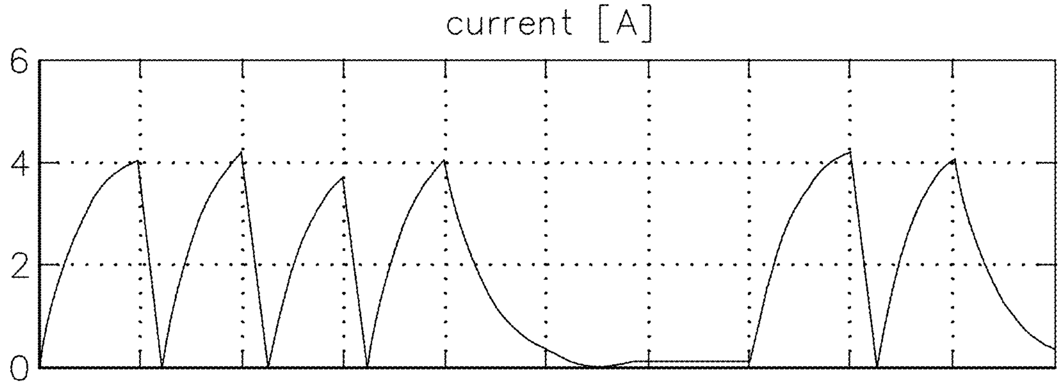
FIG. 47B is a graphical representation of an exemplary communication signal generated by a working assembly controller of the interchangeable working assembly of the surgical instrument of FIG. 41 as detected by a current monitoring mechanism.
Figure 47C:
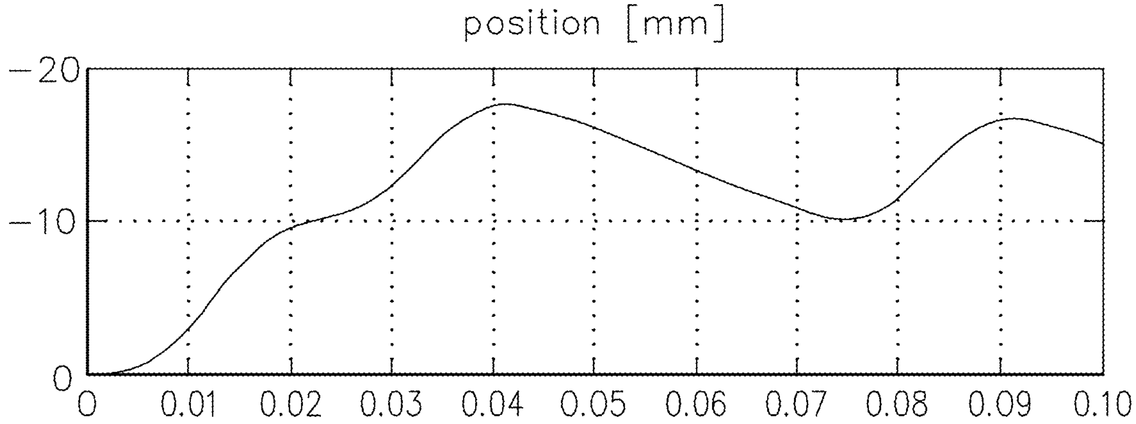
FIG. 47C is a graphical representation of effective motor displacement of a motor of the interchangeable working assembly of FIG. 41 in response to the communication signal generated by the working assembly controller of FIG. 47A.

To generate and transmit a communication signal to the power assembly controller 2100 via power modulation, the working assembly controller 2102 may employ the motor drive 2015 to pulse power to the motor 2014 in patterns or waveforms of power spikes, for example. In certain circumstances, the working assembly controller 2102 can be configured to communicate with the motor driver 2015 to rapidly switch the direction of motion of the motor 2014 by rapidly switching the voltage polarity across the windings of the motor 2014 to limit the effective current transmission to the motor 2014 resulting from the power spikes. In result, as illustrated in FIG. 47C, the effective motor displacement resulting from the power spikes can be reduced to minimize effective displacement of a drive system of the surgical instrument 2090 that is coupled to the motor 2014 in response to the power spikes.

Further to the above, the working assembly controller 2102 may communicate with the power assembly controller 2100 by employing the motor driver 2015 to draw power from the battery 2098 in spikes arranged in predetermined packets or groups which can be repeated over predetermined time periods to form patterns detectable by the power assembly controller 2100. For example, as illustrated in FIGS. 47A and 47B, the power assembly controller 2100 can be configured to monitor voltage across the battery 2100 for predetermined voltage patterns such as, for example, the voltage pattern 2103 (FIG. 47A) and/or predetermined current patterns such as, for example, the current pattern 2109 (FIG. 47B) using voltage and/or current monitoring mechanisms as described in greater detail above. Furthermore, the power assembly controller 2100 can be configured to perform one or more functions upon detecting of a pattern. The reader will appreciate that the communication between the power assembly controller 2100 and the working assembly controller 2102 via power transmission modulation may reduce the number of connection lines needed between the interchangeable working assembly 2094 and the power assembly 2096.

In certain circumstances, the power assembly 2096 can be employed with various interchangeable working assemblies of multiple generations which may comprise different power requirements. Some of the various interchangeable workings assemblies may comprise communication systems, as described above, while others may lack such communication systems. For example, the power assembly 2096 can be utilized with a first generation interchangeable working assembly which lacks the communication system described above. Alternatively, the power assembly 2096 can be utilized with a second generation interchangeable working assembly such as, for example, the interchangeable working assembly 2094 which comprises a communication system, as described above.

Further to the above, the first generation interchangeable working assembly may comprise a first power requirement and the second generation interchangeable working assembly may comprise a second power requirement which can be different from the first power requirement. For example, the first power requirement may be less than the second power requirement. To accommodate the first power requirement of the first generation interchangeable working assembly and the second power requirement of the second generation interchangeable working assembly, the power assembly 2096 may comprise a first power mode for use with the first generation interchangeable working assembly and a second power mode for use with the second generation interchangeable working assembly. In certain instances, the power assembly 2096 can be configured to operate at a default first power mode corresponding to the power requirement of the first generation interchangeable working assembly. As such, when a first generation interchangeable working assembly is connected to the power assembly 2096, the default first power mode of the power assembly 2096 may accommodate the first power requirement of the first generation interchangeable working assembly.

However, when a second generation interchangeable working assembly such as, for example, the interchangeable working assembly 2094 is connected to the power assembly 2096, the working assembly controller 2102 of the interchangeable working assembly 2094 may communicate, as described above, with the power assembly controller 2100 of the power assembly 2096 to switch the power assembly 2096 to the second power mode to accommodate the second power requirement of the interchangeable working assembly 2094. The reader will appreciate that since the first generation interchangeable working assembly lacks the ability to generate a communication signal, the power assembly 2096 will remain in the default first power mode while connected to the first generation interchangeable working assembly.

As described above, the battery 2098 can be rechargeable. In certain circumstances, it may be desirable to drain the battery 2098 prior to shipping the power assembly 2096. A dedicated drainage circuit can be activated to drain the battery 2098 in preparation for shipping of the power assembly 2096. Upon reaching its final destination, the battery 2098 can be recharged for use during a surgical procedure. However, the drainage circuit may continue to consume energy from the battery 2098 during clinical use. In certain circumstances, the interchangeable working assembly controller 2102 can be configured to transmit a drainage circuit deactivation signal to the power assembly controller 2100 by modulating power transmission from the battery 2098 to the motor 2014, as described in greater detail above. The power assembly controller 2100 can be programmed to deactivate the drainage circuit to prevent drainage of the battery 2098 by the drainage circuit in response to the drainage circuit deactivation signal, for example. The reader will appreciate that various communication signals can be generated by the working assembly controller 2102 to instruct the power assembly controller 2100 to perform various functions while the power assembly 2096 is coupled to the interchangeable working assembly 2094.

Referring again to FIGS. 42-45, the power assembly controller 2100 and/or the working assembly controller 2102 may comprise one or more processors and/or memory units which may store a number of software modules. Although certain modules and/or blocks of the surgical instrument 2050 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

Figure 48:
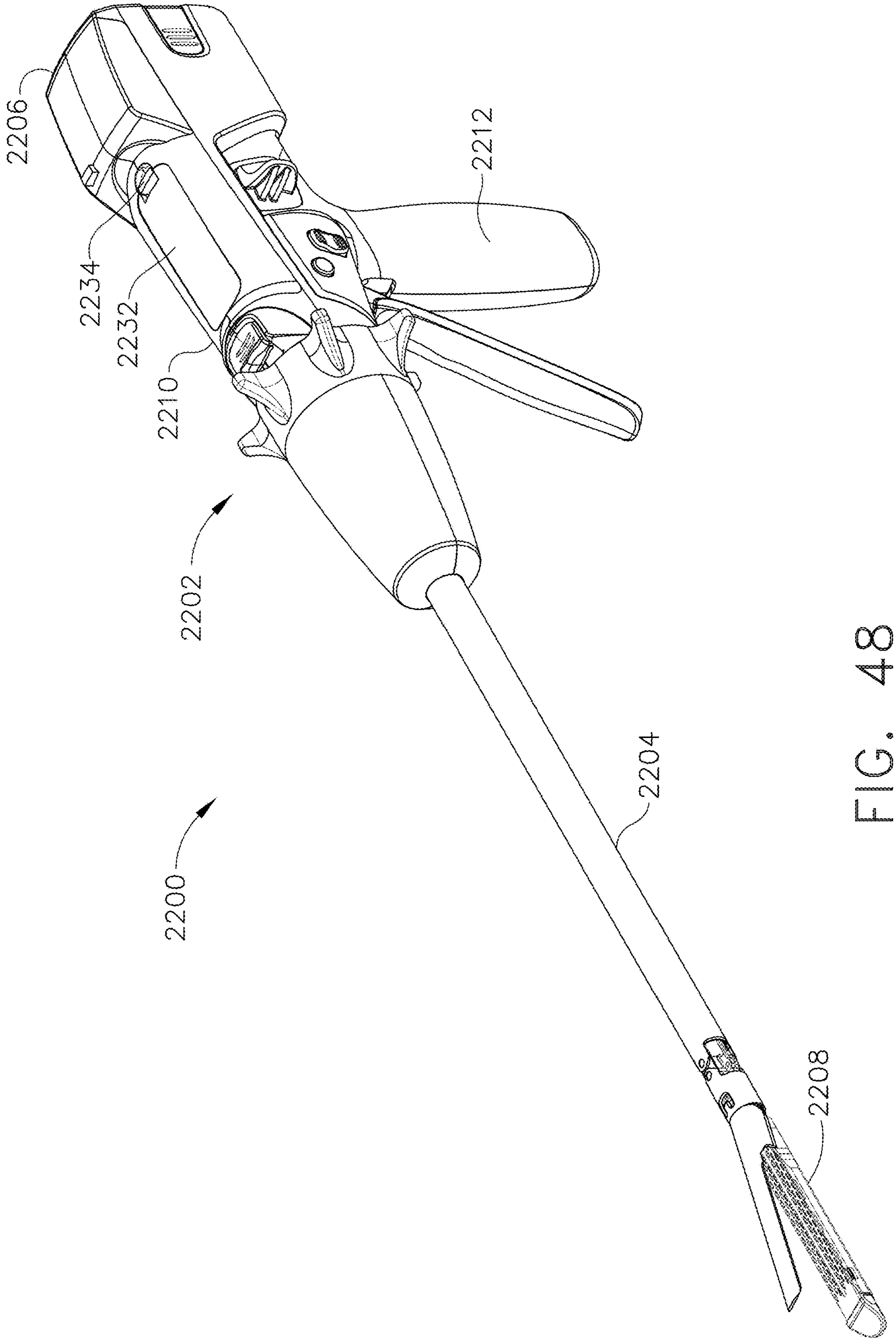
FIG. 48 is a perspective view of a surgical instrument comprising a handle assembly and a shaft assembly including an end effector.
Figure 49:
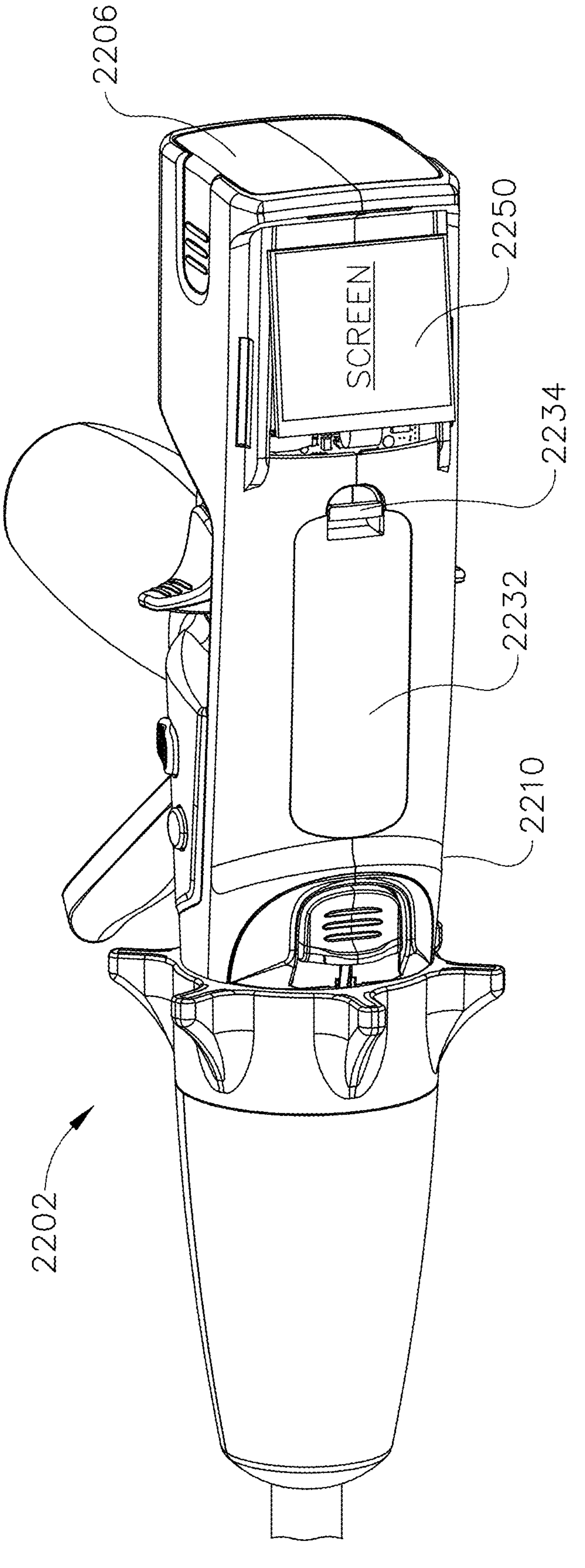
FIG. 49 is a perspective view of the handle assembly of the surgical instrument of FIG. 48.

FIG. 48 generally depicts a motor-driven surgical instrument 2200. In certain circumstances, the surgical instrument 2200 may include a handle assembly 2202, a shaft assembly 2204, and a power assembly 2206 (or "power source" or "power pack"). The shaft assembly 2204 may include an end effector 2208 which, in certain circumstances, can be configured to act as an endocutter for clamping, severing, and/or stapling tissue, although, in other circumstances, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, the entire disclosures of which are incorporated herein by reference in their entirety.

In certain circumstances, the handle assembly 2202 can be separably couplable to the shaft assembly 2204, for example. In such circumstances, the handle assembly 2202 can be employed with a plurality of interchangeable shaft assemblies which may comprise surgical end effectors such as, for example, the end effector 2208 that can be configured to perform one or more surgical tasks or procedures. For example, one or more of the interchangeable shaft assemblies may employ end effectors that are adapted to support different sizes and types of staple cartridges, have different shaft lengths, sizes, and types, etc. Examples of suitable interchangeable shaft assemblies are disclosed in U.S. Provisional Patent Application Ser. No. 61/782,866, entitled CONTROL SYSTEM OF A SURGICAL INSTRUMENT, and filed Mar. 14, 2013, the entire disclosure of which is hereby incorporated by reference herein in its entirety.

Referring still to FIG. 48, the handle assembly 2202 may comprise a housing 2210 that consists of a handle 2212 that may be configured to be grasped, manipulated, and/or actuated by a clinician. However, it will be understood that the various unique and novel arrangements of the housing 2210 also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the shaft assembly 2204 disclosed herein and its respective equivalents. For example, the housing 2210 disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is incorporated by reference herein in its entirety.

Figure 50:
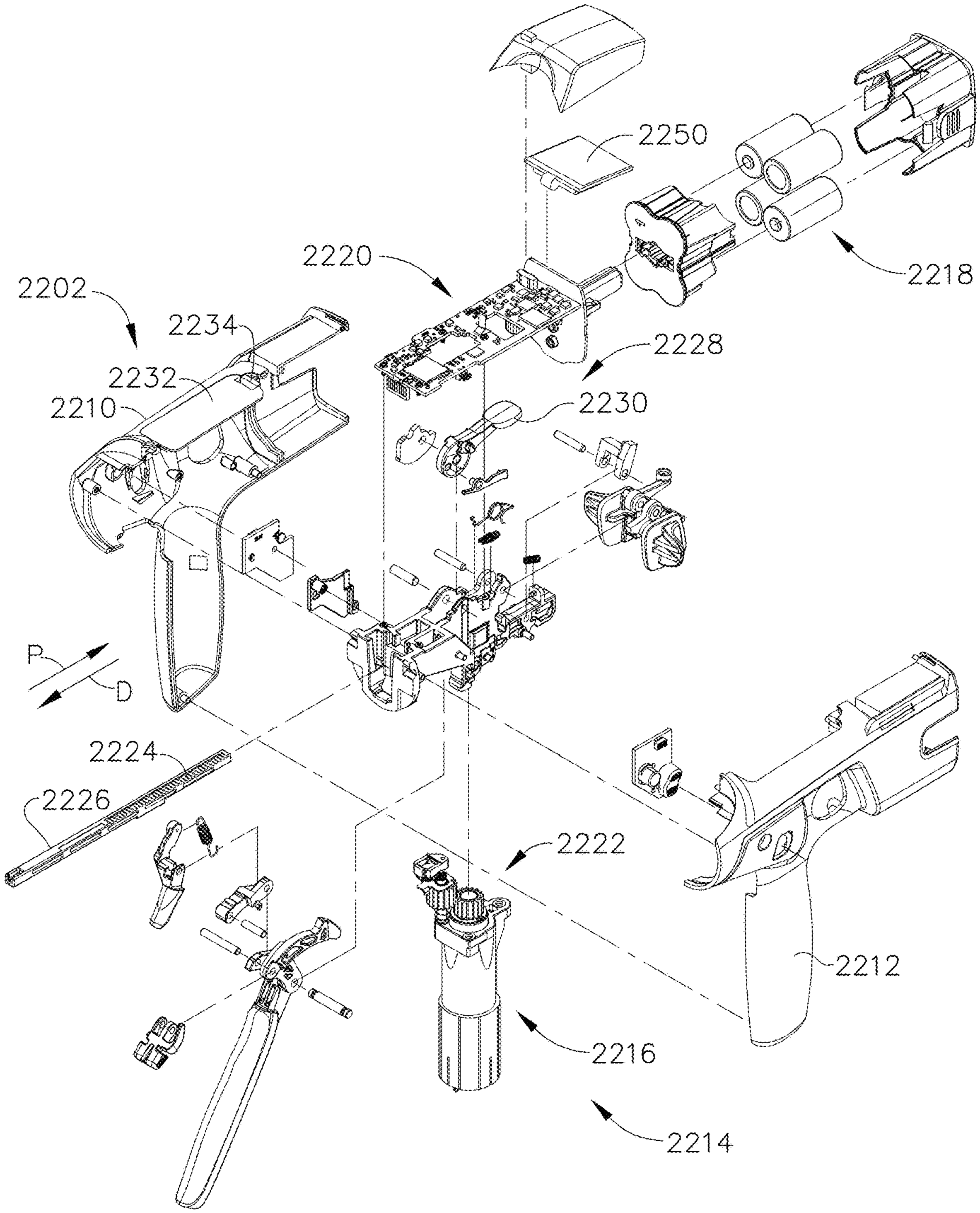
FIG. 50 is an exploded view of the handle assembly of the surgical instrument of FIG. 48.

In at least one form, the surgical instrument 2200 may be a surgical fastening and cutting instrument. Furthermore, the housing 2210 may operably support one or more drive systems. For example, as illustrated in FIG. 50, the housing 2210 may support a drive system referred to herein as firing drive system 2214 that is configured to apply firing motions to the end effector 2208. The firing drive system 2214 may employ an electric motor 2216, which can be located in the handle 2212, for example. In various forms, the motor 2216 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. A battery 2218 (or "power source" or "power pack"), such as a Li ion battery, for example, may be coupled to the handle 2212 to supply power to a control circuit board assembly 2220 and ultimately to the motor 2216.

In certain circumstances, referring still to FIG. 50, the electric motor 2216 can include a rotatable shaft (not shown) that may operably interface with a gear reducer assembly 2222 that may be mounted in meshing engagement with a with a set, or rack, of drive teeth 2224 on a longitudinally-movable drive member 2226. In use, a voltage polarity provided by the battery 2218 can operate the electric motor 2216 in a clockwise direction wherein the voltage polarity applied to the electric motor by the battery 2218 can be reversed in order to operate the electric motor 2216 in a counter-clockwise direction. When the electric motor 2216 is rotated in one direction, the drive member 2226 will be axially driven in a distal direction "D", for example, and when the motor 2216 is driven in the opposite rotary direction, the drive member 2226 will be axially driven in a proximal direction "P", for example, as illustrated in FIG. 50. The handle 2212 can include a switch which can be configured to reverse the polarity applied to the electric motor 2216 by the battery 2218. As with the other forms described herein, the handle 2212 also can include a sensor that is configured to detect the position of the drive member 2226 and/or the direction in which the drive member 2226 is being moved.

As indicated above, in at least one form, the longitudinally movable drive member 2226 may include a rack of drive teeth 2224 formed thereon for meshing engagement with the gear reducer assembly 2222. In certain circumstances, as illustrated in FIG. 50, the surgical instrument 2200 may include a manually-actuatable "bailout" assembly 2228 that can be configured to enable a clinician to manually retract the longitudinally movable drive member 2226 when a bailout error is detected such as, for example, when the motor 2216 malfunctions during operation of the surgical instrument 2200 which may cause tissue captured by the end effector 2208 to be trapped.

Further to the above, as illustrated in FIG. 50, the bailout assembly 2228 may include a lever or bailout handle 2230 configured to be manually moved or pivoted into ratcheting engagement with the teeth 2224 in the drive member 2226. In such circumstances, the clinician can manually retract the drive member 2226 by using the bailout handle 2230 to ratchet the drive member 2226 in the proximal direction "P", for example, to release the trapped tissue from the end effector 2208, for example. Exemplary bailout arrangements and other components, arrangements and systems that may be employed with the various instruments disclosed herein are disclosed in U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, which is hereby incorporated by reference herein in its entirety.

Further to the above, referring now primarily to FIGS. 48 and 50, the bailout handle 2230 of the bailout assembly 2228 may reside within the housing 2210 of the handle assembly 2202. In certain circumstances, access to the bailout handle 2230 can be controlled by a bailout door 2232. The bailout door 2232 can be releasably locked to the housing 2210 to control access to the bailout handle 2230. As illustrated in FIG. 48, the bailout door 2232 may include a locking mechanism such as, for example, a snap-type locking mechanism 2234 for locking engagement with the housing 2210. Other locking mechanisms for locking the bailout door 2232 to the housing 2210 are contemplated by the present disclosure. In use, a clinician may obtain access to the bailout handle 2230 by unlocking the locking mechanism 2234 and opening the bailout door 2232. In at least one example, the bailout door 2232 can be separably coupled to the housing 2232 and can be detached from the housing 2210 to provide access to the bailout handle 2230, for example. In another example, the bailout door 2232 can be pivotally coupled to the housing 2210 via hinges (not shown) and can be pivoted relative to the housing 2210 to provide access to the bailout handle 2230, for example. In yet another example, the bailout door 2232 can be a sliding door which can be slidably movable relative to the housing 2210 to provide access to the bailout handle 2230.

Figure 51:
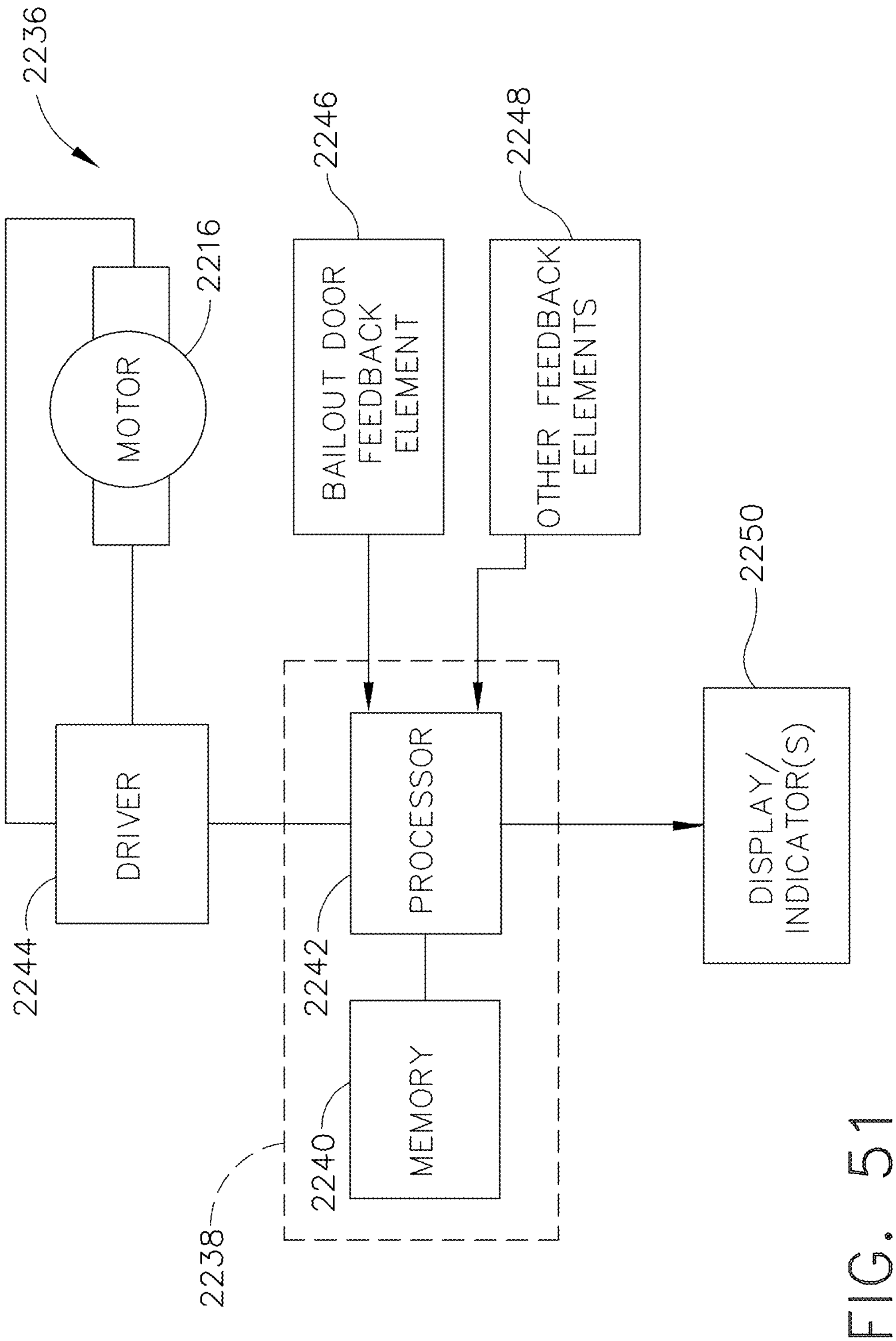
FIG. 51 is a schematic diagram of a bailout feedback system of the surgical instrument of FIG. 48.

Referring now to FIG. 51, the surgical instrument 2200 may include a bailout feedback system 2236 which can be configured to guide and/or provide feedback to a clinician through the various steps of utilizing the bailout assembly 2228, as described below in greater detail. In certain instances, the bailout feedback system 2236 may include a microcontroller 2238 and/or one or more bailout feedback elements. The electrical and electronic circuit elements associated with the bailout feedback system 2236 and/or the bailout feedback elements may be supported by the control circuit board assembly 2220, for example. The microcontroller 2238 may generally comprise a memory 2240 and a microprocessor 2242 ("processor") operationally coupled to the memory 2240. The processor 2242 may control a motor driver 2244 circuit generally utilized to control the position and velocity of the motor 2216. In certain instances, the processor 2242 can signal the motor driver 2244 to stop and/or disable the motor 2216, as described in greater detail below. In certain instances, the processor 2242 may control a separate motor override circuit which may comprise a motor override switch that can stop and/or disable the motor 2216 during operation of the surgical instrument 2200 in response to an override signal from the processor 2242. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 2242 may be any single core or multicore processor such as those known under the trade name ARM Cortex by Texas Instruments. In one instance, the surgical instrument 2200 may comprise a safety processor such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 1004 may be configured specifically for IEC 61508 and ISO 26262 safety critical applications, among others, to provide advanced integrated safety features while delivering scalable performance, connectivity, and memory options.

In certain instances, the microcontroller 2238 may be an LM 4F230H5QR, available from Texas Instruments, for example. In at least one example, the Texas Instruments LM4F230H5QR is an ARM Cortex-M4F Processor Core comprising on-chip memory 2240 of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other microcontrollers may be readily substituted for use in the bailout feedback system 2236. Accordingly, the present disclosure should not be limited in this context.

Referring again to FIG. 51, the bailout feedback system 2236 may include a bailout door feedback element 2246, for example. In certain instances, the bailout door feedback element 2246 can be configured to alert the processor 2242 that the locking mechanism 2234 is unlocked. In at least one example, the bailout door feedback element 2246 may comprise a switch circuit (not shown) operably coupled to the processor 2242; the switch circuit can be configured to be transitioned to an open configuration when the locking mechanism 2234 is unlocked by a clinician and/or transitioned to a closed configuration when the locking mechanism 2234 is locked by the clinician, for example. In at least one example, the bailout door feedback element 2246 may comprise at least one sensor (not shown) operably coupled to the processor 2242; the sensor can be configured to be triggered when the locking mechanism 2234 is transitioned to unlocked and/or locked configurations by the clinician, for example. The reader will appreciate that the bailout door feedback element 2246 may include other means for detecting the locking and/or unlocking of the locking mechanism 2234 by the clinician.

In certain instances, the bailout door feedback element 2246 may comprise a switch circuit (not shown) operably coupled to the processor 2242; the switch circuit can be configured to be transitioned to an open configuration when the bailout door 2232 is removed or opened, for example, and/or transitioned to a closed configuration when the bailout door 2232 is installed or closed, for example. In at least one example, the bailout door feedback element 2246 may comprise at least one sensor (not shown) operably coupled to the processor 2242; the sensor can be configured to be triggered when the bailout door 2232 is removed or opened, for example, and/or when the bailout door 2232 is closed or installed, for example. The reader will appreciate that the bailout door feedback element 2246 may include other means for detecting the locking and/or unlocking of the locking mechanism 2234 and/or the opening and/or closing of the bailout door 2232 by the clinician.

In certain instances, as illustrated in FIG. 51, the bailout feedback system 2236 may comprise one or more additional feedback elements 2248 which may comprise additional switch circuits and/or sensors in operable communication with the processor 2242; the additional switch circuits and/or sensors may be employed by the processor 2242 to measure other parameters associated with the bailout feedback system 2236. In certain instances, the bailout feedback system 2236 may comprise one or more interfaces which may include one or more devices for providing a sensory feedback to a user. Such devices may comprise, for example, visual feedback devices such as display screens and/or LED indicators, for example. In certain instances, such devices may comprise audio feedback devices such as speakers and/or buzzers, for example. In certain instances, such devices may comprise tactile feedback devices such as haptic actuators, for example. In certain instances, such devices may comprise combinations of visual feedback devices, audio feedback devices, and/or tactile feedback devices. In certain circumstances, as illustrated in FIG. 48, the one or more interfaces may comprise a display 2250 which may be included in the handle assembly 2202, for example. In certain instances, the processor 2242 may employ the display 2250 to alert, guide, and/or provide feedback to a user of the surgical instrument 2200 with regard to performing a manual bailout of the surgical instrument 2200 using the bailout assembly 2228.

Figure 52:
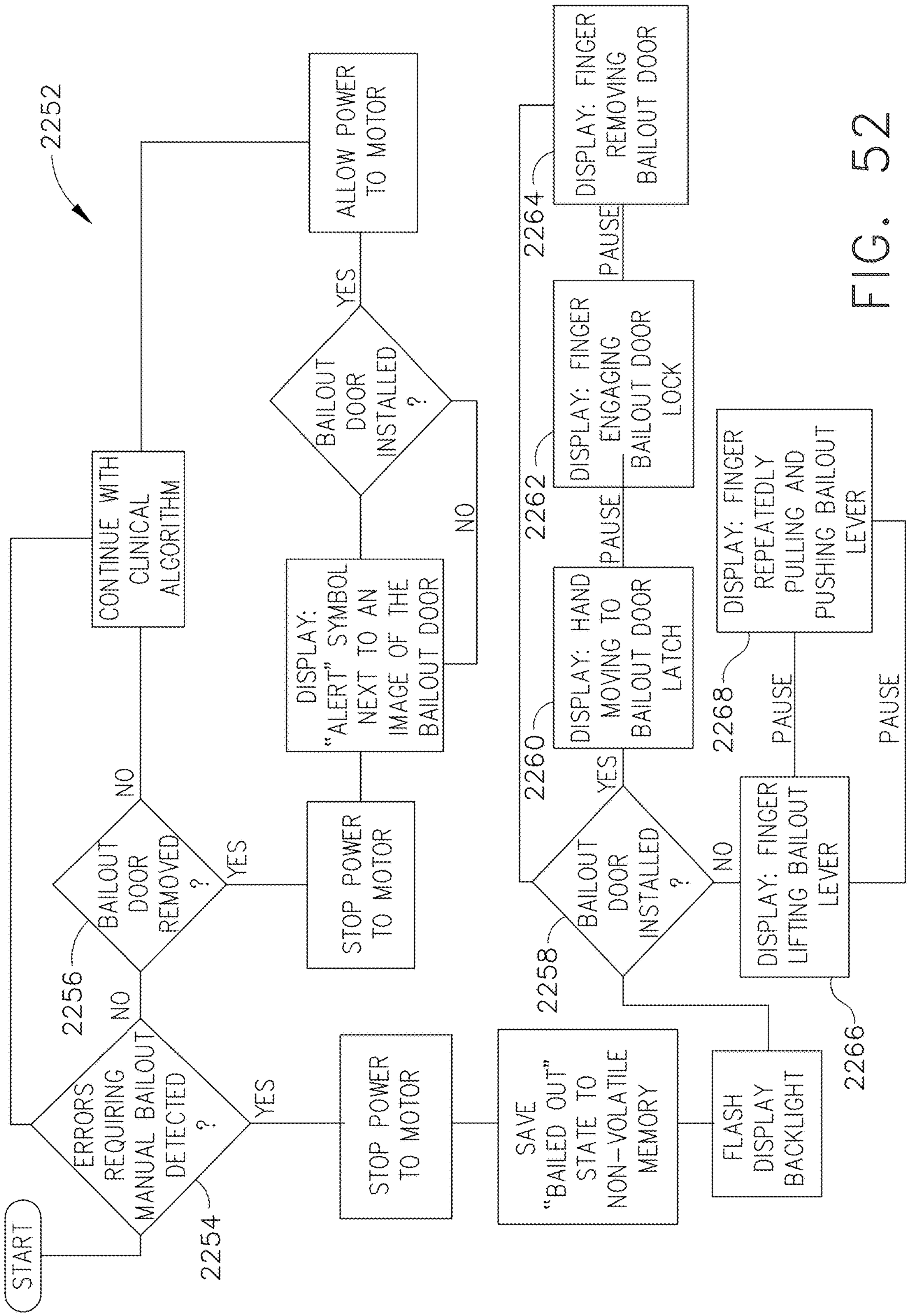
FIG. 52 is a block diagram of a module for use with the bailout feedback system of FIG. 51.

In certain instances, the bailout feedback system 2236 may comprise one or more embedded applications implemented as firmware, software, hardware, or any combination thereof. In certain instances, the bailout feedback system 2236 may comprise various executable modules such as software, programs, data, drivers, and/or application program interfaces (APIs), for example. FIG. 52 depicts an exemplary module 2252 that can be stored in the memory 2240, for example. The module 2252 can be executed by the processor 2242, for example, to alert, guide, and/or provide feedback to a user of the surgical instrument 2200 with regard to performing a manual bailout of the surgical instrument 2200 using the bailout assembly 2228.

As illustrated in FIG. 52, the module 2252 may be executed by the processor 2242 to provide the user with instructions as to how to access and/or use the bailout assembly 2228 to perform the manual bailout of the surgical instrument 2200, for example. In various instances, the module 2252 may comprise one or more decision-making steps such as, for example, a decision-making step 2254 with regard to the detection of one or more errors requiring the manual bailout of the surgical instrument 2200.

In various instances, the processor 2242 may be configured to detect a bailout error in response to the occurrence of one or more intervening events during the normal operation of the surgical instrument 2200, for example. In certain instances, the processor 2242 may be configured to detect a bailout error when one or more bailout error signals are received by the processor 2242; the bailout error signals can be communicated to the processor 2242 by other processors and/or sensors of the surgical instrument 2200, for example. In certain instances, a bailout error can be detected by the processor 2242 when a temperature of the surgical instrument 2200, as detected by a sensor (not shown), exceeds a threshold, for example. In certain instances, the surgical instrument 2200 may comprise a positioning system (not shown) for sensing and recording the position of the longitudinally-movable drive member 2226 during a firing stroke of the firing drive system 2214. In at least one example, the processor 2242 can be configured to detect a bailout error when one or more of the recorded positions of the longitudinally-movable drive member 2226 is not are accordance with a predetermined threshold, for example.

In any event, referring again to FIG. 52, when the processor 2242 detects a bailout error in the decision-making step 2254, the processor 2242 may respond by stopping and/or disabling the motor 2216, for example. In addition, in certain instances, the processor 2242 also may store a bailed out state in the memory 2240 after detecting the bailout error, as illustrated in FIG. 52. In other words, the processor 2242 may store in the memory 2240*a* status indicating that a bailout error has been detected. As described above, the memory 2240 can be a non-volatile memory which may preserve the stored status that a bailout error has been detected when the surgical instrument 2200 is reset by the user, for example.

In various instances, the motor 2216 can be stopped and/or disabled by disconnecting the battery 2218 from the motor 2216, for example. In various instances, the processor 2242 may employ the driver 2244 to stop and/or disable the motor 2216. In certain instances, when the motor override circuit is utilized, the processor 2242 may employ the motor override circuit to stop and/or disable the motor 2216. In certain instances, stopping and/or disabling the motor 2216 may prevent a user of the surgical instrument 2200 from using the motor 2216 at least until the manual bailout is performed, for example. The reader will appreciate that stopping and/or disabling the motor 2216 in response to the detection of a bailout error can be advantageous in protecting tissue captured by the surgical instrument 2200.

Further to the above, referring still to FIG. 52, the module 2252 may include a decision-making step 2256 for detecting whether the bailout door 2232 is removed. As described above, the processor 2242 can be operationally coupled to the bailout door feedback element 2246 which can be configured to alert the processor 2242 as to whether the bailout door 2232 is removed. In certain instances, the processor 2242 can be programmed to detect that the bailout door 2232 is removed when the bailout door feedback element 2246 reports that the locking mechanism 2234 is unlocked, for example. In certain instances, the processor 2242 can be programmed to detect that the bailout door 2232 is removed when the bailout door feedback element 2246 reports that the bailout door 2232 is opened, for example. In certain instances, the processor 2242 can be programmed to detect that the bailout door 2232 is removed when the bailout door feedback element 2246 reports that the locking mechanism 2234 is unlocked and that the bailout door 2232 is opened, for example.

In various instances, referring still to FIG. 52, when the processor 2242 does not detect a bailout error in the decision-making step 2254 and does not detect that the bailout door 2232 is removed in the decision-making step 2256, the processor 2242 may not interrupt the normal operation of the surgical instrument 2200 and may proceed with various clinical algorithms. In certain instances, when the processor 2242 does not detect a bailout error in the decision-making step 2254 but detects that the bailout door 2232 is removed in the decision-making step 2256, the processor 2242 may respond by stopping and/or disabling the motor 2216, as described above. In addition, in certain instances, the processor 2242 also may provide the user with instructions to reinstall the bailout door 2232, as described in greater detail below. In certain instances, when the processor 2242 detects that the bailout door 2232 is reinstalled, while no bailout error is detected, the processor 2242 can be configured to reconnect the power to the motor 2216 and allow the user to continue with clinical algorithms, as illustrated in FIG. 52.

In certain instances, when the user does not reinstall the bailout door 2232, the processor 2242 may not reconnect power to the motor 2216 and may continue providing the user with the instructions to reinstall the bailout door 2232. In certain instances, when the user does not reinstall the bailout door 2232, the processor 2242 may provide the user with a warning that the bailout door 2232 needs to be reinstalled in order to continue with the normal operation of the surgical instrument 2200. In certain instances, the surgical instrument 2200 can be equipped with an override mechanism (not shown) to permit the user to reconnect power to the motor 2216 even when the bailout door 2216 is not installed.

In various instances, the processor 2242 can be configured to provide the user with a sensory feedback when the processor 2242 detects that the bailout door 2232 is removed. In various instances, the processor 2242 can be configured to provide the user with a sensory feedback when the processor 2242 detects that the bailout door 2232 is reinstalled. Various devices can be employed by the processor 2242 to provide the sensory feedback to the user. Such devices may comprise, for example, visual feedback devices such as display screens and/or LED indicators, for example.

In certain instances, such devices may comprise audio feedback devices such as speakers and/or buzzers, for example. In certain instances, such devices may comprise tactile feedback devices such as haptic actuators, for example. In certain instances, such devices may comprise combinations of visual feedback devices, audio feedback devices, and/or tactile feedback devices. In certain instances, the processor 2242 may employ the display 2250 to instruct the user to reinstall the bailout door 2232. For example, the processor 2242 may present an alert symbol next to an image of the bailout door 2232 to the user through the display 2250, for example. In certain instances, the processor 2242 may present an animated image of the bailout door 2232 being installed, for example. Other images, symbols, and/or words can be displayed through the display 2250 to alert the user of the surgical instrument 2200 to reinstall the bailout door 2232.

Referring again to FIG. 52, when a bailout error is detected, the processor 2242 may signal the user of the surgical instrument 2200 to perform the manual bailout using the bailout handle 2230. In various instances, the processor 2242 can signal the user to perform the manual bailout by providing the user with a visual, audio, and/or tactile feedback, for example. In certain instances, as illustrated in FIG. 52, the processor 2242 can signal the user of the surgical instrument 2200 to perform the manual bailout by flashing a backlight of the display 2250. In any event, the processor 2242 may then provide the user with instructions to perform the manual bailout. In various instances, as illustrated in FIG. 52, the instructions may depend on whether the bailout door 2232 is installed; a decision making step 2258 may determine the type of instructions provided to the user. In certain instances, when the processor 2242 detects that the bailout door 2232 is installed, the processor 2242 may provide the user with instructions to remove the bailout door 2232 and instructions to operate the bailout handle 2230, for example. However, when the processor 2242 detects that the bailout door 2232 is removed, the processor 2242 may provide the user with the instructions to operate the bailout handle 2230 but not the instructions to remove the bailout door 2232, for example.

Referring again to FIG. 52, in various instances, the instructions provided by the processor 2242 to the user to remove the bailout door 2232 and/or to operate the bailout handle 2230 may comprise one or more steps; the steps may be presented to the user in a chronological order. In certain instances, the steps may comprise actions to be performed by the user. In such instances, the user may proceed through the steps of the manual bailout by performing the actions presented in each of the steps. In certain instances, the actions required in one or more of the steps can be presented to the user in the form of animated images displayed on the display 2250, for example. In certain instances, one or more of the steps can be presented to the user as messages which may include words, symbols, and/or images that guide the user through the manual bailout. In certain instances, one or more of the steps of performing the manual bailout can be combined in one or more messages, for example. In certain instances, each message may comprise a separate step, for example.

In certain instances, the steps and/or the messages providing the instructions for the manual bailout can be presented to the user in predetermined time intervals to allow the user sufficient time to comply with the presented steps and/or messages, for example. In certain instances, the processor 2242 can be programed to continue presenting a step and/or a message until feedback is received by the processor 2242 that the step has been performed. In certain instances, the feedback can be provided to the processor 2242 by the bailout door feedback element 2246, for example. Other mechanisms and/or sensors can be employed by the processor 2242 to obtain feedback that a step has been completed. In at least one example, the user can be instructed to alert that processor 2242 when a step is completed by pressing an alert button, for example. In certain instances, the display 2250 may comprise a capacitive screen which may provide the user with an interface to alert the processor 2242 when a step is completed. For example, the user may press the capacitive screen to move to the next step of the manual bailout instructions after a current step is completed.

In certain instances, as illustrated in FIG. 52, after detecting that the bailout door 2232 is installed, the processor 2242 can be configured to employ the display 2250 to present an animated image 2260 depicting a hand moving toward the bailout door 2232. The processor 2242 may continue to display the animated image 2260 for a time interval sufficient for the user to engage the bailout door 2232, for example. In certain instances, the processor 2242 may then replace the animated image 2260 with an animated image 2262 depicting a finger engaging the bailout door locking mechanism 2234, for example. The processor 2242 may continue to display the animated image 2262 for a time interval sufficient for the user to unlock the locking mechanism 2234, for example. In certain instances, the processor 2242 may continue to display the animated image 2262 until the bailout door feedback element 2246 reports that the locking mechanism 2234 is unlocked, for example. In certain instances, the processor 2242 may continue to display the animated image 2262 until the user alerts the processor 2242 that the step of unlocking the locking mechanism 2234 is completed.

In any event, the processor 2242 may then replace the animated image 2262 with an animated image 2264 depicting a finger removing the bailout door 2232, for example. The processor 2242 may continue to display the animated image 2264 for a time interval sufficient for the user to remove the bailout door 2232, for example. In certain instances, the processor 2242 may continue to display the animated image 2264 until the bailout door feedback element 2246 reports that the bailout door 2232 is removed, for example. In certain instances, the processor 2242 may continue to display the animated image 2264 until the user alerts the processor 2242 that the step of removing the bailout door 2232 has been removed, for example. In certain instances, the processor 2242 can be configured to continue to repeat displaying the animated images 2260, 2262, and 2246 in their respective order when the processor 2242 continues to detect that the bailout door is installed at the decision making step 2258, for example.

Further to the above, after detecting that the bailout door 2232 is removed, the processor 2242 may proceed to guide the user through the steps of operating the bailout handle 2230. In certain instances, the processor 2242 may replace the animated image 2264 with an animated image 2266 depicting a finger lifting the bailout handle 2230, for example, into ratcheting engagement with the teeth 2224 in the drive member 2226, as described above. The processor 2242 may continue to display the animated image 2266 for a time interval sufficient for the user to lift the bailout handle 2230, for example. In certain instances, the processor 2242 may continue to display the animated image 2266 until the processor receives feedback that the bailout handle 2230 has been lifted. For example, the processor 2242 may continue to display the animated image 2266 until the user alerts the processor 2242 that the step of lifting the bailout handle 2230 has been removed.

In certain instances, as described above, the user can manually retract the drive member 2226 by using the bailout handle 2230 to ratchet the drive member 2226 in the proximal direction "P," for example, to release tissue trapped by the end effector 2208, for example. In such instances, the processor 2242 may replace the animated image 2266 with an animated image 2268 depicting a finger repeatedly pulling then pushing the bailout handle 2230, for example, to simulate the ratcheting of the bailout handle 2230. The processor 2242 may continue to display the animated image 2268 for a time interval sufficient for the user to ratchet the drive member 2226 to default position, for example. In certain instances, the processor 2242 may continue to display the animated image 2268 until the processor 2242 receives feedback that the drive member 2226 has been retracted.

Figure 53:
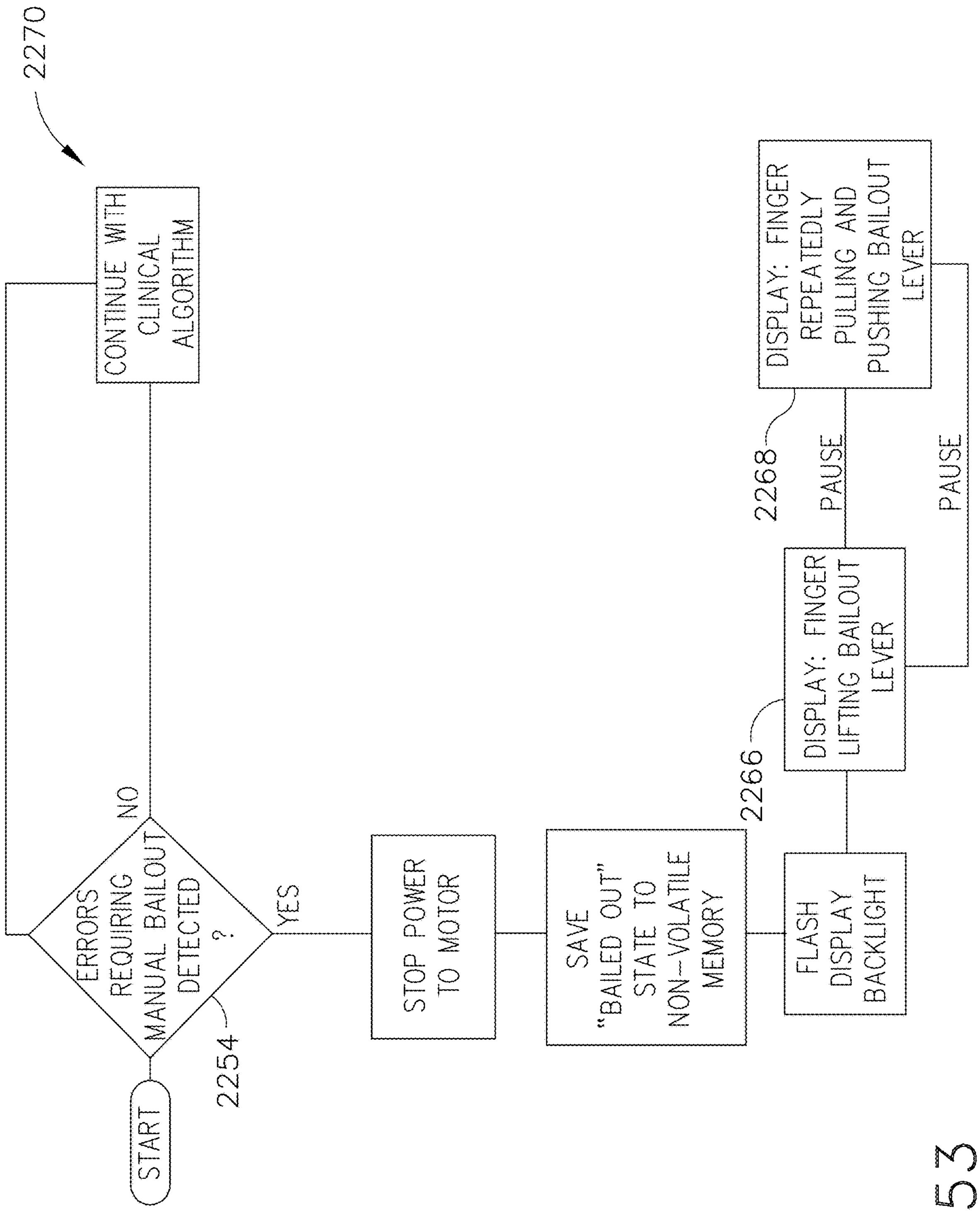
FIG. 53 is a block diagram of a module for use with the bailout feedback system of FIG. 51.

FIG. 53 depicts a module 2270 which is similar in many respects to the module 2258. For example, the module 2252 also can be stored in the memory 2240 and/or executed by the processor 2242, for example, to alert, guide, and/or provide feedback to a user of the surgical instrument 2200 with regard to performing a manual bailout of the surgical instrument 2200. In certain instances, the surgical instrument 2200 may not comprise a bailout door. In such circumstances, the module 2270 can be employed by the processor 2242 to provide the user with instructions as to how to operate the bailout handle 2230, for example.

Referring again to the module 2270 depicted in FIG. 53, when the processor 2242 does not detect a bailout error in the decision-making step 2254 of the module 2270, the processor 2242 may not interrupt the normal operation of the surgical instrument 2200 and may proceed with various clinical algorithms. However, when the processor 2242 detects a bailout error in the decision-making step 2254 of the module 2270, the processor 2242 may respond by stopping and/or disabling the motor 2216, for example. In addition, in certain instances, the processor 2242 also may store a bailed out state in the memory 2240 after detecting the bailout error, as illustrated in FIG. 53. In the absence of a bailout door, the processor 2242 may signal the user of the surgical instrument 2200 to perform the manual bailout, for example, by flashing the backlight of the display 2250; the processor 2242 may then proceed directly to providing the user with the instructions to operate the bailout handle 2230, as described above.

The reader will appreciate that the steps depicted in FIGS. 52 and/or 53 are illustrative examples of the instructions that can be provided to the user of the surgical instrument 2200 to perform a manual bailout. The modules 2252 and/or 2270 can be configured to provide more or less steps than those illustrated in FIGS. 52 and 53. The reader will also appreciate that the modules 2252 and/or 2270 are exemplary modules; various other modules can be executed by the processor 2242 to provide the user of the surgical instrument 2200 with instructions to perform the manual bailout.

In various instances, as described above, the processor 2242 can be configured to present to the user of the surgical instrument 2200 the steps and/or messages for performing a manual bailout in predetermined time intervals. Such time intervals may be the same or may vary depending on the complexity of the task to be performed by the user, for example. In certain instances, such time intervals can be any time interval in the range of about 1 second, for example, to about 10 minutes, for example. In certain instances, such time intervals can be any time interval in the range of about 1 second, for example, to about 1 minute, for example. Other time intervals are contemplated by the present disclosure.

In some instances, a power assembly, such as, for example the power assembly 2006 illustrated in FIGS. 31-33B, is configured to monitor the number of uses of the power assembly 2006 and/or a surgical instrument 2000 coupled to the power assembly 2006. The power assembly 2006 maintains a usage cycle count corresponding to the number of uses. The power assembly 2006 and/or the surgical instrument 2000 performs one or more actions based on the usage cycle count. For example, in some instances, when the usage cycle count exceeds a predetermined usage limit, the power assembly 2006 and/or a surgical instrument 2000 may disable the power assembly 2006, disable the surgical instrument 2000, indicate that a reconditioning or service cycle is required, provide a usage cycle count to an operator and/or a remote system, and/or perform any other suitable action. The usage cycle count is determined by any suitable system, such as, for example, a mechanical limiter, a usage cycle circuit, and/or any other suitable system coupled to the battery 2006 and/or the surgical instrument 2000.

Figure 54:
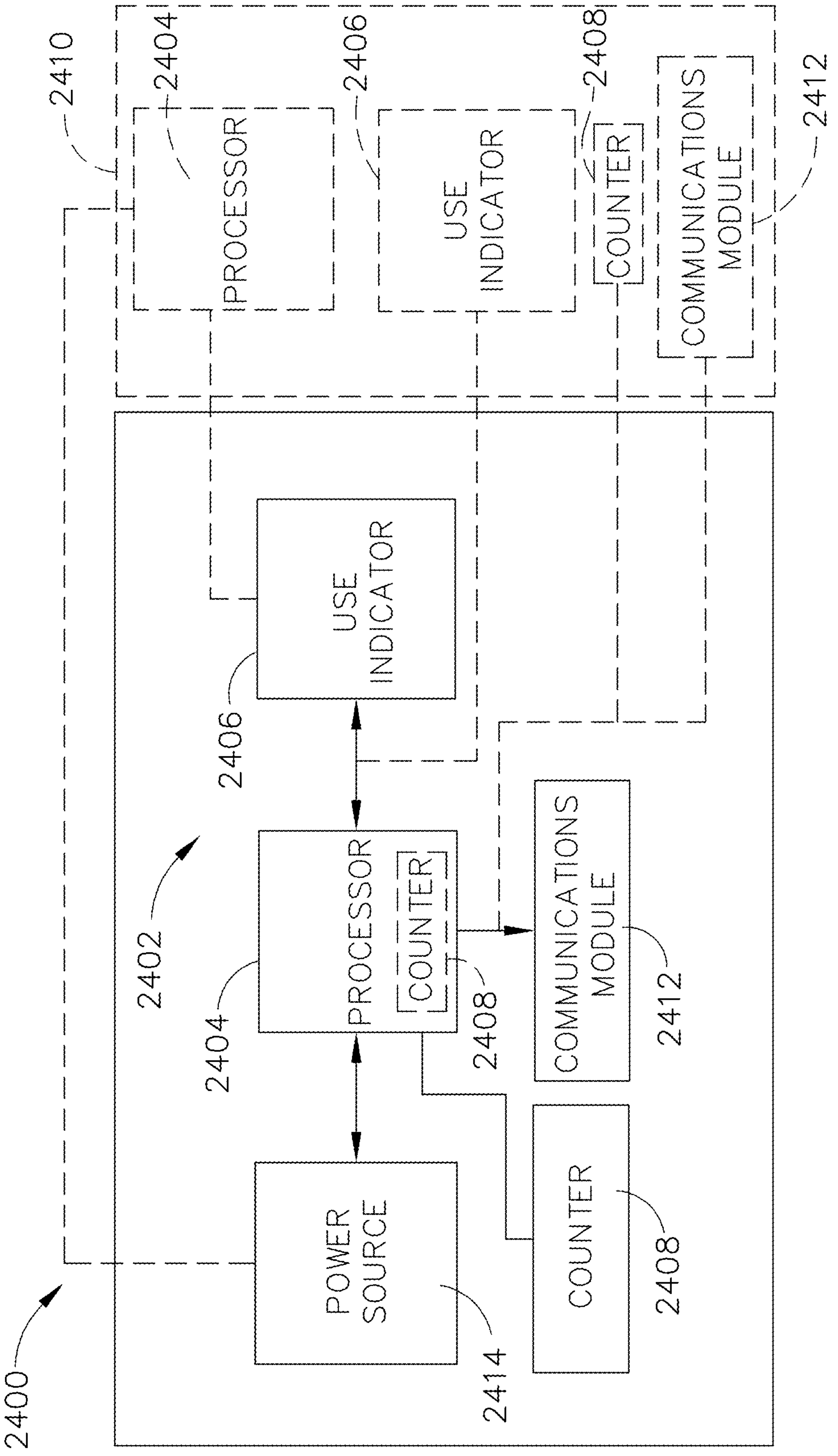
FIG. 54 illustrates one instance of a power assembly comprising a usage cycle circuit configured to generate a usage cycle count of the battery back.

FIG. 54 illustrates one example of a power assembly 2400 comprising a usage cycle circuit 2402 configured to monitor a usage cycle count of the power assembly 2400. The power assembly 2400 may be coupled to a surgical instrument 2410. The usage cycle circuit 2402 comprises a processor 2404 and a use indicator 2406. The use indicator 2406 is configured to provide a signal to the processor 2404 to indicate a use of the battery back 2400 and/or a surgical instrument 2410 coupled to the power assembly 2400. A "use" may comprise any suitable action, condition, and/or parameter such as, for example, changing a modular component of a surgical instrument 2410, deploying or firing a disposable component coupled to the surgical instrument 2410, delivering electrosurgical energy from the surgical instrument 2410, reconditioning the surgical instrument 2410 and/or the power assembly 2400, exchanging the power assembly 2400, recharging the power assembly 2400, and/or exceeding a safety limitation of the surgical instrument 2410 and/or the battery back 2400.

In some instances, a usage cycle, or use, is defined by one or more power assembly 2400 parameters. For example, in one instance, a usage cycle comprises using more than 5% of the total energy available from the power assembly 2400 when the power assembly 2400 is at a full charge level. In another instance, a usage cycle comprises a continuous energy drain from the power assembly 2400 exceeding a predetermined time limit. For example, a usage cycle may correspond to five minutes of continuous and/or total energy draw from the power assembly 2400. In some instances, the power assembly 2400 comprises a usage cycle circuit 2402 having a continuous power draw to maintain one or more components of the usage cycle circuit 2402, such as, for example, the use indicator 2406 and/or a counter 2408, in an active state.

The processor 2404 maintains a usage cycle count. The usage cycle count indicates the number of uses detected by the use indicator 2406 for the power assembly 2400 and/or the surgical instrument 2410. The processor 2404 may increment and/or decrement the usage cycle count based on input from the use indicator 2406. The usage cycle count is used to control one or more operations of the power assembly 2400 and/or the surgical instrument 2410. For example, in some instances, a power assembly 2400 is disabled when the usage cycle count exceeds a predetermined usage limit. Although the instances discussed herein are discussed with respect to incrementing the usage cycle count above a predetermined usage limit, those skilled in the art will recognize that the usage cycle count may start at a predetermined amount and may be decremented by the processor 2404. In this instance, the processor 2404 initiates and/or prevents one or more operations of the power assembly 2400 when the usage cycle count falls below a predetermined usage limit.

The usage cycle count is maintained by a counter 2408. The counter 2408 comprises any suitable circuit, such as, for example, a memory module, an analog counter, and/or any circuit configured to maintain a usage cycle count. In some instances, the counter 2408 is formed integrally with the processor 2404. In other instances, the counter 2408 comprises a separate component, such as, for example, a solid state memory module. In some instances, the usage cycle count is provided to a remote system, such as, for example, a central database. The usage cycle count is transmitted by a communications module 2412 to the remote system. The communications module 2412 is configured to use any suitable communications medium, such as, for example, wired and/or wireless communication. In some instances, the communications module 2412 is configured to receive one or more instructions from the remote system, such as, for example, a control signal when the usage cycle count exceeds the predetermined usage limit.

In some instances, the use indicator 2406 is configured to monitor the number of modular components used with a surgical instrument 2410 coupled to the power assembly 2400. A modular component may comprise, for example, a modular shaft, a modular end effector, and/or any other modular component. In some instances, the use indicator 2406 monitors the use of one or more disposable components, such as, for example, insertion and/or deployment of a staple cartridge within an end effector coupled to the surgical instrument 2410. The use indicator 2406 comprises one or more sensors for detecting the exchange of one or more modular and/or disposable components of the surgical instrument 2410.

In some instances, the use indicator 2406 is configured to monitor single patient surgical procedures performed while the power assembly 2400 is installed. For example, the use indicator 2406 may be configured to monitor firings of the surgical instrument 2410 while the power assembly 2400 is coupled to the surgical instrument 2410. A firing may correspond to deployment of a staple cartridge, application of electrosurgical energy, and/or any other suitable surgical event. The use indicator 2406 may comprise one or more circuits for measuring the number of firings while the power assembly 2400 is installed. The use indicator 2406 provides a signal to the processor 2404 when a single patient procedure is performed and the processor 2404 increments the usage cycle count.

In some instances, the use indicator 2406 comprises a circuit configured to monitor one or more parameters of the power source 2414, such as, for example, a current draw from the power source 2414. The one or more parameters of the power source 2414 correspond to one or more operations performable by the surgical instrument 2410, such as, for example, a cutting and sealing operation. The use indicator 2406 provides the one or more parameters to the processor 2404, which increments the usage cycle count when the one or more parameters indicate that a procedure has been performed.

In some instances, the use indicator 2406 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2400 is coupled to the surgical instrument 2410, the processor 2404 polls the use indicator 2406 to determine when the single patient procedure time has expired. When the predetermined time period has elapsed, the processor 2404 increments the usage cycle count. After incrementing the usage cycle count, the processor 2404 resets the timing circuit of the use indicator 2406.

Figure 55:
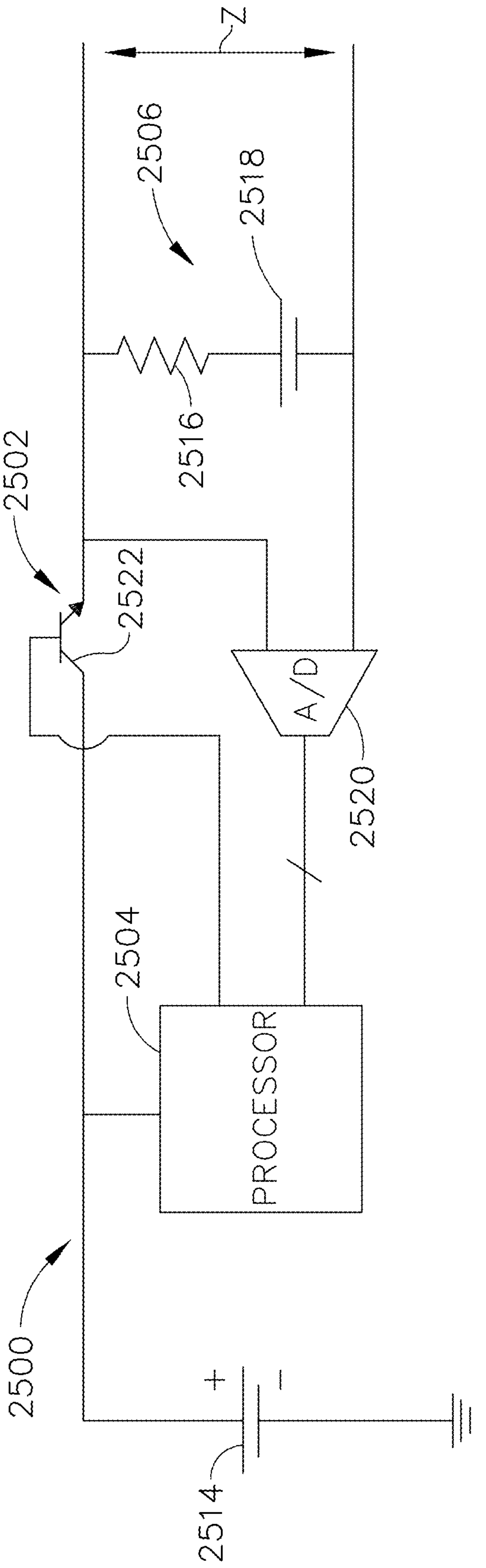
FIG. 55 illustrates one instance of a usage cycle circuit comprising a resistor-capacitor timer.

In some instances, the use indicator 2406 comprises a time constant that approximates the single patient procedure time. FIG. 55 illustrates one instance of power assembly 2500 comprising a usage cycle circuit 2502 having a resistor-capacitor (RC) timing circuit 2506. The RC timing circuit 2506 comprises a time constant defined by a resistor-capacitor pair. The time constant is defined by the values of the resistor 2516 and the capacitor 2518. When the power assembly 2500 is installed in a surgical instrument, a processor 2504 polls the RC timing circuit 2506. When one or more parameters of the RC timing circuit 2506 are below a predetermined threshold, the processor 2504 increments the usage cycle count. For example, the processor 2504 may poll the voltage of the capacitor 2518 of the resistor-capacitor pair 2506. When the voltage of the capacitor 2518 is below a predetermined threshold, the processor 2504 increment the usage cycle count. The processor 2504 may be coupled to the RC timing circuit 2506 by, for example, an A/D 2520. After incrementing the usage cycle count, the processor 2504 turns on a transistor 2522 to connect the RC timing circuit 2506 to a power source 2514 to charge the capacitor 2518 of the RC timing circuit 2506. Once the capacitor 2518 is fully charged, the transistor 2522 is opened and the RC timing circuit 2506 is allowed to discharge, as governed by the time constant, to indicate a subsequent single patient procedure.

Figure 56:
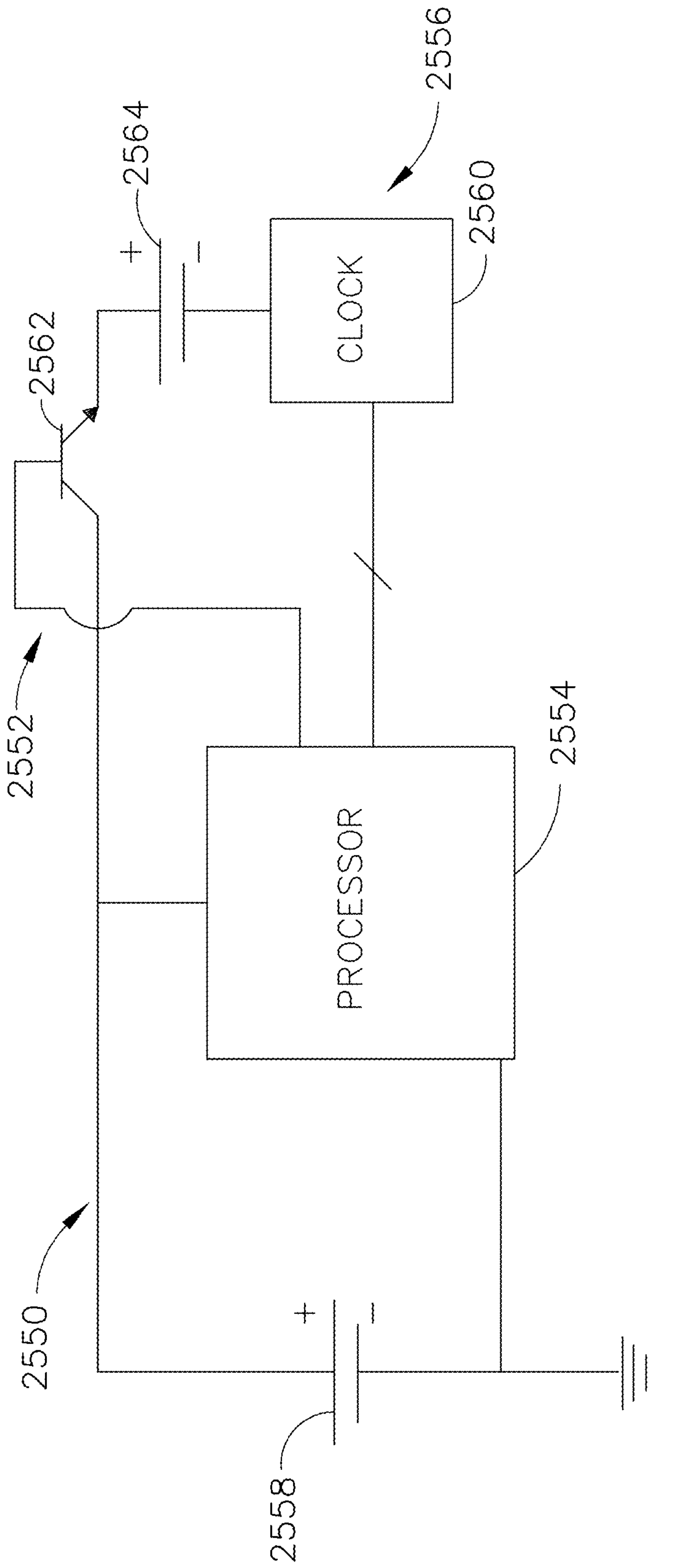
FIG. 56 illustrates one instance of a usage cycle circuit comprising a timer and a rechargeable battery.

FIG. 56 illustrates one instance of a power assembly 2550 comprising a usage cycle circuit 2552 having a rechargeable battery 2564 and a clock 2560. When the power assembly 2550 is installed in a surgical instrument, the rechargeable battery 2564 is charged by the power source 2558. The rechargeable battery 2564 comprises enough power to run the clock 2560 for at least the single patient procedure time. The clock 2560 may comprise a real time clock, a processor configured to implement a time function, or any other suitable timing circuit. The processor 2554 receives a signal from the clock 2560 and increments the usage cycle count when the clock 2560 indicates that the single patient procedure time has been exceeded. The processor 2554 resets the clock 2560 after incrementing the usage cycle count. For example, in one instance, the processor 2554 closes a transistor 2562 to recharge the rechargeable battery 2564. Once the rechargeable battery 2564 is fully charged, the processor 2554 opens the transistor 2562, and allows the clock 2560 to run while the rechargeable battery 2564 discharges.

Referring back to FIG. 54, in some instances, the use indicator 2406 comprises a sensor configured to monitor one or more environmental conditions experienced by the power assembly 2400. For example, the use indicator 2406 may comprise an accelerometer. The accelerometer is configured to monitor acceleration of the power assembly 2400. The power assembly 2400 comprises a maximum acceleration tolerance. Acceleration above a predetermined threshold indicates, for example, that the power assembly 2400 has been dropped. When the use indicator 2406 detects acceleration above the maximum acceleration tolerance, the processor 2404 increments a usage cycle count. In some instances, the use indicator 2406 comprises a moisture sensor. The moisture sensor is configured to indicate when the power assembly 2400 has been exposed to moisture. The moisture sensor may comprise, for example, an immersion sensor configured to indicate when the power assembly 2400 has been fully immersed in a cleaning fluid, a moisture sensor configured to indicate when moisture is in contact with the power assembly 2400 during use, and/or any other suitable moisture sensor.

In some instances, the use indicator 2406 comprises a chemical exposure sensor. The chemical exposure sensor is configured to indicate when the power assembly 2400 has come into contact with harmful and/or dangerous chemicals. For example, during a sterilization procedure, an inappropriate chemical may be used that leads to degradation of the power assembly 2400. The processor 2404 increments the usage cycle count when the use indicator 2406 detects an inappropriate chemical.

In some instances, the usage cycle circuit 2402 is configured to monitor the number of reconditioning cycles experienced by the power assembly 2400. A reconditioning cycle may comprise, for example, a cleaning cycle, a sterilization cycle, a charging cycle, routine and/or preventative maintenance, and/or any other suitable reconditioning cycle. The use indicator 2406 is configured to detect a reconditioning cycle. For example, the use indicator 2406 may comprise a moisture sensor to detect a cleaning and/or sterilization cycle. In some instances, the usage cycle circuit 2402 monitors the number of reconditioning cycles experienced by the power assembly 2400 and disables the power assembly 2400 after the number of reconditioning cycles exceeds a predetermined threshold.

The usage cycle circuit 2402 may be configured to monitor the number of power assembly 2400 exchanges. The usage cycle circuit 2402 increments the usage cycle count each time the power assembly 2400 is exchanged. When the maximum number of exchanges is exceeded, the usage cycle circuit 2402 locks out the power assembly 2400 and/or the surgical instrument 2410. In some instances, when the power assembly 2400 is coupled the surgical instrument 2410, the usage cycle circuit 2402 identifies the serial number of the power assembly 2400 and locks the power assembly 2400 such that the power assembly 2400 is usable only with the surgical instrument 2410. In some instances, the usage cycle circuit 2402 increments the usage cycle each time the power assembly 2400 is removed from and/or coupled to the surgical instrument 2410.

In some instances, the usage cycle count corresponds to sterilization of the power assembly 2400. The use indicator 2406 comprises a sensor configured to detect one or more parameters of a sterilization cycle, such as, for example, a temperature parameter, a chemical parameter, a moisture parameter, and/or any other suitable parameter. The processor 2404 increments the usage cycle count when a sterilization parameter is detected. The usage cycle circuit 2402 disables the power assembly 2400 after a predetermined number of sterilizations. In some instances, the usage cycle circuit 2402 is reset during a sterilization cycle, a voltage sensor to detect a recharge cycle, and/or any suitable sensor. The processor 2404 increments the usage cycle count when a reconditioning cycle is detected. The usage cycle circuit 2402 is disabled when a sterilization cycle is detected. The usage cycle circuit 2402 is reactivated and/or reset when the power assembly 2400 is coupled to the surgical instrument 2410. In some instances, the use indicator comprises a zero power indicator. The zero power indicator changes state during a sterilization cycle and is checked by the processor 2404 when the power assembly 2400 is coupled to a surgical instrument 2410. When the zero power indicator indicates that a sterilization cycle has occurred, the processor 2404 increments the usage cycle count.

A counter 2408 maintains the usage cycle count. In some instances, the counter 2408 comprises a non-volatile memory module. The processor 2404 increments the usage cycle count stored in the non-volatile memory module each time a usage cycle is detected. The memory module may be accessed by the processor 2404 and/or a control circuit, such as, for example, the control circuit 1100. When the usage cycle count exceeds a predetermined threshold, the processor 2404 disables the power assembly 2400. In some instances, the usage cycle count is maintained by a plurality of circuit components. For example, in one instance, the counter 2408 comprises a resistor (or fuse) pack. After each use of the power assembly 2400, a resistor (or fuse) is burned to an open position, changing the resistance of the resistor pack. The power assembly 2400 and/or the surgical instrument 2410 reads the remaining resistance. When the last resistor of the resistor pack is burned out, the resistor pack has a predetermined resistance, such as, for example, an infinite resistance corresponding to an open circuit, which indicates that the power assembly 2400 has reached its usage limit. In some instances, the resistance of the resistor pack is used to derive the number of uses remaining.

In some instances, the usage cycle circuit 2402 prevents further use of the power assembly 2400 and/or the surgical instrument 2410 when the usage cycle count exceeds a predetermined usage limit. In one instance, the usage cycle count associated with the power assembly 2400 is provided to an operator, for example, utilizing a screen formed integrally with the surgical instrument 2410. The surgical instrument 2410 provides an indication to the operator that the usage cycle count has exceeded a predetermined limit for the power assembly 2400, and prevents further operation of the surgical instrument 2410.

In some instances, the usage cycle circuit 2402 is configured to physically prevent operation when the predetermined usage limit is reached. For example, the power assembly 2400 may comprise a shield configured to deploy over contacts of the power assembly 2400 when the usage cycle count exceeds the predetermined usage limit. The shield prevents recharge and use of the power assembly 2400 by covering the electrical connections of the power assembly 2400.

In some instances, the usage cycle circuit 2402 is located at least partially within the surgical instrument 2410 and is configured to maintain a usage cycle count for the surgical instrument 2410. FIG. 54 illustrates one or more components of the usage cycle circuit 2402 within the surgical instrument 2410 in phantom, illustrating the alternative positioning of the usage cycle circuit 2402. When a predetermined usage limit of the surgical instrument 2410 is exceeded, the usage cycle circuit 2402 disables and/or prevents operation of the surgical instrument 2410. The usage cycle count is incremented by the usage cycle circuit 2402 when the use indicator 2406 detects a specific event and/or requirement, such as, for example, firing of the surgical instrument 2410, a predetermined time period corresponding to a single patient procedure time, based on one or more motor parameters of the surgical instrument 2410, in response to a system diagnostic indicating that one or more predetermined thresholds are met, and/or any other suitable requirement. As discussed above, in some instances, the use indicator 2406 comprises a timing circuit corresponding to a single patient procedure time. In other instances, the use indicator 2406 comprises one or more sensors configured to detect a specific event and/or condition of the surgical instrument 2410.

In some instances, the usage cycle circuit 2402 is configured to prevent operation of the surgical instrument 2410 after the predetermined usage limit is reached. In some instances, the surgical instrument 2410 comprises a visible indicator to indicate when the predetermined usage limit has been reached and/or exceeded. For example, a flag, such as a red flag, may pop-up from the surgical instrument 2410, such as from the handle, to provide a visual indication to the operator that the surgical instrument 2410 has exceeded the predetermined usage limit. As another example, the usage cycle circuit 2402 may be coupled to a display formed integrally with the surgical instrument 2410. The usage cycle circuit 2402 displays a message indicating that the predetermined usage limit has been exceeded. The surgical instrument 2410 may provide an audible indication to the operator that the predetermined usage limit has been exceeded. For example, in one instance, the surgical instrument 2410 emits an audible tone when the predetermined usage limit is exceeded and the power assembly 2400 is removed from the surgical instrument 2410. The audible tone indicates the last use of the surgical instrument 2410 and indicates that the surgical instrument 2410 should be disposed or reconditioned.

In some instances, the usage cycle circuit 2402 is configured to transmit the usage cycle count of the surgical instrument 2410 to a remote location, such as, for example, a central database. The usage cycle circuit 2402 comprises a communications module 2412 configured to transmit the usage cycle count to the remote location. The communications module 2412 may utilize any suitable communications system, such as, for example, wired or wireless communications system. The remote location may comprise a central database configured to maintain usage information. In some instances, when the power assembly 2400 is coupled to the surgical instrument 2410, the power assembly 2400 records a serial number of the surgical instrument 2410. The serial number is transmitted to the central database, for example, when the power assembly 2400 is coupled to a charger. In some instances, the central database maintains a count corresponding to each use of the surgical instrument 2410. For example, a bar code associated with the surgical instrument 2410 may be scanned each time the surgical instrument 2410 is used. When the use count exceeds a predetermined usage limit, the central database provides a signal to the surgical instrument 2410 indicating that the surgical instrument 2410 should be discarded.

The surgical instrument 2410 may be configured to lock and/or prevent operation of the surgical instrument 2410 when the usage cycle count exceeds a predetermined usage limit. In some instances, the surgical instrument 2410 comprises a disposable instrument and is discarded after the usage cycle count exceeds the predetermined usage limit. In other instances, the surgical instrument 2410 comprises a reusable surgical instrument which may be reconditioned after the usage cycle count exceeds the predetermined usage limit. The surgical instrument 2410 initiates a reversible lockout after the predetermined usage limit is met. A technician reconditions the surgical instrument 2410 and releases the lockout, for example, utilizing a specialized technician key configured to reset the usage cycle circuit 2402.

Figure 57:
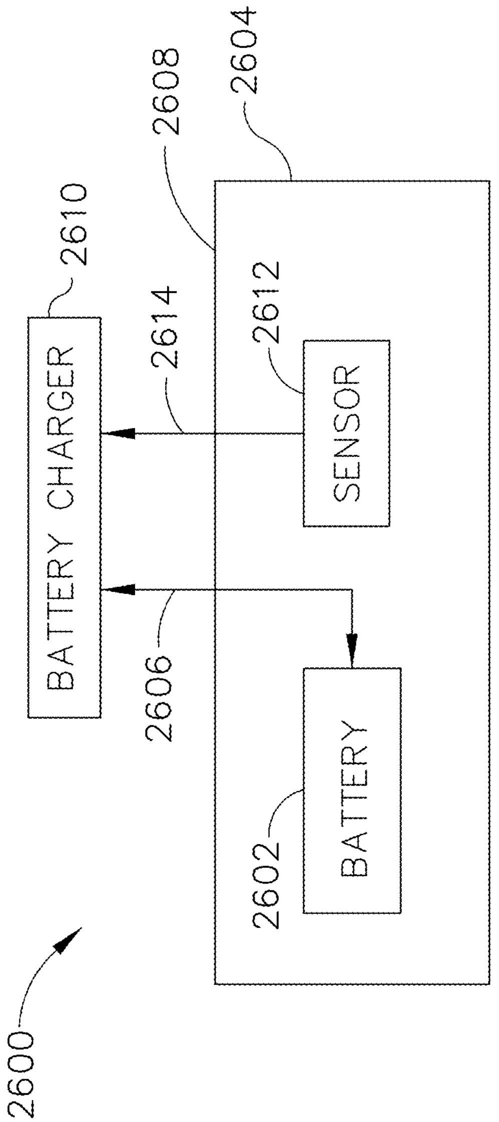
FIG. 57 illustrates one instance of a combination sterilization and charging system configured to sterilize and charge a power assembly simultaneously.

In some instances, the power assembly 2400 is charged and sterilized simultaneously prior to use. FIG. 57 illustrates one instance of a combined sterilization and charging system 2600 configured to charge and sterilize a battery 2602 simultaneously. The combined sterilization and charging system 2600 comprises a sterilization chamber 2604. A battery 2602 is placed within the sterilization chamber 2604. In some instances, the battery 2602 is coupled to a surgical instrument. A charging cable 2606 is mounted through a wall 2608 of the sterilization chamber 2604.

The wall 2608 is sealed around the charging cable 2606 to maintain a sterile environment within the sterilization chamber 2604 during sterilization. The charging cable 2606 comprises a first end configured to couple to the power assembly 2602 within the sterilization chamber 2604 and a second end coupled to a battery charger 2610 located outside of the sterilization chamber 2604. Because the charging cable 2606 passes through the wall 2608 of the sterilization chamber 2604 while maintaining a sterile environment within the sterilization chamber 2604, the power assembly 2602 may be charged and sterilized simultaneously.

The charging profile applied by the battery charger 2610 is configured to match the sterilization cycle of the sterilization chamber 2604. For example, in one instance, a sterilization procedure time is about 28 to 38 minutes. The battery charger 2610 is configured to provide a charging profile that charges the battery during the sterilization procedure time. In some instances, the charging profile may extend over a cooling-off period following the sterilization procedure. The charging profile may be adjusted by the battery charger 2610 based on feedback from the power assembly 2602 and/or the sterilization chamber 2604. For example, in one instance, a sensor 2612 is located within the sterilization chamber 2604. The sensor 2612 is configured to monitor one or more characteristics of the sterilization chamber 2604, such as, for example, chemicals present in the sterilization chamber 2604, temperature of the sterilization chamber 2604, and/or any other suitable characteristic of the sterilization chamber 2604. The sensor 2612 is coupled to the battery charger 2610 by a cable 2614 extending through the wall 2608 of the sterilization chamber 2604. The cable 2614 is sealed such that the sterilization chamber 2604 may maintain a sterile environment. The battery charger 2610 adjusts the charging profile based on feedback from the sensor 2614. For example, in one instance, the battery charger 2610 receives temperature data from the sensor 2612 and adjusts the charging profile when the temperature of the sterilization chamber 2604 and/or the power assembly 2602 exceeds a predetermined temperature. As another example, the battery charger 2610 receives chemical composition information from the sensor 2612 and prevents charging of the power assembly 2602 when a chemical, such as, for example, $H_2O_2$, approaches explosive limits.

Figure 58:
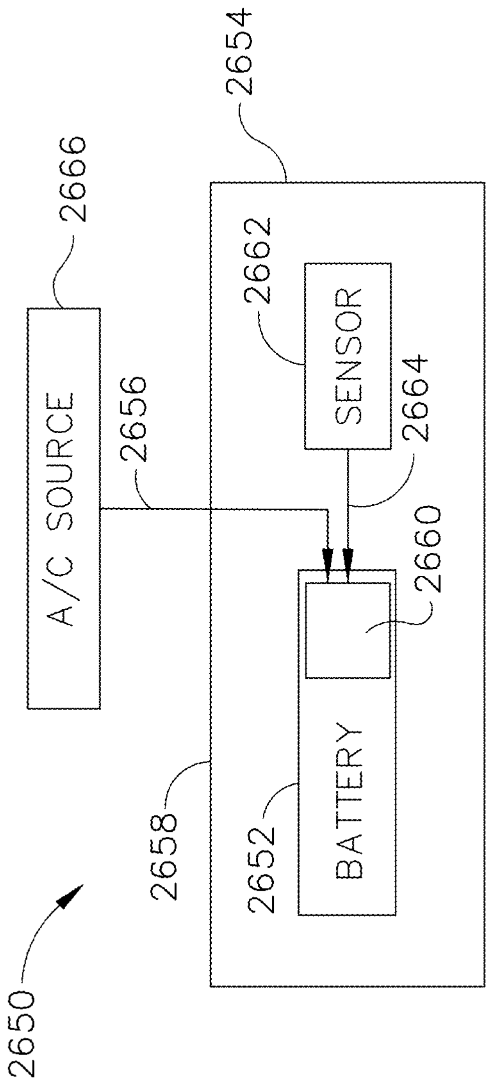
FIG. 58 illustrates one instance of a combination sterilization and charging system configured to sterilize and charge a power assembly having a battery charger formed integrally therein.

FIG. 58 illustrates one instance of a combination sterilization and charging system 2650 configured for a power assembly 2652 having a battery charger 2660 formed integrally therewith. An alternating current (AC) source 2666 is located outside of the sterilization chamber 2654 and is coupled the battery charger 2660 by an AC cable 2656 mounted through a wall 2658 of the sterilization chamber 2654. The wall 2658 is sealed around the AC cable 2656. The battery charger 2660 operates similar to the battery charger 2610 illustrated in FIG. 57. In some instances, the battery charger 2660 receives feedback from a sensor 2662 located within the sterilization chamber 2654 and coupled to the battery charger 2660 by a cable 2664.

Figure 62:
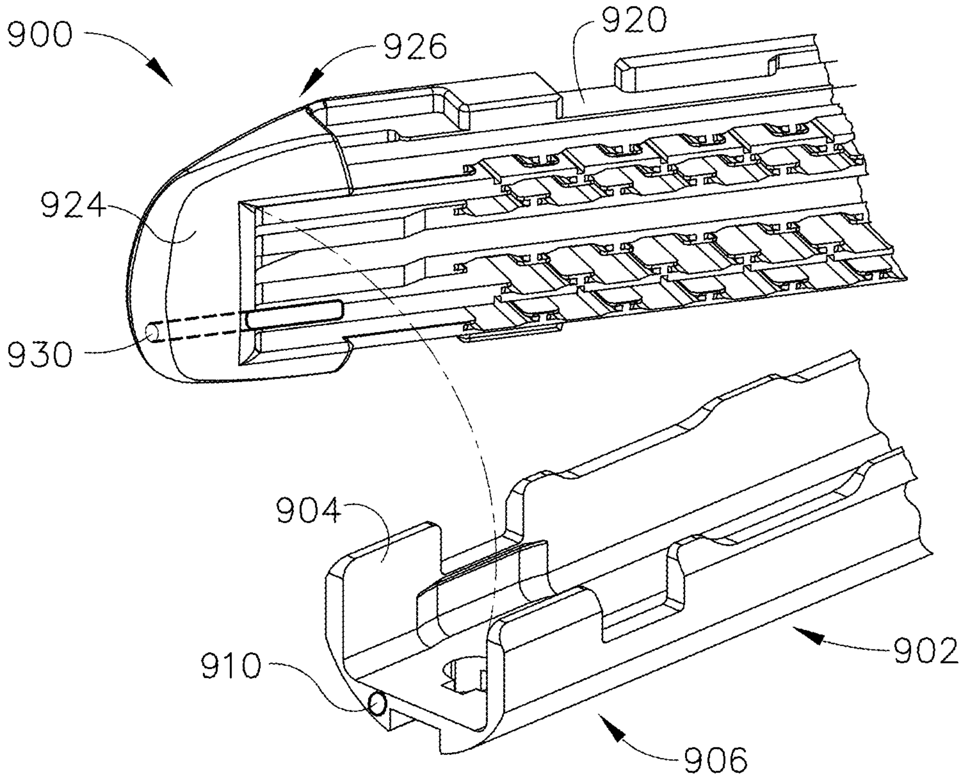
FIG. 62 is a partial, perspective view of an end effector and a fastener cartridge according to various embodiments of the present disclosure.

In various instances, a surgical system can include a magnet and a sensor. In combination, the magnet and the sensor can cooperate to detect various conditions of a fastener cartridge, such as the presence of a fastener cartridge in an end effector of the surgical instrument, the type of fastener cartridge loaded in the end effector, and/or the firing state of a loaded fastener cartridge, for example. Referring now to FIG. 62, a jaw 902 of an end effector 900 can comprise a magnet 910, for example, and a fastener cartridge 920 can comprise a sensor 930, for example. In various instances, the magnet 910 can be positioned at the distal end 906 of an elongate channel 904 sized and configured to receive the fastener cartridge 920. Furthermore, the sensor 930 can be at least partially embedded or retained in the distal end 926 of the nose 924 of the fastener cartridge 920, for example. In various instances, the sensor 924 can be in signal communication with the microcontroller of the surgical instrument.

In various circumstances, the sensor 930 can detect the presence of the magnet 910 when the fastener cartridge 920 is positioned in the elongate channel 904 of the jaw 902. The sensor 930 can detect when the fastener cartridge 920 is improperly positioned in the elongate channel 904 and/or not loaded into the elongate channel 904, for example, and can communicate the cartridge loading state to the microcontroller of the surgical system, for example. In certain instances, the magnet 910 can be positioned in the fastener cartridge 920, for example, and the sensor 930 can be positioned in the end effector 900, for example. In various instances, the sensor 930 can detect the type of fastener cartridge 920 loaded in the end effector 900. For example, different types of fastener cartridges can have different magnetic arrangements, such as different placement(s) relative to the cartridge body or other cartridge components, different polarities, and/or different magnetic strengths, for example. In such instances, the sensor 930 can detect the type of cartridge, e.g., the cartridge length, the number of fasteners and/or the fastener height(s), positioned in the jaw 902 based on the detected magnetic signal. Additionally or alternatively, the sensor 930 can detect if the fastener cartridge 920 is properly seated in the end effector 900. For example, the end effector 900 and the fastener cartridge 920 can comprise a plurality of magnets and/or a plurality of sensors and, in certain instances, the sensor(s) can detect whether the fastener cartridge 920 is properly positioned and/or aligned based on the position of multiple magnets relative to the sensor(s), for example.

Figure 63:
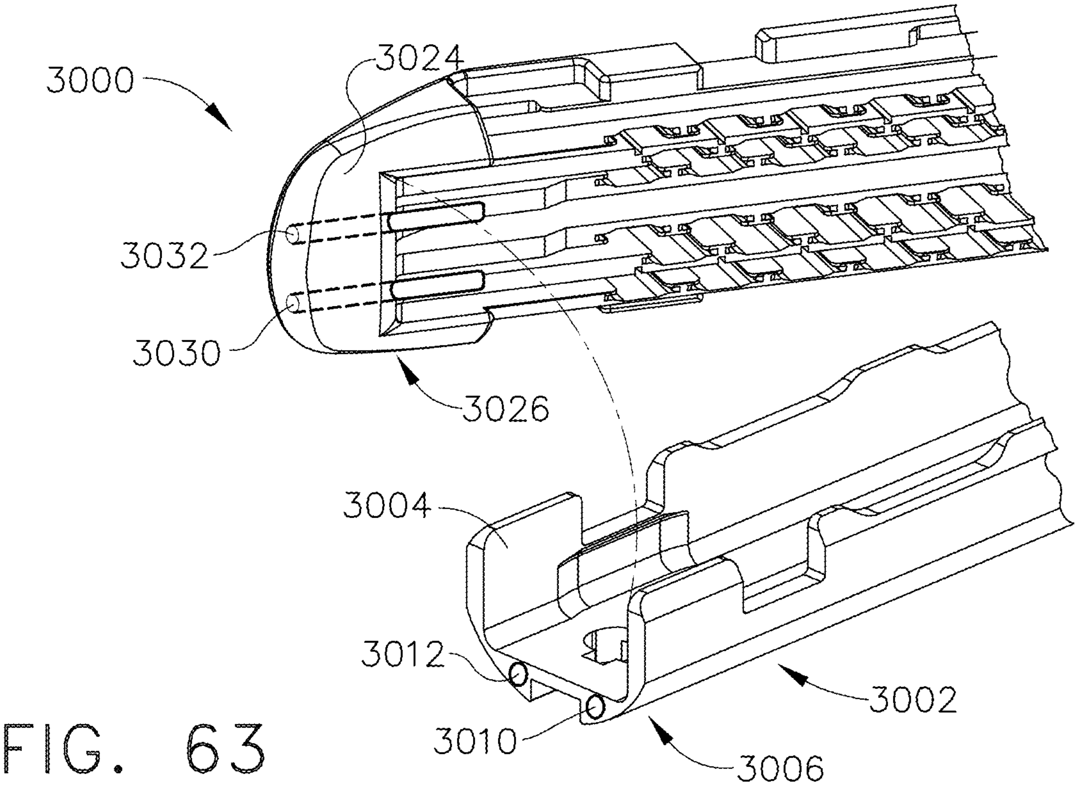
FIG. 63 is partial, perspective view of an end effector and a fastener cartridge according to various embodiments of the present disclosure.

Referring now to FIG. 63, in certain instances, an end effector 3000 can include a plurality of magnets and a plurality of sensors. For example, a jaw 3002 can include a plurality of magnets 3010, 3012 positioned at the distal end 3006 thereof. Moreover, the fastener cartridge 3020 can include a plurality of sensors 3030, 3032 positioned at the distal end 3026 of the nose 3024, for example. In certain instances, the sensors 3030, 3032 can detect the presence of the fastener cartridge 3020 in the elongate channel 3004 of the jaw 3002. In various instances, the sensors 3030, 3032 can comprise Hall Effect sensors, for example. Various sensors are described in U.S. Pat. No. 8,210,411, filed Sep. 23, 2008, and entitled MOTOR-DRIVEN SURGICAL CUTTING INSTRUMENT. U.S. Pat. No. 8,210,411, filed Sep. 23, 2008, and entitled MOTOR-DRIVEN SURGICAL CUTTING INSTRUMENT, is hereby incorporated by reference in its entirety. The addition of an additional sensor or sensors can provide a greater bandwidth signal, for example, which can provide further and/or improved information to the microcontroller of the surgical instrument. Additionally or alternatively, additional sensors can determine if the fastener cartridge 3020 is properly seated in the elongate channel of the jaw 3002, for example.

Figure 64:
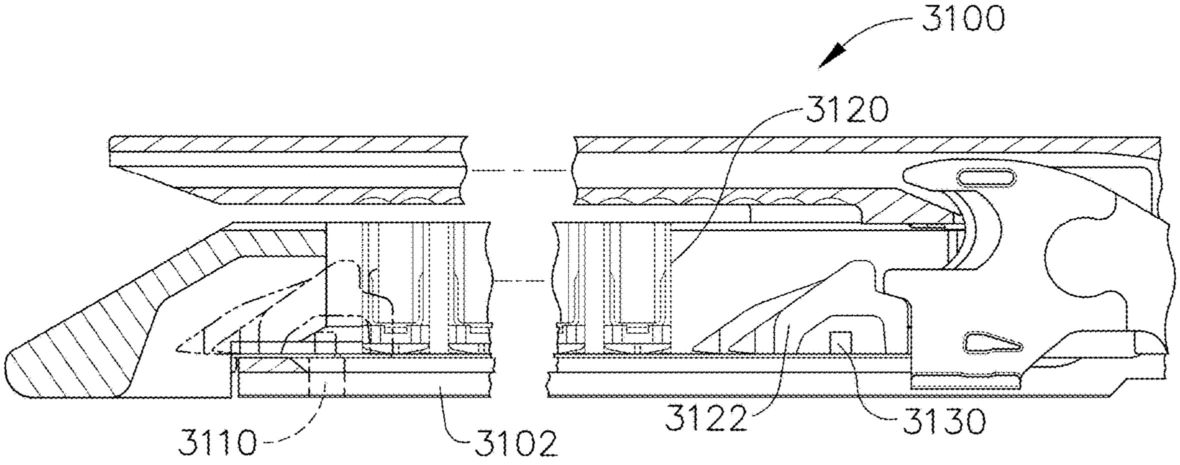
FIG. 64 is a cross-sectional, elevation view of an end effector and a fastener cartridge according to various embodiments of the present disclosure.
Figure 65:
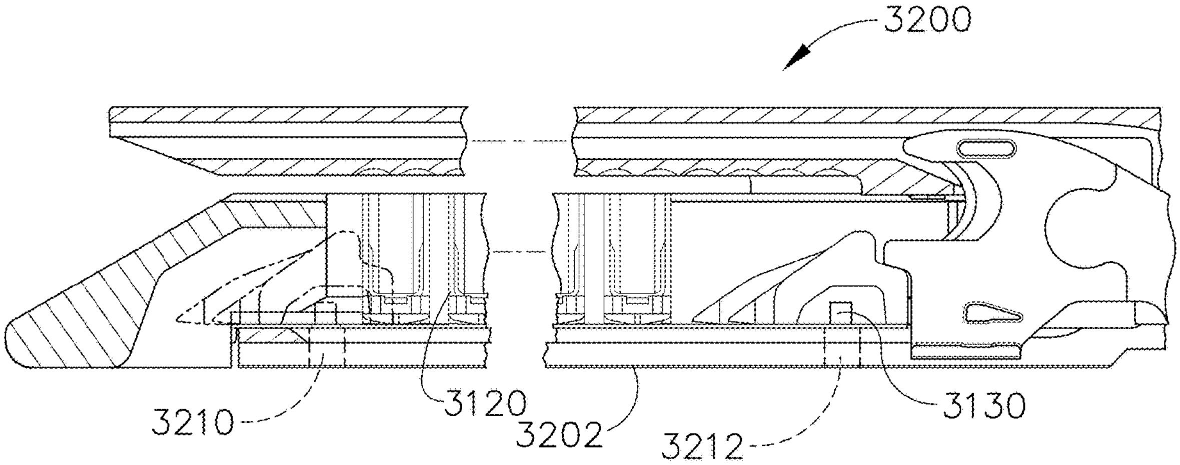
FIG. 65 is a cross-sectional, elevation view of an end effector and a fastener cartridge according to various embodiments of the present disclosure.

In various instances, a magnet can be positioned on a moveable component of a fastener cartridge. For example, a magnet can be positioned on a component of the fastener cartridge that moves during a firing stroke. In such instances, a sensor in the end effector can detect the firing state of the fastener cartridge. For example, referring now to FIG. 64, a magnet 3130 can be positioned on the sled 3122 of a fastener cartridge 3120. Moreover, a sensor 1110 can be positioned in the jaw 3102 of the end effector 3100. In various circumstances, the sled 3122 can translate during a firing stroke. Moreover, in certain instances, the sled 3120 can remain at the distal end of the fastener cartridge 3120 after the firing stroke. Stated differently, after the cartridge has been fired, the sled 3120 can remain at the distal end of the fastener cartridge 3120. Accordingly, the sensor 3110 can detect the position of the magnet 3130 and the corresponding sled 3120 to determine the firing state of the fastener cartridge 3120. For example, when the sensor 3110 detects the proximal position of the magnet 3130, the fastener cartridge 3120 can be unfired and ready to fire, for example, and when the sensor 3110 detects the distal position of the magnet 3130, the fastener cartridge 3120 can be spent, for example. Referring now to FIG. 65, in various instances, a jaw 3202 of an end effector 3200 can include a plurality of sensors 3210, 3212. For example, a proximal sensor 3212 can be positioned in the proximal portion of the jaw 3202, and a distal sensor 3210 can be positioned in the distal portion of the jaw 3202, for example. In such instances, the sensors 3210, 3212 can detect the position of the sled 3122 as the sled 3122 moves during a firing stroke, for example. In various instances, the sensors 3210, 3212 can comprise Hall Effect sensors, for example.

Figure 66:
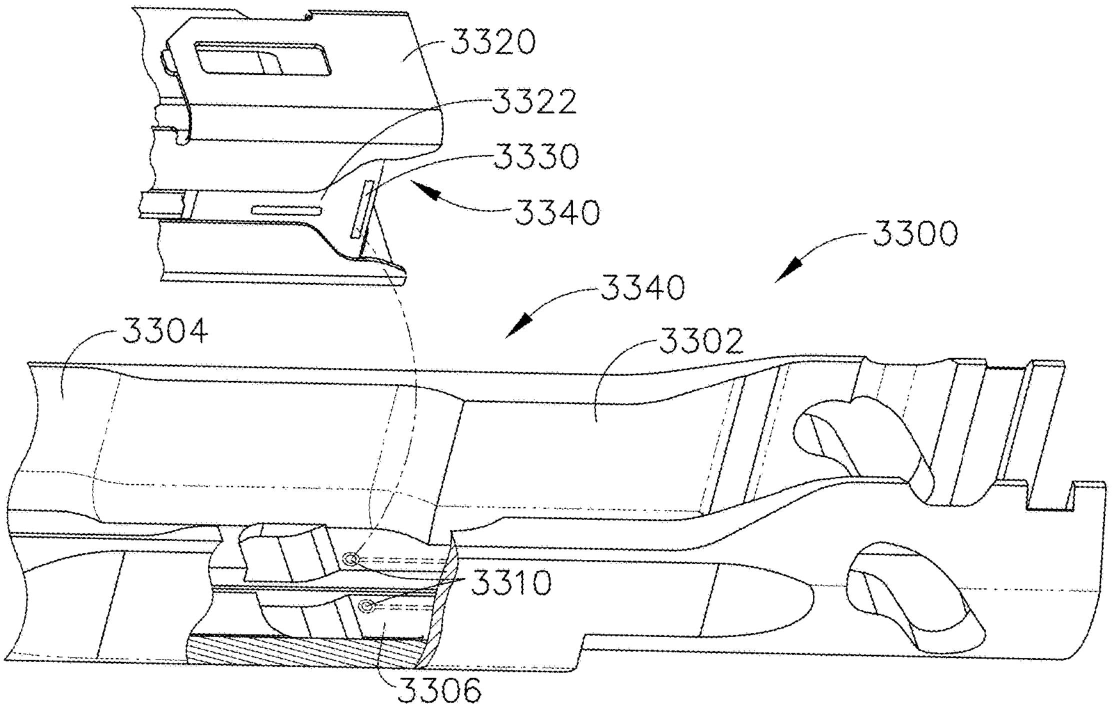
FIG. 66 is a partial, perspective view of an end effector with portions removed and a fastener cartridge according to various embodiments of the present disclosure.

Additionally or alternatively, an end effector can include a plurality of electrical contacts, which can detect the presence and/or firing state of a fastener cartridge. Referring now to FIG. 66, an end effector 3300 can include a jaw 3302 defining a channel 3304 configured to receive a fastener cartridge 3320. In various instances, the jaw 3302 and the fastener cartridge 3320 can comprise electrical contacts. For example, the elongate channel 3304 can define a bottom surface 3306, and an electrical contact 3310 can be positioned on the bottom surface 3306. In various instances, a plurality of electrical contacts 3310 can be defined in the elongate channel 3304. The electrical contacts 3310 can form part of a firing-state circuit 3340, which can be in signal communication with a microcontroller of the surgical system. For example, the electrical contacts 3310 can be electrically coupled to and/or in communication with a power supply, and can form electrically active ends of an open circuit, for example. In some instances, one of the electrical contacts 3310 can be powered such that a voltage potential is created intermediate the electrical contacts 3310. In certain instances, one of the contacts can be coupled to an output channel of the microprocessor, for example, which can apply a voltage potential to the contact. Another contact can be coupled to an input channel of the microprocessor, for example. In certain instances, the electrical contacts 3310 can be insulated from the frame 3306 of the jaw 3302. Referring still to FIG. 66, the fastener cartridge 3320 can also include an electrical contact 3330, or a plurality of electrical contacts, for example. In various instances, the electrical contact 3330 can be positioned on a moveable element of the fastener cartridge 3320. For example, the electrical contact 3330 can be positioned on the sled 3322 of the fastener cartridge 3320, and thus, the electrical contact 3330 can move in the fastener cartridge 3320 during a firing stroke.

In various instances, the electrical contact 3330 can comprise a metallic bar or plate on the sled 3320, for example. The electrical contact 3330 in the fastener cartridge 3320 can cooperate with the electrical contact(s) 3310 in the end effector 3300, for example. In certain circumstances, the electrical contact 3330 can contact the electrical contact(s) 3310 when the sled 3322 is positioned in a particular position, or a range of positions, in the fastener cartridge 3320. For example, the electrical contact 3330 can contact the electrical contacts 3310 when the sled 3322 is unfired, and thus, positioned in a proximal position in the fastener cartridge 3320. In such circumstances, the electrical contact 3330 can close the circuit between the electrical contacts 3310, for example. Moreover, the firing-state circuit 3340 can communicate the closed circuit, i.e., the unfired cartridge indication, to the microcontroller of the surgical system. In such instances, when the sled 3322 is fired distally during a firing stroke, the electrical contact 3330 can move out of electrically contact with the electrical contacts 3310, for example. Accordingly, the firing-state circuit 3340 can communicate the open circuit, i.e., the fired cartridge indication, to the microcontroller of the surgical system. In certain circumstances, the microcontroller may only initiate a firing stroke when an unspent cartridge is indicated by the firing-state circuit 3340, for example. In various instances, the electrical contact 3330 can comprise an electromechanical fuse. In such instances, the fuse can break or short when the sled 3322 is fired through a firing stroke, for example.

Figure 67:
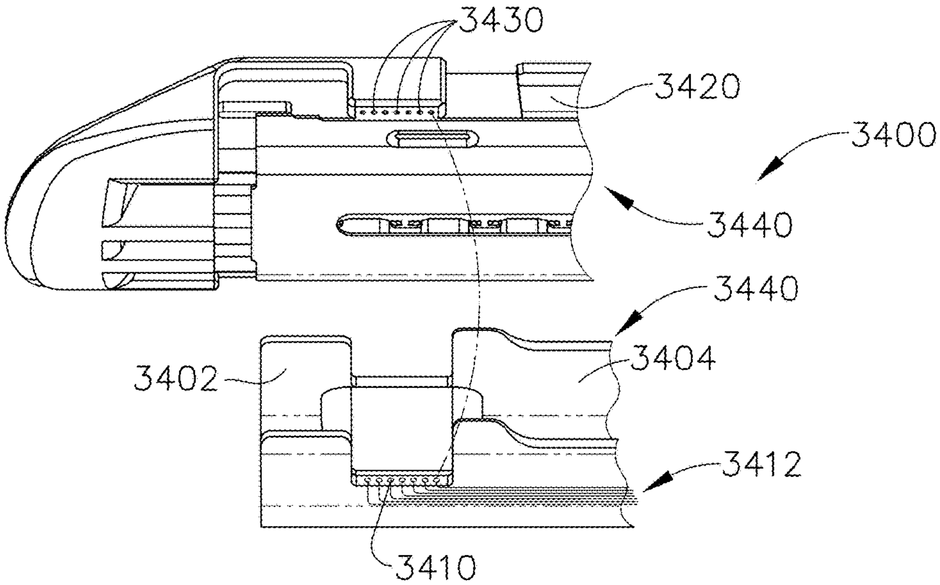
FIG. 67 is a partial, perspective view of an end effector with portions removed and a fastener cartridge according to various embodiments of the present disclosure.

Additionally or alternatively, referring now to FIG. 67, an end effector 3400 can include a jaw 3402 and a cartridge-present circuit 3440. In various instances, the jaw 3402 can comprise an electrical contact 3410, or a plurality of electrical contacts 3410, in an elongate channel 3404 thereof, for example. Furthermore, a fastener cartridge 3420 can include an electrical contact 3430, or a plurality of electrical contacts 3430, on an outer surface of the fastener cartridge 3420. In various instances, the electrical contacts 3430 can be positioned and/or mounted to a fixed or stationary component of the fastener cartridge 3420, for example. In various circumstances, the electrical contacts 3430 of the fastener cartridge 3420 can contact the electrical contacts 3410 of the end effector 3400 when the fastener cartridge 3420 is loaded into the elongate channel 3404, for example. Prior to placement of the fastener cartridge 3420 in the elongate channel 3404, the cartridge-present circuit 3440 can be an open circuit, for example. When the fastener cartridge 3420 is properly seated in the jaw 3402, the electrical contacts 3410 and 3430 can form the closed cartridge-present circuit 3440. In instances where the jaw 3402 and/or the fastener cartridge 3420 comprise a plurality of electrical contacts 3410, 3430, the cartridge-present circuit 3440 can comprise a plurality of circuits. Moreover, in certain instances, the cartridge-present circuit 3440 can identify the type of cartridge loaded in the jaw 3402 based on the number and/or arrangement of electrical contacts 3430 on the fastener cartridge 3420, for example, and the corresponding open and/or closed circuits of the cartridge-present circuit 3440, for example.

Moreover, the electrical contacts 3410 in the jaw 3402 can be in signal communication with the microcontroller of the surgical system. The electrical contacts 3410 can be wired to a power source, for example, and/or can communicate with the microcontroller via a wired and/or wireless connection, for example. In various instances, the cartridge-present circuit 3440 can communicate the cartridge presence or absence to the microcontroller of the surgical system. In various instances, a firing stroke may be prevented when the cartridge-present circuit 3440 indicates the absence of a fastener cartridge in the end effector jaw 3402, for example. Moreover, a firing stroke may be permitted when the cartridge—present circuit 3440 indicates the presence of a fastener cartridge 3420 in the end effector jaw 3402.

As described throughout the present disclosure, various sensors, programs, and circuits can detect and measure numerous characteristics of the surgical instrument and/or components thereof, surgical use or operation, and/or the tissue and/or operating site. For example, tissue thickness, the identification of the instrument components, usage and feedback data from surgical functions, and error or fault indications can be detected by the surgical instrument. In certain instances, the fastener cartridge can include a nonvolatile memory unit, which can be embedded or removably coupled to the fastener cartridge, for example. Such a nonvolatile memory unit can be in signal communication with the microcontroller via hardware, such as the electrical contacts described herein, radio frequency, or various other suitable forms of data transmission. In such instances, the microcontroller can communicate data and feedback to the nonvolatile memory unit in the fastener cartridge, and thus, the fastener cartridge can store information. In various instances, the information can be securely stored and access thereto can be restricted as suitable and appropriate for the circumstances.

In certain instances, the nonvolatile memory unit can comprise information regarding the fastener cartridge characteristics and/or the compatibility thereof with various other components of the modular surgical system. For example, when the fastener cartridge is loaded into an end effector, the nonvolatile memory unit can provide compatibility information to the microcontroller of the surgical system. In such instances, the microcontroller can verify the validity or compatibility of the modular assembly. For example, the microcontroller can confirm that the handle component can fire the fastener cartridge and/or that the fastener cartridge appropriate fits the end effector, for example. In certain circumstances, the microcontroller can communicate the compatibility or lack thereof to the operator of the surgical system, and/or may prevent a surgical function if the modular components are incompatible, for example.

As described herein, the surgical instrument can include a sensor, which can cooperate with a magnet to detect various characteristics of the surgical instrument, operation, and surgical site. In certain instances, the sensor can comprise a Hall Effect sensor and, in other instances, the sensor can comprise a magnetoresistive sensor as depicted in FIGS. 68(A)-68(C), for example. As described in greater detail herein, a surgical end effector can comprise a first jaw, which can be configured to receive a fastener cartridge, and a second jaw. The first jaw and/or the fastener cartridge can comprise a magnetic element, such as a permanent magnet, for example, and the second jaw can comprise a magnetoresistive sensor, for example. In other instances, the first jaw and/or the fastener cartridge can comprise a magnetoresistive sensor, for example, and the second jaw can comprise a magnetic element. The magnetoresistive sensor may have various characteristics listed in the table in FIG. 68(C), for example, and/or similar specifications, for example. In certain instances, the change in resistance caused by movement of the magnetic element relative to the magnetoresistive sensor can affect and/or vary the properties of the magnetic circuit depicted in FIG. 68(B), for example.

In various instances, the magnetoresistive sensor can detect the position of the magnetic element, and thus, can detect the thickness of tissue clamped between the opposing first and second jaws, for example. The magnetoresistive sensor can be in signal communication with the microcontroller, and the magnetoresistive sensor can wirelessly transmit data to an antenna in signal communication with the microcontroller, for example. In various instances, a passive circuit can comprise the magnetoresistive sensor. Moreover, the antenna can be positioned in the end effector, and can detect a wireless signal from the magnetoresistive sensor and/or microprocessor operably coupled thereto, for example. In such circumstances, an exposed electrical connection between the end effector comprising the antenna, for example, and the fastener cartridge comprising the magnetoresistive sensor, for example, can be avoided. Furthermore, in various instances, the antenna can be wired and/or in wireless communication with the microcontroller of the surgical instrument.

Tissue can contain fluid and, when the tissue is compressed, the fluid may be pressed from the compressed tissue. For example, when tissue is clamped between opposing jaws of a surgical end effector, fluid may flow and/or be displaced from the clamped tissue. Fluid flow or displacement in clamped tissue can depend on various characteristics of the tissue, such as the thickness and/or type of tissue, as well as various characteristics of the surgical operation, such as the desired tissue compression and/or the elapsed clamping time, for example. In various instances, fluid displacement between the opposing jaws of an end effector may contribute to malformation of staples formed between the opposing jaws. For example, the displacement of fluid during and/or following staple formation can induce bending and/or other uncontrolled movement of a staple away from its desired or intended formation. Accordingly, in various instances, it may be desirable to control the firing stroke, e.g., to control the firing speed, in relationship to the detected fluid flow, or lack thereof, intermediate opposing jaws of a surgical end effector.

In various instances, the fluid displacement in clamped tissue can be determined or approximated by various measurable and/or detectable tissue characteristics. For example, the degree of tissue compression can correspond to the degree of fluid displacement in the clamped tissue. In various instances, a higher degree of tissue compression can correspond to more fluid flow, for example, and a reduced degree of tissue compression can correspond to less fluid flow, for example. In various circumstances, a sensor positioned in the end effector jaws can detect the force exerted on the jaws by the compressed tissue. Additionally or alternatively, a sensor on or operably associated with the cutting element can detect the resistance on the cutting element as the cutting element is advanced through, and transects, the clamped tissue. In such circumstances, the detected cutting and/or firing resistance can correspond to the degree of tissue compression. When tissue compression is high, for example, the cutting element resistance can be greater, and when tissue compression is lower, for example, the cutting element resistance can be reduced. Correspondingly, the cutting element resistance can indicate the amount of fluid displacement.

In certain instances, the fluid displacement in clamped tissue can be determined or approximated by the force required to fire the cutting element, i.e., the force-to-fire. The force-to-fire can correspond to the cutting element resistance, for example. Furthermore, the force-to-fire can be measured or approximated by a microcontroller in signal communication with the electric motor that drives the cutting element. For example, where the cutting element resistance is higher, the electric motor can require more current to drive the cutting element through the tissue. Similarly, if the cutting element resistance is lower, the electric motor can require less current to drive the cutting element through the tissue. In such instances, the microcontroller can detect the amount of current drawn by the electric motor during the firing stroke. For example, the microcontroller can include a current sensor, which can detect the current utilized to fire the cutting element through the tissue, for example.

Figure 60:
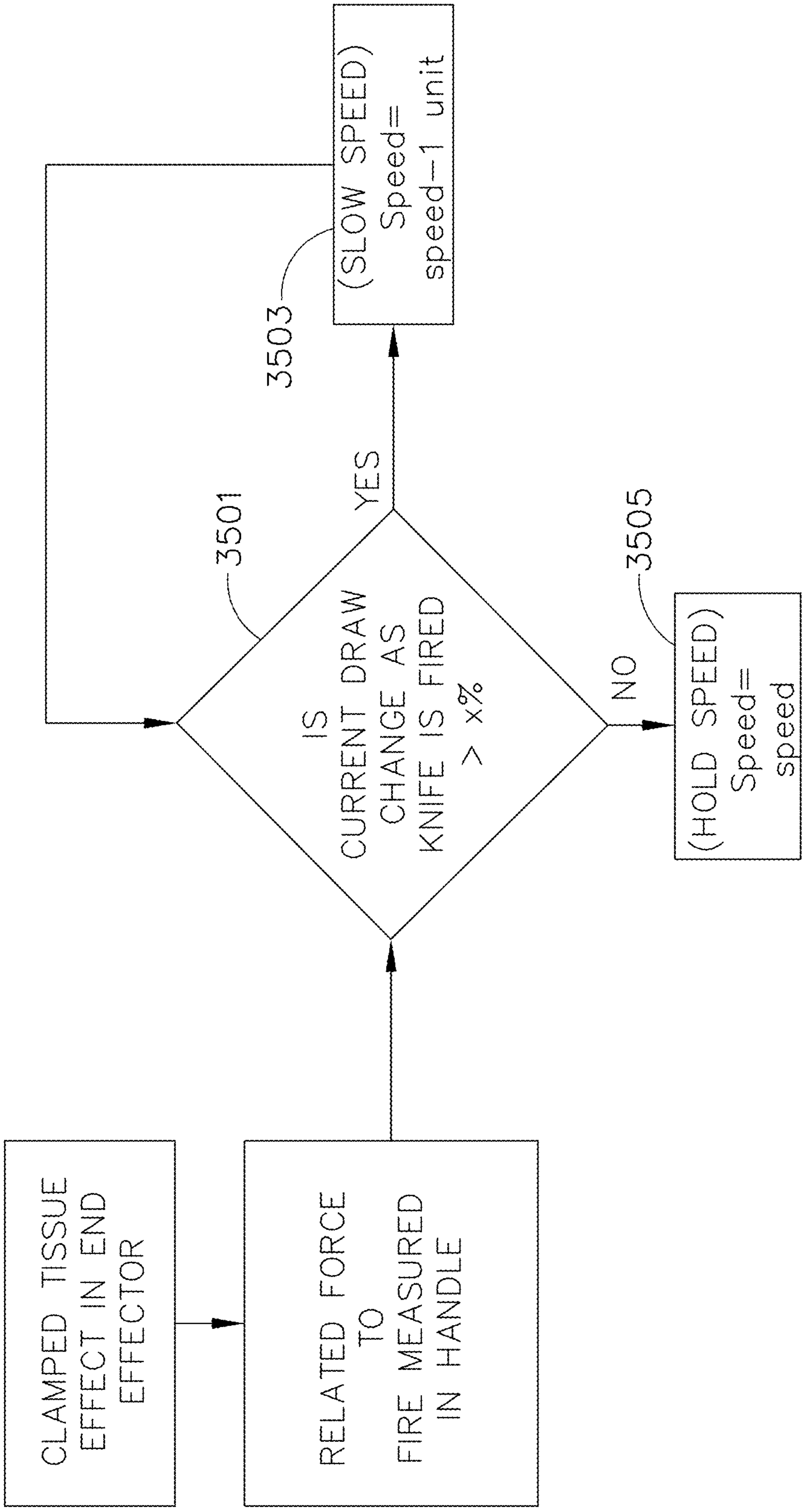
FIG. 60 is a flowchart depicting a method for adjusting the velocity of a firing element according to various embodiments of the present disclosure.

Referring now to FIG. 60, a surgical instrument assembly or system can be configured to detect the compressive force in the clamped tissue. For example, in various instances, an electric motor can drive the firing element, and a microcontroller can be in signal communication with the electric motor. As the electric motor drives the firing element, the microcontroller can determine the current drawn by the electric motor, for example. In such instances, the force-to-fire can correspond to the current drawn by the electric motor throughout the firing stroke, as described above. Referring still to FIG. 60, at step 3501, the microcontroller of the surgical instrument can determine if the current drawn by the electric motor increases during the firing stroke and, if so, can calculate the percentage increase of the current.

In various instances, the microcontroller can compare the current draw increase during the firing stroke to a predefined threshold value. For example, the predefined threshold value can be 5%, 10%, 25%, 50% and/or 100%, for example, and the microcontroller can compare the current increase detected during a firing stroke to the predefined threshold value. In other instances, the threshold increase can be a value or range of values between 5% and 100%, and, in still other instances, the threshold increase can be less than 5% or greater than 100%, for example. For example, if the predefined threshold value is 50%, the microcontroller can compare the percentage of current draw change to 50%, for example. In certain instances, the microcontroller can determine if the current drawn by the electric motor during the firing stroke exceeds a percentage of the maximum current or a baseline value. For example, the microcontroller can determine if the current exceeds 5%, 10%, 25%, 50% and/or 100% of the maximum motor current. In other instances, the microcontroller can compare the current drawn by the electric motor during the firing stroke to a predefined baseline value, for example.

In various instances, the microcontroller can utilize an algorithm to determine the change in current drawn by the electric motor during a firing stroke. For example, the current sensor can detect the current drawn by the electric motor at various times and/or intervals during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Referring still to FIG. 60, if the microcontroller detects a current increase that is greater than the threshold change or value, the microcontroller can proceed to step 3503, and the firing speed of the firing element can be reduced. For example, the microcontroller can communicate with the electric motor to slow the firing speed of the firing element. For example, the firing speed can be reduced by a predefined step unit and/or a predefined percentage. In various instances, the microcontroller can comprise a velocity control module, which can affect changes in the cutting element speed and/or can maintain the cutting element speed. The velocity control module can comprise a resistor, a variable resistor, a pulse width modulation circuit, and/or a frequency modulation circuit, for example. Referring still to FIG. 60, if the current increase is less than the threshold value, the microcontroller can proceed to step 3505, wherein the firing speed of the firing element can be maintained, for example. In various circumstances, the microcontroller can continue to monitor the current drawn by the electric motor and changes thereto during at least a portion of the firing stroke. Moreover, the microcontroller and/or velocity control module thereof can adjust the firing element velocity throughout the firing stroke in accordance with the detected current draw. In such instances, controlling the firing speed based on the approximated fluid flow or displacement in the clamped tissue, for example, can reduce the incidence of staple malformation in the clamped tissue.

Figure 61:
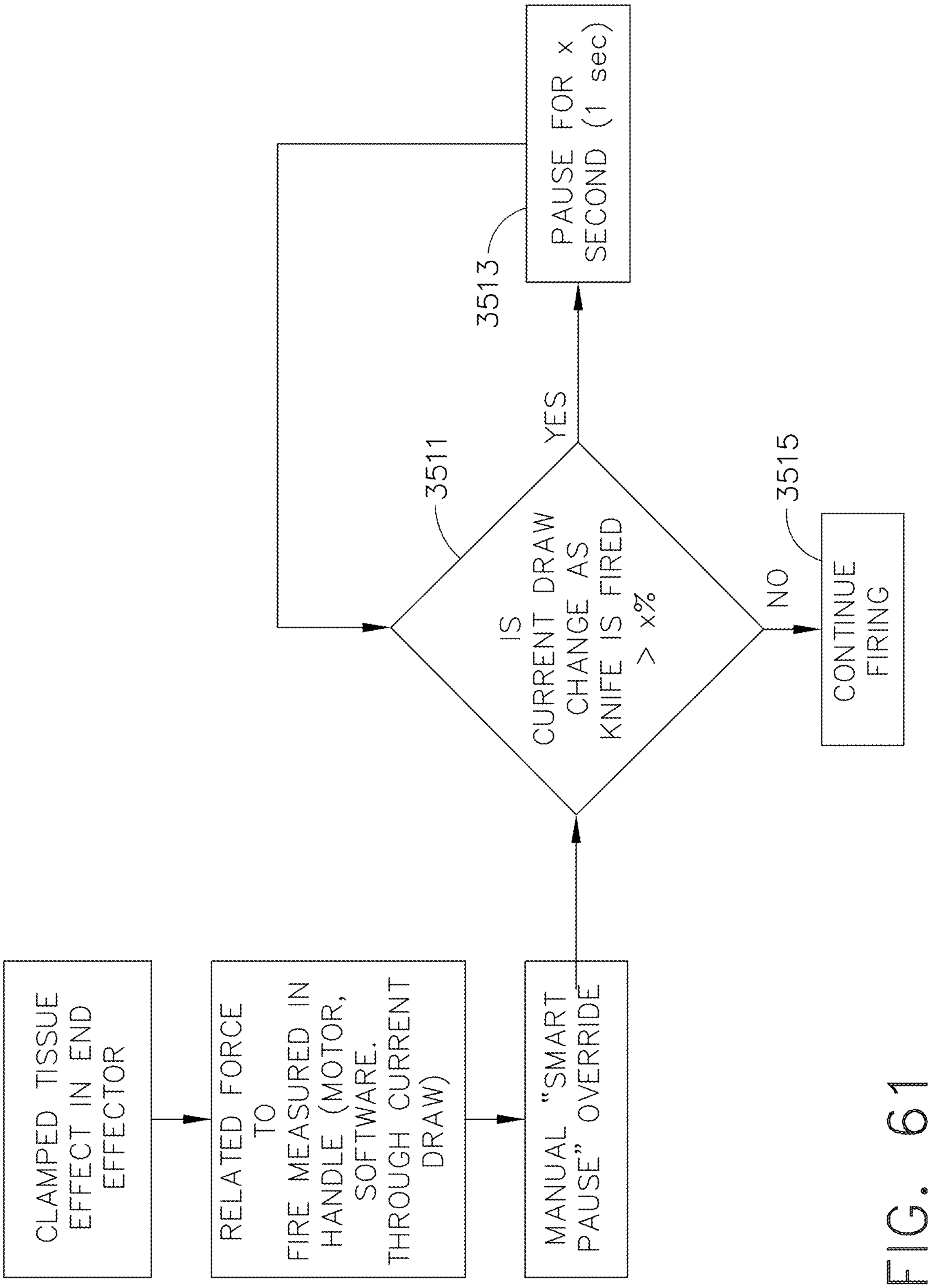
FIG. 61 is a flowchart depicting a method for adjusting the velocity of a firing element according to various embodiments of the present disclosure.

Referring now to FIG. 61, in various instances, the microcontroller can adjust the firing element velocity by pausing the firing element for a predefined period of time. For example, similar to the embodiment depicted in FIG. 60, if the microcontroller detects a current draw that exceeds a predefined threshold value at step 3511, the microcontroller can proceed to step 3513 and the firing element can be paused. For example, the microcontroller can pause movement and/or translation of the firing element for one second if the current increase measured by the microcontroller exceeds the threshold value. In other instances, the firing stroke can be paused for a fraction of a second and/or more than one second, for example. Similar to the process described above, if the current draw increase is less than the threshold value, the microcontroller can proceed to step 3515 and the firing element can continue to progress through the firing stroke without adjusting the velocity of the firing element. In certain instances, the microcontroller can be configured to pause and slow the firing element during a firing stroke. For example, for a first increase in current draw, the firing element can be paused, and for a second, different increase in current draw, the velocity of the firing element can be reduced. In still other circumstances, the microcontroller can command an increase in the velocity of the firing element if the current draw decreases below a threshold value, for example.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the collected biometric associated with motion data of the user, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the controller 2016 and/or the controller 2022 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical system comprising:
- jaws comprising surgical staples positioned therein;
- an electric motor;
- a firing rod coupled to the electric motor and configured to be translated by the electric motor through a firing stoke to deploy the surgical staples from the jaws; and
- a microcontroller configured to:
  - detect a first current draw from the electric motor, during the firing stroke, that exceeds a first predefined threshold value,
  - pause movement of the firing rod in response to detection of the first current draw from the electric motor that exceeds the first predefined threshold value, and
  - following the pause of movement of the firing rod, continue to drive the firing rod through the firing stroke.

2. The surgical system of claim 1, wherein the microcontroller is configured to:
- detect a second current draw from the electric motor that exceeds a second predefined threshold value that is different from the first predefined threshold value; and
- reduce a velocity of the firing rod in response to detection of the second current draw from the electric motor that exceeds the second predefined threshold value.

3. The surgical system of claim 2, wherein the microcontroller is configured to:
- detect the second current draw from the electrical motor and reduce the velocity of the firing rod in response to detection of the second current draw from the electrical motor while driving the firing rod through the firing stroke following the pause.

4. The surgical system of claim 1, wherein the microcontroller is configured to:
- drive the firing rod through the firing stroke at a first velocity prior to the pause of movement of the firing rod; and
- continue driving the firing rod through the firing stroke at the first velocity, following the pause of movement of the firing rod.

5. The surgical system of claim 1, wherein the microcontroller is configured to:
- command an increase in velocity of the firing rod in response to current draw decreasing below a third threshold value.

6. The surgical system of claim 1, wherein the microcontroller is configured to:
- determine fluid displacement in tissue clamped between the jaws; and
- control velocity of the firing rod during the firing stroke based at least in part on the fluid displacement.

7. The surgical system of claim 6, wherein the microcontroller is configured to:
- determine the fluid displacement in tissue clamped between the jaws based at least in part on current draw to the electric motor during the firing stroke.

8. The surgical system of claim 6, further comprising:
- a sensor positioned in the jaws and configured to detect force exerted on the jaws by tissue compressed between the jaws, and
- wherein the microcontroller is configured to determine the fluid displacement based at least in part on the force detected by the sensor.

9. The surgical system of claim 6, further comprising:
- a sensor configured to detect resistance on a cutting element as the cutting element is advanced through the tissue clamped between the jaws during the firing stroke, and
- wherein the microcontroller is configured to determine the fluid displacement based at least in part on the resistance detected by the sensor.

10. A method of controlling a surgical system, the method comprising:
- translating a firing rod through a firing stroke by an electric motor to deploy surgical staples from jaws;
- detecting a first current draw from the electric motor, during the firing stroke, that exceeds a first predetermined threshold value;
- pausing movement of the firing rod in response to detection of the first current draw from the electric motor that exceeds the first predetermined threshold; and
- continuing to drive the firing rod through the firing stroke following the pause movement of the firing rod.

11. The method of claim 10, comprising:
- detecting a second current draw from the electric motor that exceeds a second predefined threshold value that is different from the first predetermined threshold value; and
- reducing a velocity of the firing rod in response to detection of the second current draw from the electric motor that exceeds the second predefined threshold value.

12. The method of claim 11, comprising:
- detecting the second current draw from the electrical motor and reducing the velocity of the firing rod in response to detection of the second current draw from the electrical motor while driving the firing rod through the firing stroke following the pause.

13. The method of claim 11, comprising:
- driving the firing rod through the firing stroke at a first velocity prior to the pause of movement of the firing rod; and
- continuing to drive the firing rod through the firing stroke at the first velocity, following the pause of movement of the firing rod.

14. The method of claim 10, comprising:

commanding an increase in velocity of the firing rod in response to current draw decreasing below a third threshold value.

15. The method of claim 10, comprising:

determining fluid displacement in tissue clamped between the jaws; and controlling velocity of the firing rod during the firing stroke based at least in part on the fluid displacement.

16. The method of claim 15, comprising:

determining the fluid displacement in tissue clamped between the jaws based at least in part on current draw to the electric motor during the firing stroke.

17. The method of claim 15, comprising:

detecting force exerted on the jaws by tissue compressed between the jaws by a sensor positioned in the jaws; and determining the fluid displacement based at least in part on the force detected by the sensor.

18. The method of claim 15, comprising:

detecting resistance on a cutting element by a sensor as the cutting element is advanced through the tissue clamped between the jaws during the firing stroke; and determining the fluid displacement based at least in part on the resistance detected by the sensor.

19. A surgical system comprising:

jaws comprising surgical staples positioned therein;

an electric motor;

a firing rod coupled to the electric motor and configured to be translated by the electric motor through a firing stoke to deploy the surgical staples from the jaws; and a microcontroller configured to:

detect a first change in current draw from the electric motor, during the firing stroke, that exceeds a first predefined threshold change, pause movement of the firing rod in response to detection of the first current draw from the electric motor that exceeds the first predefined threshold change, and following the pause of movement of the firing rod, continue to drive the firing rod through the firing stroke.

20. The surgical system of claim 19, wherein the microcontroller is further configured to:

calculate the first change in the current draw from the electric motor based on a comparison of current draw from the electric motor at different times during the firing stroke.

21. The surgical system of claim 1, wherein the microcontroller is configured to automatically continue to drive the firing rod through the firing stroke.

22. The method of claim 10, wherein continuing to drive the firing rod through the firing stroke following the pause movement of the firing rod is performed automatically.

23. The surgical system of claim 19, wherein the microcontroller is configured to automatically continue to drive the firing rod through the firing stroke.

* * * * *